(12) United States Patent
Cabaniols et al.

(10) Patent No.: US 11,466,291 B2
(45) Date of Patent: Oct. 11, 2022

(54) SEQUENTIAL GENE EDITING IN PRIMARY IMMUNE CELLS

(71) Applicant: CELLECTIS, Paris (FR)

(72) Inventors: Jean-Pierre Cabaniols, Saint Lau la Foret (FR); Jean-Charles Epinat, Les Lilas (FR); Philippe Duchateau, Draveil (FR)

(73) Assignee: CELLECTIS, Paris (FR)

( * ) Notice: Subject to any disclaimer, the term of this patent is extended or adjusted under 35 U.S.C. 154(b) by 76 days.

(21) Appl. No.: 16/314,697

(22) PCT Filed: Jun. 30, 2017

(86) PCT No.: PCT/EP2017/066355
§ 371 (c)(1),
(2) Date: Jan. 2, 2019

(87) PCT Pub. No.: WO2018/007263
PCT Pub. Date: Jan. 11, 2018

(65) Prior Publication Data
US 2020/0208174 A1  Jul. 2, 2020

(30) Foreign Application Priority Data
Jul. 6, 2016 (DK) .......................... PA 201670503

(51) Int. Cl.
| | | |
|---|---|---|
| *C12N 15/86* | (2006.01) | |
| *C12N 5/0783* | (2010.01) | |
| *C12N 9/22* | (2006.01) | |
| *C12N 13/00* | (2006.01) | |
| *C12N 15/113* | (2010.01) | |
| *C12N 15/90* | (2006.01) | |

(52) U.S. Cl.
CPC .......... *C12N 15/86* (2013.01); *C12N 5/0636* (2013.01); *C12N 9/22* (2013.01); *C12N 13/00* (2013.01); *C12N 15/113* (2013.01); *C12N 15/902* (2013.01); *C12N 2310/20* (2017.05); *C12N 2510/00* (2013.01); *C12N 2800/80* (2013.01)

(58) Field of Classification Search
CPC ........ C12N 15/86; C12N 5/0636; C12N 9/22; C12N 13/00; C12N 15/113; C12N 15/902; C12N 2310/20; C12N 2510/00; C12N 2800/80; C12N 2501/599; C12N 15/102; C12N 15/63; A61P 37/04; A61P 35/02; A61P 35/00; C07K 14/7051
See application file for complete search history.

(56) References Cited

U.S. PATENT DOCUMENTS

2018/0171298 A1 * 6/2018 Duchateau .............. A61P 31/12

FOREIGN PATENT DOCUMENTS

| WO | 2013/074916 A1 | 5/2013 |
| WO | 2013/176915 A1 | 11/2013 |
| WO | 2014/191128 A1 | 12/2014 |
| WO | 2015/075195 A1 | 5/2015 |

OTHER PUBLICATIONS

Bierden et al., Gene Therapy vol. 21, pp. 539-548, as recited on the ISR dated Nov. 20, 2017 (Year: 2014).*
Evans et al., TRIM5α Variations Influence Transduction Efficiency With Lentiviral Vectors in Both Human and Rhesus CD34+ Cells In Vitro and In Vivo, Feb. 2014, Molecular Therapy, vol. 22, pp. 348-358. (Year: 2014).*
Hu et al., A Quantitative Chemotherapy Genetic Interaction Map Reveals Factors Associated with PARP Inhibitor Resistance, 2018, Cell Reports, vol. 23, pp. 918-929. (Year: 2018).*
Shaw et al., "Design and Potential of Non-Integrating Lentiviral Vectors", Biomedicines, vol. 2, No. 1, Jan. 27, 2014 (Jan. 27, 2014), pp. 14-35.
Okada et al., "Targeted gene modification in mouse ES cells using integrase-defective lentiviral vectors", Genesis vol. 47, No. 4, Apr. 1, 2009 (Apr. 1, 2009), pp. 217-223.
Berdien et al., TALEN-mediated editing of endogenous T-cell receptors facilitates efficient reprogramming of T lymphocytes by lentiviral gene transfer, Gene Therapy 21(6):539-548 (2014).

* cited by examiner

*Primary Examiner* — Nancy J Leith
(74) *Attorney, Agent, or Firm* — Arrigo, Lee, Guttman & Mouta-Bellum LLP

(57) ABSTRACT

The invention pertains to the field of adaptive cell immunotherapy. It aims at reducing the occurrence of translocations and cell deaths when several specific endonuclease reagents are used altogether to genetically modify primary immune cells at different genetic loci. The method of the invention allows to yield safer immune primary cells harboring several genetic modifications, such as triple or quadruple gene inactivated cells, from populations or subpopulations of cells originating from a single donor or patient, for their subsequent use in therapeutic treatments.

27 Claims, 15 Drawing Sheets

Figure 1:
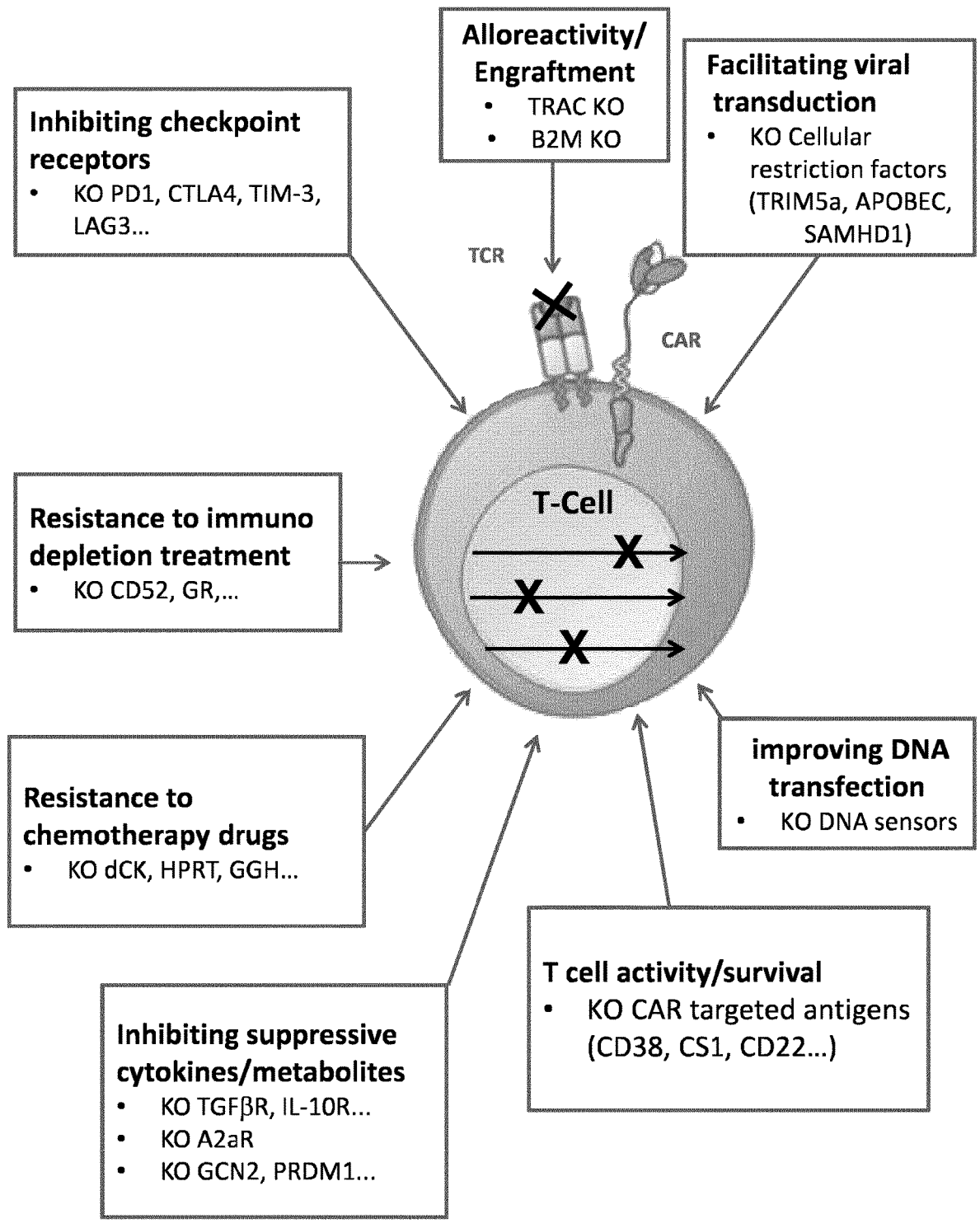

Specification includes a Sequence Listing.

```
                        SEQUENCE LISTING

<160> NUMBER OF SEQ ID NOS: 12

<210> SEQ ID NO 1
<211> LENGTH: 925
<212> TYPE: PRT
<213> ORGANISM: artificial sequence
<220> FEATURE:
<223> OTHER INFORMATION: TRAC TALEN Left

<400> SEQUENCE: 1

Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125
```

```
Gly Val Thr Ala Val Glu Ala Val His Ala Trp Arg Asn Ala Leu Thr
        130                 135                 140

Gly Ala Pro Leu Asn Leu Thr Pro Gln Gln Val Ala Ile Ala Ser
145                 150                 155                 160

Asn Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Ala His Gly Leu Thr Pro Gln Gln Val Val
210                 215                 220

Ala Ile Ala Ser Asn Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Ala His Gly Leu Thr Pro
        275                 280                 285

Glu Gln Val Val Ala Ile Ala Ser His Asp Gly Gly Lys Gln Ala Leu
290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser Asn Ile Gly Gly
        355                 360                 365

Lys Gln Ala Leu Glu Thr Val Gln Ala Leu Leu Pro Val Leu Cys Gln
370                 375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
            420                 425                 430

Asn Ile Gly Gly Lys Gln Ala Leu Glu Thr Val Gln Ala Leu Leu Pro
        435                 440                 445

Val Leu Cys Gln Ala His Gly Leu Thr Pro Gln Gln Val Val Ala Ile
450                 455                 460

Ala Ser Asn Asn Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Ile Gly Gly Lys Gln Ala Leu Glu Thr Val Gln
            500                 505                 510

Ala Leu Leu Pro Val Leu Cys Gln Ala His Gly Leu Thr Pro Gln Gln
        515                 520                 525

Val Val Ala Ile Ala Ser Asn Gly Gly Gly Lys Gln Ala Leu Glu Thr
530                 535                 540
```

Val Gln Arg Leu Leu Pro Val Leu Cys Gln Ala His Gly Leu Thr Pro
545                 550                 555                 560

Glu Gln Val Val Ala Ile Ala Ser Asn Ile Gly Gly Lys Gln Ala Leu
            565                 570                 575

Glu Thr Val Gln Ala Leu Leu Pro Val Leu Cys Gln Ala His Gly Leu
        580                 585                 590

Thr Pro Gln Gln Val Val Ala Ile Ala Ser Asn Gly Gly Lys Gln
    595                 600                 605

Ala Leu Glu Thr Val Gln Arg Leu Leu Pro Val Leu Cys Gln Ala His
610                 615                 620

Gly Leu Thr Pro Glu Gln Val Val Ala Ile Ala Ser His Asp Gly Gly
625                 630                 635                 640

Lys Gln Ala Leu Glu Thr Val Gln Arg Leu Leu Pro Val Leu Cys Gln
            645                 650                 655

Ala His Gly Leu Thr Pro Gln Gln Val Val Ala Ile Ala Ser Asn Gly
        660                 665                 670

Gly Gly Arg Pro Ala Leu Glu Ser Ile Val Ala Gln Leu Ser Arg Pro
    675                 680                 685

Asp Pro Ala Leu Ala Ala Leu Thr Asn Asp His Leu Val Ala Leu Ala
690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
            725                 730                 735

Lys Ser Glu Leu Arg His Lys Leu Lys Tyr Val Pro His Glu Tyr Ile
        740                 745                 750

Glu Leu Ile Glu Ile Ala Arg Asn Ser Thr Gln Asp Arg Ile Leu Glu
    755                 760                 765

Met Lys Val Met Glu Phe Phe Met Lys Val Tyr Gly Tyr Arg Gly Lys
770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
            805                 810                 815

Gly Tyr Asn Leu Pro Ile Gly Gln Ala Asp Glu Met Gln Arg Tyr Val
        820                 825                 830

Glu Glu Asn Gln Thr Arg Asn Lys His Ile Asn Pro Asn Glu Trp Trp
    835                 840                 845

Lys Val Tyr Pro Ser Ser Val Thr Glu Phe Lys Phe Leu Phe Val Ser
850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
            885                 890                 895

Gly Gly Glu Met Ile Lys Ala Gly Thr Leu Thr Leu Glu Glu Val Arg
        900                 905                 910

Arg Lys Phe Asn Asn Gly Glu Ile Asn Phe Ala Ala Asp
    915                 920                 925

<210> SEQ ID NO 2
<211> LENGTH: 925
<212> TYPE: PRT
<213> ORGANISM: artificial sequence
<220> FEATURE:
<223> OTHER INFORMATION: TRAC TALEN Right

<400> SEQUENCE: 2

```
Met Gly Asp Pro Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
                20                  25                  30

Val Arg Ser Thr Val Ala Gln His His Glu Ala Leu Val Gly His Gly
            35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
                100                 105                 110

Pro Leu Gln Leu Asp Thr Gly Gln Leu Leu Lys Ile Ala Lys Arg Gly
                115                 120                 125

Gly Val Thr Ala Val Glu Ala Val His Ala Trp Arg Asn Ala Leu Thr
            130                 135                 140

Gly Ala Pro Leu Asn Leu Thr Pro Glu Gln Val Val Ala Ile Ala Ser
145                 150                 155                 160

His Asp Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
                180                 185                 190

Ala Ser Asn Gly Gly Gly Lys Gln Ala Leu Glu Thr Val Gln Arg Leu
            195                 200                 205

Leu Pro Val Leu Cys Gln Ala His Gly Leu Thr Pro Glu Gln Val Val
        210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser Asn Ile Gly Gly Lys Gln Ala Leu Glu Thr
                260                 265                 270

Val Gln Ala Leu Leu Pro Val Leu Cys Gln Ala His Gly Leu Thr Pro
        275                 280                 285

Gln Gln Val Val Ala Ile Ala Ser Asn Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
            325                 330                 335

Ala Leu Glu Thr Val Gln Arg Leu Leu Pro Val Leu Cys Gln Ala His
                340                 345                 350

Gly Leu Thr Pro Gln Gln Val Val Ala Ile Ala Ser Asn Gly Gly Gly
            355                 360                 365

Lys Gln Ala Leu Glu Thr Val Gln Arg Leu Leu Pro Val Leu Cys Gln
        370                 375                 380

Ala His Gly Leu Thr Pro Gln Gln Val Val Ala Ile Ala Ser Asn Asn
385                 390                 395                 400

Gly Gly Lys Gln Ala Leu Glu Thr Val Gln Arg Leu Leu Pro Val Leu
```

-continued

```
                405                 410                 415
Cys Gln Ala His Gly Leu Thr Pro Gln Gln Val Val Ala Ile Ala Ser
                420                 425                 430

Asn Asn Gly Gly Lys Gln Ala Leu Glu Thr Val Gln Arg Leu Leu Pro
                435                 440                 445

Val Leu Cys Gln Ala His Gly Leu Thr Pro Gln Gln Val Val Ala Ile
450                 455                 460

Ala Ser Asn Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser Asn Ile Gly Gly Lys Gln Ala Leu Glu Thr Val Gln
                500                 505                 510

Ala Leu Leu Pro Val Leu Cys Gln Ala His Gly Leu Thr Pro Glu Gln
                515                 520                 525

Val Val Ala Ile Ala Ser His Asp Gly Gly Lys Gln Ala Leu Glu Thr
                530                 535                 540

Val Gln Arg Leu Leu Pro Val Leu Cys Gln Ala His Gly Leu Thr Pro
545                 550                 555                 560

Glu Gln Val Val Ala Ile Ala Ser Asn Ile Gly Gly Lys Gln Ala Leu
                565                 570                 575

Glu Thr Val Gln Ala Leu Leu Pro Val Leu Cys Gln Ala His Gly Leu
                580                 585                 590

Thr Pro Glu Gln Val Val Ala Ile Ala Ser His Asp Gly Gly Lys Gln
                595                 600                 605

Ala Leu Glu Thr Val Gln Arg Leu Leu Pro Val Leu Cys Gln Ala His
                610                 615                 620

Gly Leu Thr Pro Gln Gln Val Val Ala Ile Ala Ser Asn Asn Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
                660                 665                 670

Gly Gly Arg Pro Ala Leu Glu Ser Ile Val Ala Gln Leu Ser Arg Pro
                675                 680                 685

Asp Pro Ala Leu Ala Ala Leu Thr Asn Asp His Leu Val Ala Leu Ala
                690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
                740                 745                 750

Glu Leu Ile Glu Ile Ala Arg Asn Ser Thr Gln Asp Arg Ile Leu Glu
                755                 760                 765

Met Lys Val Met Glu Phe Phe Met Lys Val Tyr Gly Tyr Arg Gly Lys
                770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
                820                 825                 830
```

```
Glu Glu Asn Gln Thr Arg Asn Lys His Ile Asn Pro Asn Glu Trp Trp
            835                 840                 845
Lys Val Tyr Pro Ser Ser Val Thr Glu Phe Lys Phe Leu Phe Val Ser
        850                 855                 860
Gly His Phe Lys Gly Asn Tyr Lys Ala Gln Leu Thr Arg Leu Asn His
865                 870                 875                 880
Ile Thr Asn Cys Asn Gly Ala Val Leu Ser Val Glu Leu Leu Ile
                885                 890                 895
Gly Gly Glu Met Ile Lys Ala Gly Thr Leu Thr Leu Glu Glu Val Arg
                900                 905                 910
Arg Lys Phe Asn Asn Gly Glu Ile Asn Phe Ala Ala Asp
            915                 920                 925

<210> SEQ ID NO 3
<211> LENGTH: 925
<212> TYPE: PRT
<213> ORGANISM: artificial sequence
<220> FEATURE:
<223> OTHER INFORMATION: CD52 TALEN Left

<400> SEQUENCE: 3

Met Gly Asp Pro Lys Lys Arg Lys Val Ile Asp Ile Ala Asp Leu
1               5                   10                  15
Arg Thr Leu Gly Tyr Ser Gln Gln Gln Glu Lys Ile Lys Pro Lys
            20                  25                  30
Val Arg Ser Thr Val Ala Gln His His Glu Ala Leu Val Gly His Gly
            35                  40                  45
Phe Thr His Ala His Ile Val Ala Leu Ser Gln His Pro Ala Ala Leu
    50                  55                  60
Gly Thr Val Ala Val Lys Tyr Gln Asp Met Ile Ala Ala Leu Pro Glu
65                  70                  75                  80
Ala Thr His Glu Ala Ile Val Gly Val Gly Lys Gln Trp Ser Gly Ala
                85                  90                  95
Arg Ala Leu Glu Ala Leu Leu Thr Val Ala Gly Glu Leu Arg Gly Pro
                100                 105                 110
Pro Leu Gln Leu Asp Thr Gly Gln Leu Leu Lys Ile Ala Lys Arg Gly
            115                 120                 125
Gly Val Thr Ala Val Glu Ala Val His Ala Trp Arg Asn Ala Leu Thr
        130                 135                 140
Gly Ala Pro Leu Asn Leu Thr Pro Gln Gln Val Val Ala Ile Ala Ser
145                 150                 155                 160
Asn Gly Gly Gly Lys Gln Ala Leu Glu Thr Val Gln Arg Leu Leu Pro
                165                 170                 175
Val Leu Cys Gln Ala His Gly Leu Thr Pro Glu Gln Val Val Ala Ile
                180                 185                 190
Ala Ser His Asp Gly Gly Lys Gln Ala Leu Glu Thr Val Gln Arg Leu
            195                 200                 205
Leu Pro Val Leu Cys Gln Ala His Gly Leu Thr Pro Glu Gln Val Val
        210                 215                 220
Ala Ile Ala Ser His Asp Gly Gly Lys Gln Ala Leu Glu Thr Val Gln
225                 230                 235                 240
Arg Leu Leu Pro Val Leu Cys Gln Ala His Gly Leu Thr Pro Gln Gln
                245                 250                 255
Val Val Ala Ile Ala Ser Asn Gly Gly Gly Lys Gln Ala Leu Glu Thr
                260                 265                 270
```

```
Val Gln Arg Leu Leu Pro Val Leu Cys Gln Ala His Gly Leu Thr Pro
            275                 280                 285

Glu Gln Val Val Ala Ile Ala Ser His Asp Gly Gly Lys Gln Ala Leu
            290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Gly Gly Gly
            355                 360                 365

Lys Gln Ala Leu Glu Thr Val Gln Arg Leu Leu Pro Val Leu Cys Gln
            370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Glu Gln Val Val Ala Ile Ala Ser
            420                 425                 430

His Asp Gly Gly Lys Gln Ala Leu Glu Thr Val Gln Arg Leu Leu Pro
            435                 440                 445

Val Leu Cys Gln Ala His Gly Leu Thr Pro Gln Gln Val Val Ala Ile
450                 455                 460

Ala Ser Asn Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser His Asp Gly Gly Lys Gln Ala Leu Glu Thr Val Gln
            500                 505                 510

Arg Leu Leu Pro Val Leu Cys Gln Ala His Gly Leu Thr Pro Glu Gln
            515                 520                 525

Val Val Ala Ile Ala Ser Asn Ile Gly Gly Lys Gln Ala Leu Glu Thr
            530                 535                 540

Val Gln Ala Leu Leu Pro Val Leu Cys Gln Ala His Gly Leu Thr Pro
545                 550                 555                 560

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser His Asp Gly Gly Lys Gln
            595                 600                 605

Ala Leu Glu Thr Val Gln Arg Leu Leu Pro Val Leu Cys Gln Ala His
            610                 615                 620

Gly Leu Thr Pro Glu Gln Val Val Ala Ile Ala Ser Asn Ile Gly Gly
625                 630                 635                 640

Lys Gln Ala Leu Glu Thr Val Gln Ala Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
            675                 680                 685
```

-continued

Asp Pro Ala Leu Ala Ala Leu Thr Asn Asp His Leu Val Ala Leu Ala
    690                 695                 700
Cys Leu Gly Gly Arg Pro Ala Leu Asp Ala Val Lys Lys Gly Leu Gly
705                 710                 715                 720
Asp Pro Ile Ser Arg Ser Gln Leu Val Lys Ser Glu Leu Glu Glu Lys
            725                 730                 735
Lys Ser Glu Leu Arg His Lys Leu Lys Tyr Val Pro His Glu Tyr Ile
            740                 745                 750
Glu Leu Ile Glu Ile Ala Arg Asn Ser Thr Gln Asp Arg Ile Leu Glu
        755                 760                 765
Met Lys Val Met Glu Phe Phe Met Lys Val Tyr Gly Tyr Arg Gly Lys
770                 775                 780
His Leu Gly Gly Ser Arg Lys Pro Asp Gly Ala Ile Tyr Thr Val Gly
785                 790                 795                 800
Ser Pro Ile Asp Tyr Gly Val Ile Val Asp Thr Lys Ala Tyr Ser Gly
            805                 810                 815
Gly Tyr Asn Leu Pro Ile Gly Gln Ala Asp Glu Met Gln Arg Tyr Val
        820                 825                 830
Glu Glu Asn Gln Thr Arg Asn Lys His Ile Asn Pro Asn Glu Trp Trp
    835                 840                 845
Lys Val Tyr Pro Ser Ser Val Thr Glu Phe Lys Phe Leu Phe Val Ser
850                 855                 860
Gly His Phe Lys Gly Asn Tyr Lys Ala Gln Leu Thr Arg Leu Asn His
865                 870                 875                 880
Ile Thr Asn Cys Asn Gly Ala Val Leu Ser Val Glu Glu Leu Leu Ile
            885                 890                 895
Gly Gly Glu Met Ile Lys Ala Gly Thr Leu Thr Leu Glu Glu Val Arg
        900                 905                 910
Arg Lys Phe Asn Asn Gly Glu Ile Asn Phe Ala Ala Asp
    915                 920                 925

<210> SEQ ID NO 4
<211> LENGTH: 925
<212> TYPE: PRT
<213> ORGANISM: artificial sequence
<220> FEATURE:
<223> OTHER INFORMATION: CD52 TALEN Right

<400> SEQUENCE: 4

Met Gly Asp Pro Lys Lys Lys Arg Lys Val Ile Asp Ile Ala Asp Leu
1               5                   10                  15
Arg Thr Leu Gly Tyr Ser Gln Gln Gln Gln Glu Lys Ile Lys Pro Lys
            20                  25                  30
Val Arg Ser Thr Val Ala Gln His His Glu Ala Leu Val Gly His Gly
        35                  40                  45
Phe Thr His Ala His Ile Val Ala Leu Ser Gln His Pro Ala Ala Leu
    50                  55                  60
Gly Thr Val Ala Val Lys Tyr Gln Asp Met Ile Ala Ala Leu Pro Glu
65                  70                  75                  80
Ala Thr His Glu Ala Ile Val Gly Val Gly Lys Gln Trp Ser Gly Ala
            85                  90                  95
Arg Ala Leu Glu Ala Leu Leu Thr Val Ala Gly Glu Leu Arg Gly Pro
        100                 105                 110
Pro Leu Gln Leu Asp Thr Gly Gln Leu Leu Lys Ile Ala Lys Arg Gly
    115                 120                 125

```
Gly Val Thr Ala Val Glu Ala Val His Ala Trp Arg Asn Ala Leu Thr
            130                 135                 140
Gly Ala Pro Leu Asn Leu Thr Pro Gln Gln Val Val Ala Ile Ala Ser
145                 150                 155                 160
Asn Gly Gly Lys Gln Ala Leu Glu Thr Val Gln Arg Leu Leu Pro
                165                 170                 175
Val Leu Cys Gln Ala His Gly Leu Thr Pro Gln Gln Val Val Ala Ile
            180                 185                 190
Ala Ser Asn Asn Gly Gly Lys Gln Ala Leu Glu Thr Val Gln Arg Leu
            195                 200                 205
Leu Pro Val Leu Cys Gln Ala His Gly Leu Thr Pro Glu Gln Val Val
210                 215                 220
Ala Ile Ala Ser His Asp Gly Gly Lys Gln Ala Leu Glu Thr Val Gln
225                 230                 235                 240
Arg Leu Leu Pro Val Leu Cys Gln Ala His Gly Leu Thr Pro Gln Gln
                245                 250                 255
Val Val Ala Ile Ala Ser Asn Gly Gly Gly Lys Gln Ala Leu Glu Thr
            260                 265                 270
Val Gln Arg Leu Leu Pro Val Leu Cys Gln Ala His Gly Leu Thr Pro
        275                 280                 285
Glu Gln Val Val Ala Ile Ala Ser His Asp Gly Gly Lys Gln Ala Leu
290                 295                 300
Glu Thr Val Gln Arg Leu Leu Pro Val Leu Cys Gln Ala His Gly Leu
305                 310                 315                 320
Thr Pro Gln Gln Val Val Ala Ile Ala Ser Asn Gly Gly Gly Lys Gln
                325                 330                 335
Ala Leu Glu Thr Val Gln Arg Leu Leu Pro Val Leu Cys Gln Ala His
            340                 345                 350
Gly Leu Thr Pro Gln Gln Val Val Ala Ile Ala Ser Asn Gly Gly Gly
            355                 360                 365
Lys Gln Ala Leu Glu Thr Val Gln Arg Leu Leu Pro Val Leu Cys Gln
370                 375                 380
Ala His Gly Leu Thr Pro Glu Gln Val Val Ala Ile Ala Ser Asn Ile
385                 390                 395                 400
Gly Gly Lys Gln Ala Leu Glu Thr Val Gln Ala Leu Leu Pro Val Leu
                405                 410                 415
Cys Gln Ala His Gly Leu Thr Pro Glu Gln Val Val Ala Ile Ala Ser
            420                 425                 430
His Asp Gly Gly Lys Gln Ala Leu Glu Thr Val Gln Arg Leu Leu Pro
            435                 440                 445
Val Leu Cys Gln Ala His Gly Leu Thr Pro Glu Gln Val Val Ala Ile
450                 455                 460
Ala Ser His Asp Gly Gly Lys Gln Ala Leu Glu Thr Val Gln Arg Leu
465                 470                 475                 480
Leu Pro Val Leu Cys Gln Ala His Gly Leu Thr Pro Gln Gln Val Val
                485                 490                 495
Ala Ile Ala Ser Asn Gly Gly Gly Lys Gln Ala Leu Glu Thr Val Gln
            500                 505                 510
Arg Leu Leu Pro Val Leu Cys Gln Ala His Gly Leu Thr Pro Gln Gln
            515                 520                 525
Val Val Ala Ile Ala Ser Asn Asn Gly Gly Lys Gln Ala Leu Glu Thr
530                 535                 540
Val Gln Arg Leu Leu Pro Val Leu Cys Gln Ala His Gly Leu Thr Pro
```

-continued

```
                545                 550                 555                 560
            Gln Gln Val Val Ala Ile Ala Ser Asn Gly Gly Gly Lys Gln Ala Leu
                            565                 570                 575
            Glu Thr Val Gln Arg Leu Leu Pro Val Leu Cys Gln Ala His Gly Leu
                            580                 585                 590
            Thr Pro Glu Gln Val Val Ala Ile Ala Ser Asn Ile Gly Gly Lys Gln
                            595                 600                 605
            Ala Leu Glu Thr Val Gln Ala Leu Leu Pro Val Leu Cys Gln Ala His
                            610                 615                 620
            Gly Leu Thr Pro Glu Gln Val Val Ala Ile Ala Ser His Asp Gly Gly
            625                 630                 635                 640
            Lys Gln Ala Leu Glu Thr Val Gln Arg Leu Leu Pro Val Leu Cys Gln
                            645                 650                 655
            Ala His Gly Leu Thr Pro Gln Gln Val Val Ala Ile Ala Ser Asn Gly
                            660                 665                 670
            Gly Gly Arg Pro Ala Leu Glu Ser Ile Val Ala Gln Leu Ser Arg Pro
                            675                 680                 685
            Asp Pro Ala Leu Ala Ala Leu Thr Asn Asp His Leu Val Ala Leu Ala
                            690                 695                 700
            Cys Leu Gly Gly Arg Pro Ala Leu Asp Ala Val Lys Lys Gly Leu Gly
            705                 710                 715                 720
            Asp Pro Ile Ser Arg Ser Gln Leu Val Lys Ser Glu Leu Glu Glu Lys
                            725                 730                 735
            Lys Ser Glu Leu Arg His Lys Leu Lys Tyr Val Pro His Glu Tyr Ile
                            740                 745                 750
            Glu Leu Ile Glu Ile Ala Arg Asn Ser Thr Gln Asp Arg Ile Leu Glu
                            755                 760                 765
            Met Lys Val Met Glu Phe Phe Met Lys Val Tyr Gly Tyr Arg Gly Lys
                            770                 775                 780
            His Leu Gly Gly Ser Arg Lys Pro Asp Gly Ala Ile Tyr Thr Val Gly
            785                 790                 795                 800
            Ser Pro Ile Asp Tyr Gly Val Ile Val Asp Thr Lys Ala Tyr Ser Gly
                            805                 810                 815
            Gly Tyr Asn Leu Pro Ile Gly Gln Ala Asp Glu Met Gln Arg Tyr Val
                            820                 825                 830
            Glu Glu Asn Gln Thr Arg Asn Lys His Ile Asn Pro Asn Glu Trp Trp
                            835                 840                 845
            Lys Val Tyr Pro Ser Ser Val Thr Glu Phe Lys Phe Leu Phe Val Ser
            850                 855                 860
            Gly His Phe Lys Gly Asn Tyr Lys Ala Gln Leu Thr Arg Leu Asn His
            865                 870                 875                 880
            Ile Thr Asn Cys Asn Gly Ala Val Leu Ser Val Glu Glu Leu Leu Ile
                            885                 890                 895
            Gly Gly Glu Met Ile Lys Ala Gly Thr Leu Thr Leu Glu Glu Val Arg
                            900                 905                 910
            Arg Lys Phe Asn Asn Gly Glu Ile Asn Phe Ala Ala Asp
                            915                 920                 925

<210> SEQ ID NO 5
<211> LENGTH: 925
<212> TYPE: PRT
<213> ORGANISM: artificial sequence
<220> FEATURE:
<223> OTHER INFORMATION: PD-1 TALEN Left
```

```
<400> SEQUENCE: 5

Met Gly Asp Pro Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
50                  55                      60

Gly Thr Val Ala Val Lys Tyr Gln Asp Met Ile Ala Ala Leu Pro Glu
65                      70                  75                  80

Ala Thr His Glu Ala Ile Val Gly Val Gly Lys Gln Trp Ser Gly Ala
                85                  90                      95

Arg Ala Leu Glu Ala Leu Leu Thr Val Ala Gly Glu Leu Arg Gly Pro
            100                 105                     110

Pro Leu Gln Leu Asp Thr Gly Gln Leu Leu Lys Ile Ala Lys Arg Gly
            115                 120                     125

Gly Val Thr Ala Val Glu Ala Val His Ala Trp Arg Asn Ala Leu Thr
130                     135                     140

Gly Ala Pro Leu Asn Leu Thr Pro Glu Gln Val Val Ala Ile Ala Ser
145                     150                     155                 160

Gly Asn Gly Gly Lys Gln Ala Leu Glu Thr Val Gln Ala Leu Leu Pro
                165                     170                 175

Val Leu Cys Gln Ala His Gly Leu Thr Pro Glu Gln Val Val Ala Ile
            180                     185                 190

Ala Ser His Asp Gly Gly Lys Gln Ala Leu Glu Thr Val Gln Arg Leu
            195                     200                 205

Leu Pro Val Leu Cys Gln Ala His Gly Leu Thr Pro Glu Gln Val Val
210                     215                     220

Ala Ile Ala Ser His Asp Gly Gly Lys Gln Ala Leu Glu Thr Val Gln
225                     230                     235                 240

Arg Leu Leu Pro Val Leu Cys Gln Ala His Gly Leu Thr Pro Gln Gln
            245                     250                 255

Val Val Ala Ile Ala Ser Asn Gly Gly Lys Gln Ala Leu Glu Thr
            260                     265                 270

Val Gln Arg Leu Leu Pro Val Leu Cys Gln Ala His Gly Leu Thr Pro
        275                     280                 285

Glu Gln Val Val Ala Ile Ala Ser His Asp Gly Gly Lys Gln Ala Leu
    290                     295                 300

Glu Thr Val Gln Arg Leu Leu Pro Val Leu Cys Gln Ala His Gly Leu
305                     310                 315                 320

Thr Pro Gln Gln Val Val Ala Ile Ala Ser Asn Gly Gly Lys Gln
            325                     330                 335

Ala Leu Glu Thr Val Gln Arg Leu Leu Pro Val Leu Cys Gln Ala His
            340                     345                 350

Gly Leu Thr Pro Gln Gln Val Val Ala Ile Ala Ser Asn Gly Gly
            355                     360                 365

Lys Gln Ala Leu Glu Thr Val Gln Arg Leu Leu Pro Val Leu Cys Gln
            370                     375                 380

Ala His Gly Leu Thr Pro Gln Gln Val Val Ala Ile Ala Ser Asn Gly
385                     390                     395                 400

Gly Gly Lys Gln Ala Leu Glu Thr Val Gln Arg Leu Leu Pro Val Leu
                405                     410                 415
```

```
Cys Gln Ala His Gly Leu Thr Pro Gln Gln Val Val Ala Ile Ala Ser
            420                 425                 430

Gly Arg Gly Gly Lys Gln Ala Leu Glu Thr Val Gln Arg Leu Leu Pro
            435                 440                 445

Val Leu Cys Gln Ala His Gly Leu Thr Pro Gln Gln Val Val Ala Ile
    450                 455                 460

Ala Ser Asn Asn Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Asn Gly Gly Lys Gln Ala Leu Glu Thr Val Gln
            500                 505                 510

Arg Leu Leu Pro Val Leu Cys Gln Ala His Gly Leu Thr Pro Gln Gln
            515                 520                 525

Val Val Ala Ile Ala Ser Asn Asn Gly Gly Lys Gln Ala Leu Glu Thr
            530                 535                 540

Val Gln Arg Leu Leu Pro Val Leu Cys Gln Ala His Gly Leu Thr Pro
545                 550                 555                 560

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser His Asp Gly Gly Lys Gln
            595                 600                 605

Ala Leu Glu Thr Val Gln Arg Leu Leu Pro Val Leu Cys Gln Ala His
            610                 615                 620

Gly Leu Thr Pro Glu Gln Val Val Ala Ile Ala Ser Asn Ile Gly Gly
625                 630                 635                 640

Lys Gln Ala Leu Glu Thr Val Gln Ala Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
            675                 680                 685

Asp Pro Ala Leu Ala Ala Leu Thr Asn Asp His Leu Val Ala Leu Ala
            690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
            770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
            820                 825                 830
```

Glu Glu Asn Gln Thr Arg Asn Lys His Ile Asn Pro Asn Glu Trp Trp
            835                 840                 845

Lys Val Tyr Pro Ser Ser Val Thr Glu Phe Lys Phe Leu Phe Val Ser
850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
                900                 905                 910

Arg Lys Phe Asn Asn Gly Glu Ile Asn Phe Ala Ala Asp
            915                 920                 925

<210> SEQ ID NO 6
<211> LENGTH: 924
<212> TYPE: PRT
<213> ORGANISM: artificial sequence
<220> FEATURE:
<223> OTHER INFORMATION: PD-1 TALEN Right

<400> SEQUENCE: 6

Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
            35                  40                  45

Phe Thr His Ala His Ile Val Ala Leu Ser Gln His Pro Ala Ala Leu
50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
            115                 120                 125

Gly Val Thr Ala Val Glu Ala Val His Ala Trp Arg Asn Ala Leu Thr
130                 135                 140

Gly Ala Pro Leu Asn Leu Thr Pro Glu Gln Val Val Ala Ile Ala Ser
145                 150                 155                 160

His Asp Gly Gly Lys Gln Ala Leu Glu Thr Val Gln Arg Leu Leu Pro
                165                 170                 175

Val Leu Cys Gln Ala His Gly Leu Thr Pro Gln Gln Val Val Ala Ile
            180                 185                 190

Ala Ser Asn Gly Gly Gly Lys Gln Ala Leu Glu Thr Val Gln Arg Leu
            195                 200                 205

Leu Pro Val Leu Cys Gln Ala His Gly Leu Thr Pro Glu Gln Val Val
            210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Gln Gln
                245                 250                 255

Val Val Ala Ile Ala Ser Asn Gly Gly Gly Lys Gln Ala Leu Glu Thr
            260                 265                 270

```
Val Gln Arg Leu Leu Pro Val Leu Cys Gln Ala His Gly Leu Thr Pro
            275                 280                 285

Gln Gln Val Val Ala Ile Ala Ser Asn Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Gly Gly Lys Gln
                325                 330                 335

Ala Leu Glu Thr Val Gln Arg Leu Leu Pro Val Leu Cys Gln Ala His
            340                 345                 350

Gly Leu Thr Pro Gln Gln Val Val Ala Ile Ala Ser Asn Asn Gly Gly
        355                 360                 365

Lys Gln Ala Leu Glu Thr Val Gln Arg Leu Leu Pro Val Leu Cys Gln
370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Gln Gln Val Val Ala Ile Ala Ser
            420                 425                 430

Asn Gly Gly Lys Gln Ala Leu Glu Thr Val Gln Arg Leu Leu Pro
    435                 440                 445

Val Leu Cys Gln Ala His Gly Leu Thr Pro Glu Gln Val Val Ala Ile
        450                 455                 460

Ala Ser His Asp Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Gly Gly Lys Gln Ala Leu Glu Thr Val Gln
            500                 505                 510

Arg Leu Leu Pro Val Leu Cys Gln Ala His Gly Leu Thr Pro Gln Gln
        515                 520                 525

Val Val Ala Ile Ala Ser Asn Asn Gly Gly Lys Gln Ala Leu Glu Thr
545                 530                 535                 540

Val Gln Arg Leu Leu Pro Val Leu Cys Gln Ala His Gly Leu Thr Pro
545                 550                 555                 560

Glu Gln Val Val Ala Ile Ala Ser Asn Gly Gly Lys Gln Ala Leu Glu
                565                 570                 575

Thr Val Gln Arg Leu Leu Pro Val Leu Cys Gln Ala His Gly Leu Thr
            580                 585                 590

Pro Gln Gln Val Val Ala Ile Ala Ser Asn Asn Gly Gly Lys Gln Ala
        595                 600                 605

Leu Glu Thr Val Gln Arg Leu Leu Pro Val Leu Cys Gln Ala His Gly
610                 615                 620

Leu Thr Pro Glu Gln Val Val Ala Ile Ala Ser His Asp Gly Gly Lys
625                 630                 635                 640

Gln Ala Leu Glu Thr Val Gln Arg Leu Leu Pro Val Leu Cys Gln Ala
                645                 650                 655

His Gly Leu Thr Pro Gln Gln Val Val Ala Ile Ala Ser Asn Gly Gly
            660                 665                 670

Gly Arg Pro Ala Leu Glu Ser Ile Val Ala Gln Leu Ser Arg Pro Asp
        675                 680                 685

Pro Ala Leu Ala Ala Leu Thr Asn Asp His Leu Val Ala Leu Ala Cys
```

```
                      690                 695                 700
Leu Gly Gly Arg Pro Ala Leu Asp Ala Val Lys Lys Gly Leu Gly Asp
705                 710                 715                 720

Pro Ile Ser Arg Ser Gln Leu Val Lys Ser Glu Leu Glu Glu Lys Lys
                725                 730                 735

Ser Glu Leu Arg His Lys Leu Lys Tyr Val Pro His Glu Tyr Ile Glu
            740                 745                 750

Leu Ile Glu Ile Ala Arg Asn Ser Thr Gln Asp Arg Ile Leu Glu Met
        755                 760                 765

Lys Val Met Glu Phe Phe Met Lys Val Tyr Gly Tyr Arg Gly Lys His
    770                 775                 780

Leu Gly Gly Ser Arg Lys Pro Asp Gly Ala Ile Tyr Thr Val Gly Ser
785                 790                 795                 800

Pro Ile Asp Tyr Gly Val Ile Val Asp Thr Lys Ala Tyr Ser Gly Gly
                805                 810                 815

Tyr Asn Leu Pro Ile Gly Gln Ala Asp Glu Met Gln Arg Tyr Val Glu
            820                 825                 830

Glu Asn Gln Thr Arg Asn Lys His Ile Asn Pro Asn Glu Trp Trp Lys
        835                 840                 845

Val Tyr Pro Ser Ser Val Thr Glu Phe Lys Phe Leu Phe Val Ser Gly
    850                 855                 860

His Phe Lys Gly Asn Tyr Lys Ala Gln Leu Thr Arg Leu Asn His Ile
865                 870                 875                 880

Thr Asn Cys Asn Gly Ala Val Leu Ser Val Glu Glu Leu Leu Ile Gly
                885                 890                 895

Gly Glu Met Ile Lys Ala Gly Thr Leu Thr Leu Glu Glu Val Arg Arg
            900                 905                 910

Lys Phe Asn Asn Gly Glu Ile Asn Phe Ala Ala Asp
        915                 920

<210> SEQ ID NO 7
<211> LENGTH: 925
<212> TYPE: PRT
<213> ORGANISM: artificial sequence
<220> FEATURE:
<223> OTHER INFORMATION: CD38 TALEN Left

<400> SEQUENCE: 7

Met Gly Asp Pro Lys Lys Lys Arg Lys Val Ile Asp Ile Ala Asp Leu
1               5                   10                  15

Arg Thr Leu Gly Tyr Ser Gln Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
```

```
                130                 135                 140
Gly Ala Pro Leu Asn Leu Thr Pro Gln Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Ala His Gly Leu Thr Pro Glu Gln Val Val Ala Ile
                180                 185                 190

Ala Ser His Asp Gly Gly Lys Gln Ala Leu Glu Thr Val Gln Arg Leu
                195                 200                 205

Leu Pro Val Leu Cys Gln Ala His Gly Leu Thr Pro Gln Gln Val Val
210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser Asn Ile Gly Gly Lys Gln Ala Leu Glu Thr
                260                 265                 270

Val Gln Ala Leu Leu Pro Val Leu Cys Gln Ala His Gly Leu Thr Pro
                275                 280                 285

Gln Gln Val Val Ala Ile Ala Ser Asn Asn Gly Gly Lys Gln Ala Leu
                290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Gly Gly Gly Lys Gln
                325                 330                 335

Ala Leu Glu Thr Val Gln Arg Leu Leu Pro Val Leu Cys Gln Ala His
                340                 345                 350

Gly Leu Thr Pro Gln Gln Val Val Ala Ile Ala Ser Asn Gly Gly Gly
                355                 360                 365

Lys Gln Ala Leu Glu Thr Val Gln Arg Leu Leu Pro Val Leu Cys Gln
                370                 375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
                420                 425                 430

Asn Ile Gly Gly Lys Gln Ala Leu Glu Thr Val Gln Ala Leu Leu Pro
                435                 440                 445

Val Leu Cys Gln Ala His Gly Leu Thr Pro Gln Gln Val Val Ala Ile
                450                 455                 460

Ala Ser Asn Asn Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
                485                 490                 495

Ala Ile Ala Ser His Asp Gly Gly Lys Gln Ala Leu Glu Thr Val Gln
                500                 505                 510

Arg Leu Leu Pro Val Leu Cys Gln Ala His Gly Leu Thr Pro Glu Gln
                515                 520                 525

Val Val Ala Ile Ala Ser His Asp Gly Gly Lys Gln Ala Leu Glu Thr
                530                 535                 540

Val Gln Arg Leu Leu Pro Val Leu Cys Gln Ala His Gly Leu Thr Pro
545                 550                 555                 560
```

Glu Gln Val Val Ala Ile Ala Ser His Asp Gly Gly Lys Gln Ala Leu
                565                 570                 575

Glu Thr Val Gln Arg Leu Leu Pro Val Leu Cys Gln Ala His Gly Leu
                580                 585                 590

Thr Pro Gln Gln Val Val Ala Ile Ala Ser Asn Asn Gly Gly Lys Gln
                595                 600                 605

Ala Leu Glu Thr Val Gln Arg Leu Leu Pro Val Leu Cys Gln Ala His
                610                 615                 620

Gly Leu Thr Pro Gln Gln Val Val Ala Ile Ala Ser Asn Asn Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
                660                 665                 670

Gly Gly Arg Pro Ala Leu Glu Ser Ile Val Ala Gln Leu Ser Arg Pro
                675                 680                 685

Asp Pro Ala Leu Ala Ala Leu Thr Asn Asp His Leu Val Ala Leu Ala
                690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
                740                 745                 750

Glu Leu Ile Glu Ile Ala Arg Asn Ser Thr Gln Asp Arg Ile Leu Glu
                755                 760                 765

Met Lys Val Met Glu Phe Phe Met Lys Val Tyr Gly Tyr Arg Gly Lys
                770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
                820                 825                 830

Glu Glu Asn Gln Thr Arg Asn Lys His Ile Asn Pro Asn Glu Trp Trp
                835                 840                 845

Lys Val Tyr Pro Ser Ser Val Thr Glu Phe Lys Phe Leu Phe Val Ser
                850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
                900                 905                 910

Arg Lys Phe Asn Asn Gly Glu Ile Asn Phe Ala Ala Asp
                915                 920                 925

<210> SEQ ID NO 8
<211> LENGTH: 925
<212> TYPE: PRT
<213> ORGANISM: artificial sequence
<220> FEATURE:
<223> OTHER INFORMATION: CD38 TALEN Right

<400> SEQUENCE: 8

```
Met Gly Asp Pro Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
                100                 105                 110

Pro Leu Gln Leu Asp Thr Gly Gln Leu Leu Lys Ile Ala Lys Arg Gly
                115                 120                 125

Gly Val Thr Ala Val Glu Ala Val His Ala Trp Arg Asn Ala Leu Thr
    130                 135                 140

Gly Ala Pro Leu Asn Leu Thr Pro Glu Gln Val Val Ala Ile Ala Ser
145                 150                 155                 160

Asn Ile Gly Gly Lys Gln Ala Leu Glu Thr Val Gln Ala Leu Leu Pro
                165                 170                 175

Val Leu Cys Gln Ala His Gly Leu Thr Pro Gln Gln Val Val Ala Ile
                180                 185                 190

Ala Ser Asn Asn Gly Gly Lys Gln Ala Leu Glu Thr Val Gln Arg Leu
                195                 200                 205

Leu Pro Val Leu Cys Gln Ala His Gly Leu Thr Pro Glu Gln Val Val
210                 215                 220

Ala Ile Ala Ser Asn Ile Gly Gly Lys Gln Ala Leu Glu Thr Val Gln
225                 230                 235                 240

Ala Leu Leu Pro Val Leu Cys Gln Ala His Gly Leu Thr Pro Gln Gln
                245                 250                 255

Val Val Ala Ile Ala Ser Asn Asn Gly Gly Lys Gln Ala Leu Glu Thr
                260                 265                 270

Val Gln Arg Leu Leu Pro Val Leu Cys Gln Ala His Gly Leu Thr Pro
                275                 280                 285

Glu Gln Val Val Ala Ile Ala Ser Asn Ile Gly Gly Lys Gln Ala Leu
290                 295                 300

Glu Thr Val Gln Ala Leu Leu Pro Val Leu Cys Gln Ala His Gly Leu
305                 310                 315                 320

Thr Pro Gln Gln Val Val Ala Ile Ala Ser Asn Asn Gly Gly Lys Gln
                325                 330                 335

Ala Leu Glu Thr Val Gln Arg Leu Leu Pro Val Leu Cys Gln Ala His
                340                 345                 350

Gly Leu Thr Pro Glu Gln Val Val Ala Ile Ala Ser His Asp Gly Gly
                355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415
```

-continued

```
Cys Gln Ala His Gly Leu Thr Pro Gln Gln Val Val Ala Ile Ala Ser
            420                 425                 430

Asn Asn Gly Gly Lys Gln Ala Leu Glu Thr Val Gln Arg Leu Leu Pro
            435                 440                 445

Val Leu Cys Gln Ala His Gly Leu Thr Pro Gln Gln Val Val Ala Ile
            450                 455                 460

Ala Ser Asn Asn Gly Gly Lys Gln Ala Leu Glu Thr Val Gln Arg Leu
465                 470                 475                 480

Leu Pro Val Leu Cys Gln Ala His Gly Leu Thr Pro Glu Gln Val Val
            485                 490                 495

Ala Ile Ala Ser His Asp Gly Gly Lys Gln Ala Leu Glu Thr Val Gln
            500                 505                 510

Arg Leu Leu Pro Val Leu Cys Gln Ala His Gly Leu Thr Pro Glu Gln
            515                 520                 525

Val Val Ala Ile Ala Ser Asn Ile Gly Gly Lys Gln Ala Leu Glu Thr
            530                 535                 540

Val Gln Ala Leu Leu Pro Val Leu Cys Gln Ala His Gly Leu Thr Pro
545                 550                 555                 560

Gln Gln Val Val Ala Ile Ala Ser Asn Asn Gly Gly Lys Gln Ala Leu
            565                 570                 575

Glu Thr Val Gln Arg Leu Leu Pro Val Leu Cys Gln Ala His Gly Leu
            580                 585                 590

Thr Pro Glu Gln Val Val Ala Ile Ala Ser His Asp Gly Gly Lys Gln
            595                 600                 605

Ala Leu Glu Thr Val Gln Arg Leu Leu Pro Val Leu Cys Gln Ala His
610                 615                 620

Gly Leu Thr Pro Glu Gln Val Val Ala Ile Ala Ser Asn Ile Gly Gly
625                 630                 635                 640

Lys Gln Ala Leu Glu Thr Val Gln Ala Leu Leu Pro Val Leu Cys Gln
            645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
            675                 680                 685

Asp Pro Ala Leu Ala Ala Leu Thr Asn Asp His Leu Val Ala Leu Ala
            690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
            725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
            755                 760                 765

Met Lys Val Met Glu Phe Phe Met Lys Val Tyr Gly Tyr Arg Gly Lys
            770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
            805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
```

```
                835                 840                 845
Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Leu Leu Ile
                885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925

<210> SEQ ID NO 9
<211> LENGTH: 925
<212> TYPE: PRT
<213> ORGANISM: artificial sequence
<220> FEATURE:
<223> OTHER INFORMATION: PD-1 TALEN Left 2

<400> SEQUENCE: 9

Met Gly Asp Pro Lys Lys Lys Arg Lys Val Ile Asp Ile Ala Asp Leu
1               5                   10                  15

Arg Thr Leu Gly Tyr Ser Gln Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
    130                 135                 140

Gly Ala Pro Leu Asn Leu Thr Pro Glu Gln Val Val Ala Ile Ala Ser
145                 150                 155                 160

Lys Leu Gly Gly Lys Gln Ala Leu Glu Thr Val Gln Ala Leu Leu Pro
                165                 170                 175

Val Leu Cys Gln Ala His Gly Leu Thr Pro Glu Gln Val Val Ala Ile
            180                 185                 190

Ala Ser His Asp Gly Gly Lys Gln Ala Leu Glu Thr Val Gln Arg Leu
        195                 200                 205

Leu Pro Val Leu Cys Gln Ala His Gly Leu Thr Pro Glu Gln Val Val
    210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Gln Gln
                245                 250                 255

Val Val Ala Ile Ala Ser Asn Gly Gly Gly Lys Gln Ala Leu Glu Thr
            260                 265                 270

Val Gln Arg Leu Leu Pro Val Leu Cys Gln Ala His Gly Leu Thr Pro
```

-continued

```
              275                 280                 285
Glu Gln Val Val Ala Ile Ala Ser His Asp Gly Gly Lys Gln Ala Leu
290                 295                 300
Glu Thr Val Gln Arg Leu Leu Pro Val Leu Cys Gln Ala His Gly Leu
305                 310                 315                 320
Thr Pro Gln Gln Val Ala Ile Ala Ser Asn Gly Gly Lys Gln
                325                 330                 335
Ala Leu Glu Thr Val Gln Arg Leu Leu Pro Val Leu Cys Gln Ala His
            340                 345                 350
Gly Leu Thr Pro Gln Gln Val Ala Ile Ala Ser Tyr Lys Gly Gly
            355                 360                 365
Lys Gln Ala Leu Glu Thr Val Gln Arg Leu Leu Pro Val Leu Cys Gln
370                 375                 380
Ala His Gly Leu Thr Pro Gln Gln Val Val Ala Ile Ala Ser Asn Gly
385                 390                 395                 400
Gly Gly Lys Gln Ala Leu Glu Thr Val Gln Arg Leu Leu Pro Val Leu
                405                 410                 415
Cys Gln Ala His Gly Leu Thr Pro Gln Gln Val Val Ala Ile Ala Ser
                420                 425                 430
Asn Asn Gly Gly Lys Gln Ala Leu Glu Thr Val Gln Arg Leu Leu Pro
            435                 440                 445
Val Leu Cys Gln Ala His Gly Leu Thr Pro Gln Gln Val Val Ala Ile
450                 455                 460
Ala Ser Asn Asn Gly Gly Lys Gln Ala Leu Glu Thr Val Gln Arg Leu
465                 470                 475                 480
Leu Pro Val Leu Cys Gln Ala His Gly Leu Thr Pro Gln Gln Val Val
                485                 490                 495
Ala Ile Ala Ser Asn Asn Gly Gly Lys Gln Ala Leu Glu Thr Val Gln
                500                 505                 510
Arg Leu Leu Pro Val Leu Cys Gln Ala His Gly Leu Thr Pro Gln Gln
            515                 520                 525
Val Val Ala Ile Ala Ser Asn Asn Gly Gly Lys Gln Ala Leu Glu Thr
530                 535                 540
Val Gln Arg Leu Leu Pro Val Leu Cys Gln Ala His Gly Leu Thr Pro
545                 550                 555                 560
Glu Gln Val Val Ala Ile Ala Ser His Asp Gly Gly Lys Gln Ala Leu
                565                 570                 575
Glu Thr Val Gln Arg Leu Leu Pro Val Leu Cys Gln Ala His Gly Leu
                580                 585                 590
Thr Pro Glu Gln Val Val Ala Ile Ala Ser His Asp Gly Gly Lys Gln
            595                 600                 605
Ala Leu Glu Thr Val Gln Arg Leu Leu Pro Val Leu Cys Gln Ala His
610                 615                 620
Gly Leu Thr Pro Glu Gln Val Val Ala Ile Ala Ser Asn Ile Gly Gly
625                 630                 635                 640
Lys Gln Ala Leu Glu Thr Val Gln Ala Leu Leu Pro Val Leu Cys Gln
                645                 650                 655
Ala His Gly Leu Thr Pro Gln Gln Val Val Ala Ile Ala Ser Asn Gly
                660                 665                 670
Gly Gly Arg Pro Ala Leu Glu Ser Ile Val Ala Gln Leu Ser Arg Pro
            675                 680                 685
Asp Pro Ala Leu Ala Ala Leu Thr Asn Asp His Leu Val Ala Leu Ala
690                 695                 700
```

Cys Leu Gly Gly Arg Pro Ala Leu Asp Ala Val Lys Gly Leu Gly
705                 710                 715                 720

Asp Pro Ile Ser Arg Ser Gln Leu Val Lys Ser Glu Leu Glu Lys
            725                 730                 735

Lys Ser Glu Leu Arg His Lys Leu Lys Tyr Val Pro His Glu Tyr Ile
        740                 745                 750

Glu Leu Ile Glu Ile Ala Arg Asn Ser Thr Gln Asp Arg Ile Leu Glu
        755                 760                 765

Met Lys Val Met Glu Phe Phe Met Lys Val Tyr Gly Tyr Arg Gly Lys
770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
            805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
            885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925

<210> SEQ ID NO 10
<211> LENGTH: 925
<212> TYPE: PRT
<213> ORGANISM: artificial sequence
<220> FEATURE:
<223> OTHER INFORMATION: B2M TALEN left

<400> SEQUENCE: 10

Met Gly Asp Pro Lys Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
130                 135                 140

```
Gly Ala Pro Leu Asn Leu Thr Pro Gln Gln Val Val Ala Ile Ala Ser
145                 150                 155                 160

Asn Asn Gly Gly Lys Gln Ala Leu Glu Thr Val Gln Arg Leu Leu Pro
            165                 170                 175

Val Leu Cys Gln Ala His Gly Leu Thr Pro Gln Gln Val Val Ala Ile
        180                 185                 190

Ala Ser Asn Asn Gly Gly Lys Gln Ala Leu Glu Thr Val Gln Arg Leu
    195                 200                 205

Leu Pro Val Leu Cys Gln Ala His Gly Leu Thr Pro Glu Gln Val Val
210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Ala His Gly Leu Thr Pro
        275                 280                 285

Gln Gln Val Val Ala Ile Ala Ser Asn Gly Gly Gly Lys Gln Ala Leu
290                 295                 300

Glu Thr Val Gln Arg Leu Leu Pro Val Leu Cys Gln Ala His Gly Leu
305                 310                 315                 320

Thr Pro Gln Gln Val Val Ala Ile Ala Ser Asn Gly Gly Lys Gln
                325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser Asn Ile Gly Gly
        355                 360                 365

Lys Gln Ala Leu Glu Thr Val Gln Ala Leu Leu Pro Val Leu Cys Gln
    370                 375                 380

Ala His Gly Leu Thr Pro Gln Gln Val Val Ala Ile Ala Ser Asn Asn
385                 390                 395                 400

Gly Gly Lys Gln Ala Leu Glu Thr Val Gln Arg Leu Leu Pro Val Leu
                405                 410                 415

Cys Gln Ala His Gly Leu Thr Pro Glu Gln Val Val Ala Ile Ala Ser
            420                 425                 430

His Asp Gly Gly Lys Gln Ala Leu Glu Thr Val Gln Arg Leu Leu Pro
        435                 440                 445

Val Leu Cys Gln Ala His Gly Leu Thr Pro Gln Gln Val Val Ala Ile
    450                 455                 460

Ala Ser Asn Gly Gly Gly Lys Gln Ala Leu Glu Thr Val Gln Arg Leu
465                 470                 475                 480

Leu Pro Val Leu Cys Gln Ala His Gly Leu Thr Pro Gln Gln Val Val
                485                 490                 495

Ala Ile Ala Ser Asn Asn Gly Gly Lys Gln Ala Leu Glu Thr Val Gln
            500                 505                 510

Arg Leu Leu Pro Val Leu Cys Gln Ala His Gly Leu Thr Pro Gln Gln
        515                 520                 525

Val Val Ala Ile Ala Ser Asn Gly Gly Gly Lys Gln Ala Leu Glu Thr
    530                 535                 540

Val Gln Arg Leu Leu Pro Val Leu Cys Gln Ala His Gly Leu Thr Pro
545                 550                 555                 560
```

Gln Gln Val Val Ala Ile Ala Ser Asn Asn Gly Gly Lys Gln Ala Leu
            565                 570                 575

Glu Thr Val Gln Arg Leu Leu Pro Val Leu Cys Gln Ala His Gly Leu
        580                 585                 590

Thr Pro Glu Gln Val Val Ala Ile Ala Ser His Asp Gly Gly Lys Gln
    595                 600                 605

Ala Leu Glu Thr Val Gln Arg Leu Leu Pro Val Leu Cys Gln Ala His
610                 615                 620

Gly Leu Thr Pro Gln Gln Val Val Ala Ile Ala Ser Asn Gly Gly Gly
625                 630                 635                 640

Lys Gln Ala Leu Glu Thr Val Gln Arg Leu Leu Pro Val Leu Cys Gln
                645                 650                 655

Ala His Gly Leu Thr Pro Gln Gln Val Val Ala Ile Ala Ser Asn Gly
            660                 665                 670

Gly Gly Arg Pro Ala Leu Glu Ser Ile Val Ala Gln Leu Ser Arg Pro
        675                 680                 685

Asp Pro Ala Leu Ala Ala Leu Thr Asn Asp His Leu Val Ala Leu Ala
    690                 695                 700

Cys Leu Gly Gly Arg Pro Ala Leu Asp Ala Val Lys Lys Gly Leu Gly
705                 710                 715                 720

Asp Pro Ile Ser Arg Ser Gln Leu Val Lys Ser Glu Leu Glu Glu Lys
                725                 730                 735

Lys Ser Glu Leu Arg His Lys Leu Lys Tyr Val Pro His Glu Tyr Ile
            740                 745                 750

Glu Leu Ile Glu Ile Ala Arg Asn Ser Thr Gln Asp Arg Ile Leu Glu
        755                 760                 765

Met Lys Val Met Glu Phe Phe Met Lys Val Tyr Gly Tyr Arg Gly Lys
    770                 775                 780

His Leu Gly Gly Ser Arg Lys Pro Asp Gly Ala Ile Tyr Thr Val Gly
785                 790                 795                 800

Ser Pro Ile Asp Tyr Gly Val Ile Val Asp Thr Lys Ala Tyr Ser Gly
                805                 810                 815

Gly Tyr Asn Leu Pro Ile Gly Gln Ala Asp Glu Met Gln Arg Tyr Val
            820                 825                 830

Glu Glu Asn Gln Thr Arg Asn Lys His Ile Asn Pro Asn Glu Trp Trp
        835                 840                 845

Lys Val Tyr Pro Ser Ser Val Thr Glu Phe Lys Phe Leu Phe Val Ser
    850                 855                 860

Gly His Phe Lys Gly Asn Tyr Lys Ala Gln Leu Thr Arg Leu Asn His
865                 870                 875                 880

Ile Thr Asn Cys Asn Gly Ala Val Leu Ser Val Glu Glu Leu Leu Ile
                885                 890                 895

Gly Gly Glu Met Ile Lys Ala Gly Thr Leu Thr Leu Glu Glu Val Arg
            900                 905                 910

Arg Lys Phe Asn Asn Gly Glu Ile Asn Phe Ala Ala Asp
        915                 920                 925

<210> SEQ ID NO 11
<211> LENGTH: 925
<212> TYPE: PRT
<213> ORGANISM: artificial sequence
<220> FEATURE:
<223> OTHER INFORMATION: B2M TALEN right

<400> SEQUENCE: 11

```
Met Gly Asp Pro Lys Lys Arg Lys Val Ile Asp Ile Ala Asp Leu
1               5                   10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
            35                  40                  45

Phe Thr His Ala His Ile Val Ala Leu Ser Gln His Pro Ala Ala Leu
    50                  55                  60

Gly Thr Val Ala Val Lys Tyr Gln Asp Met Ile Ala Ala Leu Pro Glu
65                  70                  75                  80

Ala Thr His Glu Ala Ile Val Gly Val Gly Lys Gln Trp Ser Gly Ala
                85                  90                  95

Arg Ala Leu Glu Ala Leu Leu Thr Val Ala Gly Glu Leu Arg Gly Pro
            100                 105                 110

Pro Leu Gln Leu Asp Thr Gly Gln Leu Leu Lys Ile Ala Lys Arg Gly
        115                 120                 125

Gly Val Thr Ala Val Glu Ala Val His Ala Trp Arg Asn Ala Leu Thr
    130                 135                 140

Gly Ala Pro Leu Asn Leu Thr Pro Glu Gln Val Val Ala Ile Ala Ser
145                 150                 155                 160

Asn Ile Gly Gly Lys Gln Ala Leu Glu Thr Val Gln Ala Leu Leu Pro
                165                 170                 175

Val Leu Cys Gln Ala His Gly Leu Thr Pro Gln Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Ala His Gly Leu Thr Pro Glu Gln Val Val
    210                 215                 220

Ala Ile Ala Ser His Asp Gly Gly Lys Gln Ala Leu Glu Thr Val Gln
225                 230                 235                 240

Arg Leu Leu Pro Val Leu Cys Gln Ala His Gly Leu Thr Pro Glu Gln
                245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Ala His Gly Leu Thr Pro
        275                 280                 285

Gln Gln Val Val Ala Ile Ala Ser Asn Gly Gly Gly Lys Gln Ala Leu
    290                 295                 300

Glu Thr Val Gln Arg Leu Leu Pro Val Leu Cys Gln Ala His Gly Leu
305                 310                 315                 320

Thr Pro Glu Gln Val Val Ala Ile Ala Ser His Asp Gly Gly Lys Gln
                325                 330                 335

Ala Leu Glu Thr Val Gln Arg Leu Leu Pro Val Leu Cys Gln Ala His
            340                 345                 350

Gly Leu Thr Pro Glu Gln Val Val Ala Ile Ala Ser His Asp Gly Gly
        355                 360                 365

Lys Gln Ala Leu Glu Thr Val Gln Arg Leu Leu Pro Val Leu Cys Gln
    370                 375                 380

Ala His Gly Leu Thr Pro Glu Gln Val Val Ala Ile Ala Ser Asn Ile
385                 390                 395                 400

Gly Gly Lys Gln Ala Leu Glu Thr Val Gln Ala Leu Leu Pro Val Leu
                405                 410                 415

Cys Gln Ala His Gly Leu Thr Pro Gln Gln Val Val Ala Ile Ala Ser
```

-continued

```
                420             425             430
Asn Asn Gly Gly Lys Gln Ala Leu Glu Thr Val Gln Arg Leu Leu Pro
        435                 440                 445
Val Leu Cys Gln Ala His Gly Leu Thr Pro Gln Gln Val Val Ala Ile
    450                 455                 460
Ala Ser Asn Asn Gly Gly Lys Gln Ala Leu Glu Thr Val Gln Arg Leu
465                 470                 475                 480
Leu Pro Val Leu Cys Gln Ala His Gly Leu Thr Pro Glu Gln Val Val
                485                 490                 495
Ala Ile Ala Ser His Asp Gly Gly Lys Gln Ala Leu Glu Thr Val Gln
            500                 505                 510
Arg Leu Leu Pro Val Leu Cys Gln Ala His Gly Leu Thr Pro Glu Gln
        515                 520                 525
Val Val Ala Ile Ala Ser His Asp Gly Gly Lys Gln Ala Leu Glu Thr
    530                 535                 540
Val Gln Arg Leu Leu Pro Val Leu Cys Gln Ala His Gly Leu Thr Pro
545                 550                 555                 560
Glu Gln Val Val Ala Ile Ala Ser Asn Ile Gly Gly Lys Gln Ala Leu
                565                 570                 575
Glu Thr Val Gln Ala Leu Leu Pro Val Leu Cys Gln Ala His Gly Leu
            580                 585                 590
Thr Pro Gln Gln Val Val Ala Ile Ala Ser Asn Asn Gly Gly Lys Gln
        595                 600                 605
Ala Leu Glu Thr Val Gln Arg Leu Leu Pro Val Leu Cys Gln Ala His
    610                 615                 620
Gly Leu Thr Pro Glu Gln Val Val Ala Ile Ala Ser Asn Ile Gly Gly
625                 630                 635                 640
Lys Gln Ala Leu Glu Thr Val Gln Ala Leu Leu Pro Val Leu Cys Gln
                645                 650                 655
Ala His Gly Leu Thr Pro Gln Gln Val Val Ala Ile Ala Ser Asn Gly
            660                 665                 670
Gly Gly Arg Pro Ala Leu Glu Ser Ile Val Ala Gln Leu Ser Arg Pro
        675                 680                 685
Asp Pro Ala Leu Ala Ala Leu Thr Asn Asp His Leu Val Ala Leu Ala
    690                 695                 700
Cys Leu Gly Gly Arg Pro Ala Leu Asp Ala Val Lys Lys Gly Leu Gly
705                 710                 715                 720
Asp Pro Ile Ser Arg Ser Gln Leu Val Lys Ser Glu Leu Glu Glu Lys
                725                 730                 735
Lys Ser Glu Leu Arg His Lys Leu Lys Tyr Val Pro His Glu Tyr Ile
            740                 745                 750
Glu Leu Ile Glu Ile Ala Arg Asn Ser Thr Gln Asp Arg Ile Leu Glu
        755                 760                 765
Met Lys Val Met Glu Phe Phe Met Lys Val Tyr Gly Tyr Arg Gly Lys
    770                 775                 780
His Leu Gly Gly Ser Arg Lys Pro Asp Gly Ala Ile Tyr Thr Val Gly
785                 790                 795                 800
Ser Pro Ile Asp Tyr Gly Val Ile Val Asp Thr Lys Ala Tyr Ser Gly
                805                 810                 815
Gly Tyr Asn Leu Pro Ile Gly Gln Ala Asp Glu Met Gln Arg Tyr Val
            820                 825                 830
Glu Glu Asn Gln Thr Arg Asn Lys His Ile Asn Pro Asn Glu Trp Trp
        835                 840                 845
```

```
Lys Val Tyr Pro Ser Ser Val Thr Glu Phe Lys Phe Leu Phe Val Ser
            850                 855                 860
Gly His Phe Lys Gly Asn Tyr Lys Ala Gln Leu Thr Arg Leu Asn His
865                 870                 875                 880
Ile Thr Asn Cys Asn Gly Ala Val Leu Ser Val Glu Glu Leu Leu Ile
                885                 890                 895
Gly Gly Glu Met Ile Lys Ala Gly Thr Leu Thr Leu Glu Glu Val Arg
            900                 905                 910
Arg Lys Phe Asn Asn Gly Glu Ile Asn Phe Ala Ala Asp
            915                 920                 925

<210> SEQ ID NO 12
<211> LENGTH: 576
<212> TYPE: PRT
<213> ORGANISM: artificial sequence
<220> FEATURE:
<223> OTHER INFORMATION: CD22 CAR

<400> SEQUENCE: 12

Met Ala Leu Pro Val Thr Ala Leu Leu Leu Pro Leu Ala Leu Leu Leu
1               5                   10                  15
His Ala Ala Arg Pro Gly Gly Gly Ser Cys Pro Tyr Ser Asn Pro
            20                  25                  30
Ser Leu Cys Ser Gly Gly Gly Ser Gly Gly Gly Ser Gln Val
            35                  40                  45
Gln Leu Gln Gln Ser Gly Pro Gly Leu Val Lys Pro Ser Gln Thr Leu
    50                  55                  60
Ser Leu Thr Cys Ala Ile Ser Gly Asp Ser Val Ser Ser Asn Ser Ala
65                  70                  75                  80
Ala Trp Asn Trp Ile Arg Gln Ser Pro Ser Arg Gly Leu Glu Trp Leu
                85                  90                  95
Gly Arg Thr Tyr Tyr Arg Ser Lys Trp Tyr Asn Asp Tyr Ala Val Ser
            100                 105                 110
Val Lys Ser Arg Ile Thr Ile Asn Pro Asp Thr Ser Lys Asn Gln Phe
            115                 120                 125
Ser Leu Gln Leu Asn Ser Val Thr Pro Glu Asp Thr Ala Val Tyr Tyr
    130                 135                 140
Cys Ala Arg Glu Val Thr Gly Asp Leu Glu Asp Ala Phe Asp Ile Trp
145                 150                 155                 160
Gly Gln Gly Thr Met Val Thr Val Ser Ser Gly Gly Gly Gly Ser Gly
                165                 170                 175
Gly Gly Gly Ser Gly Gly Gly Gly Ser Asp Ile Gln Met Thr Gln Ser
            180                 185                 190
Pro Ser Ser Leu Ser Ala Ser Val Gly Asp Arg Val Thr Ile Thr Cys
            195                 200                 205
Arg Ala Ser Gln Thr Ile Trp Ser Tyr Leu Asn Trp Tyr Gln Gln Arg
    210                 215                 220
Pro Gly Lys Ala Pro Asn Leu Leu Ile Tyr Ala Ala Ser Ser Leu Gln
225                 230                 235                 240
Ser Gly Val Pro Ser Arg Phe Ser Gly Arg Gly Ser Gly Thr Asp Phe
                245                 250                 255
Thr Leu Thr Ile Ser Ser Leu Gln Ala Glu Asp Phe Ala Thr Tyr Tyr
            260                 265                 270
Cys Gln Gln Ser Tyr Ser Ile Pro Gln Thr Phe Gly Gln Gly Thr Lys
            275                 280                 285
```

```
Leu Glu Ile Lys Ser Asp Pro Gly Ser Gly Gly Gly Ser Cys Pro
    290             295             300
Tyr Ser Asn Pro Ser Leu Cys Ser Gly Gly Gly Gly Ser Glu Leu Pro
305             310             315             320
Thr Gln Gly Thr Phe Ser Asn Val Ser Thr Asn Val Ser Pro Ala Lys
            325             330             335
Pro Thr Thr Thr Ala Cys Pro Tyr Ser Asn Pro Ser Leu Cys Ala Pro
            340             345             350
Thr Thr Thr Pro Ala Pro Arg Pro Pro Thr Pro Ala Pro Thr Ile Ala
            355             360             365
Ser Gln Pro Leu Ser Leu Arg Pro Glu Ala Cys Arg Pro Ala Ala Gly
    370             375             380
Gly Ala Val His Thr Arg Gly Leu Asp Phe Ala Cys Asp Ile Tyr Ile
385             390             395             400
Trp Ala Pro Leu Ala Gly Thr Cys Gly Val Leu Leu Leu Ser Leu Val
            405             410             415
Ile Thr Leu Tyr Cys Arg Arg Gly Arg Lys Lys Leu Leu Tyr Ile Phe
            420             425             430
Lys Gln Pro Phe Met Arg Pro Val Gln Thr Thr Gln Glu Glu Asp Gly
    435             440             445
Cys Ser Cys Arg Phe Pro Glu Glu Glu Glu Gly Gly Cys Glu Leu Arg
    450             455             460
Val Lys Phe Ser Arg Ser Ala Asp Ala Pro Ala Tyr Gln Gln Gly Gln
465             470             475             480
Asn Gln Leu Tyr Asn Glu Leu Asn Leu Gly Arg Arg Glu Glu Tyr Asp
            485             490             495
Val Leu Asp Lys Arg Arg Gly Arg Asp Pro Glu Met Gly Gly Lys Pro
            500             505             510
Arg Arg Lys Asn Pro Gln Glu Gly Leu Tyr Asn Glu Leu Gln Lys Asp
    515             520             525
Lys Met Ala Glu Ala Tyr Ser Glu Ile Gly Met Lys Gly Glu Arg Arg
    530             535             540
Arg Gly Lys Gly His Asp Gly Leu Tyr Gln Gly Leu Ser Thr Ala Thr
545             550             555             560
Lys Asp Thr Tyr Asp Ala Leu His Met Gln Ala Leu Pro Pro Arg Glu
            565             570             575
```

SEQUENTIAL GENE EDITING IN PRIMARY IMMUNE CELLS

FIELD OF THE INVENTION

The invention pertains to the field of adaptive cell immunotherapy. It aims at reducing the occurrence of translocations and cell deaths when several specific endonuclease reagents are used altogether to genetically modify primary immune cells at different genetic loci. The method of the invention allows to yield safer immune primary cells harboring several genetic modifications, such as triple or quadruple gene inactivated cells, from populations or subpopulations of cells originating from a single donor or patient, for their subsequent use in therapeutic treatments.

BACKGROUND OF THE INVENTION

The potential of gene editing in various therapies has long been envisioned by the applicant (WO2004067753), especially in the field of cell therapy, where immune cells can be genetically modified ex-vivo and then reintroduced into patients, as already described, for instance, in U.S. Pat. No. 8,921,332.

Since the emergence of the first programmable sequence-specific reagents by the turn of the century, initially referred to as Meganucleases [Smith et al. (2006) A combinatorial approach to create artificial homing endonucleases cleaving chosen sequences. *Nucl. Acids Res.* 34 (22):e149.], endonucleases reagents have rapidly evolved, offering improved specificity, safety and reliability. In particular, TALE-nucleases (WO2011072246), which are fusions of a TALE binding domain with a cleavage catalytic domain have been successfully applied to primary immune cells, in particular T-cells from peripheral blood mononuclear cells (PBMC). Such TALE-nucleases, marketed under the name TALEN®, are currently used to simultaneously inactivate gene sequences in T-cells originating from donors, in particular to produce allogeneic therapeutic T-Cells, in which the genes encoding TCR (T-cell receptor) and CD52 are disrupted. These cells can be endowed with chimeric antigen receptors (CAR) or recombinant TCR for treating cancer patients (US2013/0315884). TALE-nucleases are very specific reagents because they need to bind DNA by pairs under obligatory heterodimeric form to obtain dimerization of the cleavage domain Fok-1. Left and right heterodimer members each recognizes a different nucleic sequences of about 14 to 20 bp, together spanning target sequences of 30 to 50 bp overall specificity.

More recently, further endonucleases reagents have been developed based on the components of the type II prokaryotic CRISPR (Clustered Regularly Interspaced Short palindromic Repeats) adaptive immune system of the bacteria *S. pyogenes*. This multi-component system referred to as RNA-guided nuclease system [Gasiunas, Barrangou et al. (2012) Cas9-crRNA ribonucleoprotein complex mediates specific DNA cleavage for adaptive immunity in bacteria; PNAS 109(39):E2579-E2586]; Doudna, J. Charpentier E. (2014) The new frontier of genome engineering with CRISPR-Cas9 *Science* 346 (6213):1258096], involves members of Cas9 or Cpf1 [Zetsche et al. (2015). Cpf1 is a single RNA-guided endonuclease that provides immunity in bacteria and can be adapted for genome editing in mammalian cells. *Cell* 163:759-771] endonuclease families coupled with a guide RNA molecules that have the ability to drive said nuclease to some specific genome sequences. Such programmable RNA-guided endonucleases are easy to produce because the cleavage specificity is determined by the sequence of the RNA guide, which can be easily designed and cheaply produced. The specificity of CRISPR/Cas9 although stands on shorter sequences than TAL-nucleases of about 10 pb, which must be located near a particular motif (PAM) in the targeted genetic sequence.

Other endonuclease systems derived from homing endonucleases (ex: I-OnuI, or I-CreI), combined or not with TAL-nuclease (ex: MegaTAL) or zing-finger nucleases have also proven specificity, but with less efficiency so far.

Various proofs of concept of the efficiency and safety of the above specific endonuclease reagents have been reported in human cells in-vitro or ex-vivo, but the co-delivery into the same cells of sequence specific reagents acting on different loci has still to be carefully considered as a potential factor of off-site mutations, large genomic deletions and translocations inherent to the DNA repair mechanisms (Poirot et al. (2015) Multiplex Genome-Edited T-cell Manufacturing Platform for "Off-the-Shelf" Adoptive T-cell Immunotherapies *Cancer Res.* 75: 3853-64).

In parallel, novel specificities have been conferred to immune cells through the genetic transfer of transgenic T-cell receptors or so-called chimeric antigen receptors (CARs) (Jena et al. (2010) Redirecting T-cell specificity by introducing a tumor-specific chimeric antigen receptor. *Blood*. 116:1035-1044). CARs are recombinant receptors comprising a targeting moiety that is associated with one or more signaling domains in a single fusion molecule. In general, the binding moiety of a CAR consists of an antigen-binding domain of a single-chain antibody (scFv), comprising the light and heavy variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), ICOS and 4-1BB (CD137) have been added alone (second generation) or in combination (third generation) to enhance survival and increase proliferation of CAR modified T cells. CARs, as well as the expression of recombinant TCRs, have successfully allowed T cells to be redirected against antigens expressed by tumor cells from various malignancies including lymphomas and solid tumors.

Recently engineered T-cells disrupted in their T-cell receptor (TCR) using TALE-nucleases, endowed with chimeric antigen receptor (CAR) targeting CD19 malignant antigen, referred to as "UCART19" product, have shown therapeutic potential in at least two infants who had refractory leukemia (Leukaemia success heralds wave of gene-editing therapies (2015) *Nature* 527:146-147). To obtain such UCART19 cells, the TALE-nuclease was transiently expressed into the cells upon electroporation of capped mRNA to operate TCR gene disruption, whereas a cassette encoding the chimeric antigen receptor (CAR CD19) was introduced randomly into the genome using a retroviral vector.

In this later approach, the steps of gene inactivation and of expressing the chimeric antigen receptor are independently performed after inducing activation of the T-Cell "ex-vivo".

However, engineering primary immune cells is not without any consequences on the growth/physiology of such cells. In particular one major challenge is to avoid cells exhaustion/anergy that significantly reduces their immune reaction and life span. This is more likely to happen when the cells are artificially activated ahead of their infusion into the patient. It is also the case when a cell is endowed with a CAR that is too reactive.

The introduction of the polynucleotides expressing recombinant receptors into those cells, through an independent step of viral transduction, also has an impact on the overall production process.

The inventors have explored safer means for ex-vivo delivery of endonucleases reagents into primary cells with the requirements that said cells (1) are modified at different genetic loci, (2) not bearing too many translocations, (3) produced in sufficient number to enable treating at least a hundred patients, and (4) produced in a limited time frame of less than 30 days to avoid exhaustion of the cells. They came up with the invention as described herein, where sequential gene editing is performed instead of multiplexing gene editing. Surprisingly, this occurred to be less destructive to the cells, resulting into higher quality primary immune cells.

This invention paves the way to standard and affordable adoptive immune cell therapy treatments.

SUMMARY OF THE INVENTION

The present invention is drawn to a method of sequential gene editing aiming to improve the genetic modification of primary human cells, especially immune cells originating from individual donors or patients.

Primary immune cells, in particular T-cells or NK cells, have a limited life span, and although they can be expanded and activated ex-vivo by methods known in the art [Rasmussen A. M. et al. (2010) Ex-vivo expansion protocol for human tumor specific T cells for adoptive T cell therapy. *Journal of Immunological Methods* 355:52-60], their immune reactivity tends to reduce over time. They can also get exhausted from the moment they are collected from a donor to the moment they are reintroduced in-vivo to track down and eliminate malignant or infected cells into the patient.

Gene editing techniques using nucleotide sequence-specific reagents, such as rare-cutting endonucleases, have become the state of the art for the introduction of genetic modifications into primary cells. However, when such endonucleases are used to cleave target sequences simultaneously at different loci, the risk of inter- or intra-chromosomal translocations increases significantly, which concur to a higher risk of unwanted genetic recombination or off-site mutations.

To overcome this drawback and minimize adverse genome effects, the inventors have applied a safer approach, where gene editing is sequentially applied, in particular through several rounds of electroporation. To their surprise, sequential gene editing resulted into cells of higher quality and even into an increase of the yield of the engineered cells modified at different loci, as compared to multiplexing gene editing (i.e. gene editing performed simultaneously at different loci).

The present invention thus primarily concerns a method comprising one or several steps of:

Providing at least one primary immune cell from a culture or a blood sample, such as from peripheral blood mononuclear cells (PBMCs);

Subjecting said cell to a step of gene editing, where a first set of sequence-specific reagent(s) is introduced into said cell;

Cultivating said cell to enable said first sequence-specific reagent to stably modifying its genome at a first locus, Subjecting said cell to at least a second gene editing step to introduce at least a second set of sequence-specific reagent(s) into said cell, and optionally Cultivating said cell to enable said second sequence-specific reagent to stably modifying its genome at said second locus.

According to a preferred embodiment, the first, second and any subsequent sequence-specific reagents are introduced into said cell by electroporation, so that the method of the invention comprises:

a) Subjecting the immune cells to a first electroporation to introduce at least a first sequence-specific reagent into said immune cell;

b) cultivating said immune cell to enable said first sequence-specific reagent to modify its genome at a first locus, c) submitting said cell to at least a second electroporation to introduce at least a second sequence-specific reagent into said cell, and optionally d) cultivating said immune cell to enable said second sequence-specific reagent to modify its genome at said second locus.

Several strategies may be applied when applying the sequential gene editing of the present invention to obtain immune cells with higher recovery, better activation, persistence or therapeutic efficiency. As an example, the first electroporation step can be performed in view of editing or modifying a gene, in such a way that the cell will better expand or get more permissive to the subsequent modification steps.

As another example, the first step of gene editing can be performed on a receptor or surface protein, such as TCR. The TCR negative cells obtained by this first step can be purified by removal of the cells remaining TCR positive, such that said TCR negative cells can be cultivated and then subjected to a second step of gene editing, for instance to make them resistant to a chemotherapy drug. The resulting population of cells in which the second gene editing has been achieved, can then be enriched in TCR negative drug resistant cells by culture in a medium containing said chemotherapy drug.

Several examples are developed herein showing that, although deemed more destructive, the successive gene editing steps surprisingly contribute to improve the yield and therapeutic potential of the engineered immune cells.

The invention is drawn to the methods, but also to the new gene edited cells obtainable by these methods, especially new triple and quadruple gene inactivated immune cells, as well as the population of cells resulting thereof, which are useful for the preparation of therapeutic compositions.

The present invention may be further summarized by the following items:

1) A method for introducing genetic modifications at different loci of a primary immune cell, comprising the sequential steps of:

a) subjecting said primary immune cell to a first electroporation step to introduce at least a first sequence-specific reagent into said immune cell;

b) cultivating said primary immune cell thereby enabling said first sequence-specific reagent to modify its genome at a first locus, c) subjecting said primary immune to at least a second electroporation step to introduce at least a second sequence-specific reagent into said cell, d) cultivating and expanding said primary immune thereby enabling said second sequence-specific reagent to modify its genome at said second locus.
2) The method according to item 1, wherein the primary immune cell is cultivated in step b) from 12 to 72 hours, preferably from 24 to 48 hours.
3) The method according to item 1, wherein a purification step is performed between step b) and c) relying on a product resulting from the expression or the deletion of the gene that is modified at least at said first locus.
4) The method according to any one of items 1 to 3, wherein steps a) to d) are performed within 240 hours, preferably within 120 hours, more preferably within 96 hours, even more preferably within 72 hours.
5) The method according to any one of items 1 to 4, wherein said method comprises at least one further step of submitting said primary immune cell to a third electroporation step to introduce at least a third sequence-specific reagent into said cell.
6) The method according to item 1, wherein said first and/or second sequence-specific reagent is a polynucleotide or polypeptide encoding a rare-cutting endonuclease, a subunit thereof, or a conjugate of both a polynucleotide and a polypeptide.
7) The method according to item 2, wherein said first and/or second sequence-specific reagent is a polynucleotide or polypeptide encoding a rare-cutting endonuclease selected from programmable RNA or DNA guided endonuclease, TALEN, ZFN or a homing endonuclease.
8) The method according to item 3, wherein said first and/or second sequence-specific reagent is a conjugate of RNA guide and a Cas9 or Cpf1 polypeptide.
9) The method according to item 1, wherein said first and/or second sequence-specific reagent is an interference RNA (RNAi) or a polynucleotide encoding same.
10) The method according to item 1, wherein a transduction step is introduced between b) and c) with a retroviral or lentiviral vector.
11) The method according to item 10, wherein said transduction step involves an integrative lentiviral or retroviral vector for stable expression of a transgene.
12) The method according to item 11, wherein said transgene encodes a Chimeric Antigen Receptor (CAR).
13) The method according to item 10, wherein said transduction step involves a non-integrative viral vector.
14) The method according to item 13, wherein said non integrative viral vector is used as a template for homologous recombination or NHEJ integration of said transgene into the immune cell's genome.
15) The method according to item 10, wherein said first sequence-specific reagent is acting on a genomic sequence that facilitates the transduction step.
16) The method according to any one of items 1 to 15, wherein said first sequence-specific reagent is acting on a genomic sequence that facilitates the genetic modification of step d).
17) The method according to any one of items 1 to 16, wherein step b) is performed below about 35° C., preferably at about 30° C.
18) The method according to any one of items 1 to 17, wherein said immune cell is a T-cell.
19) The method according to item 18, comprising a preliminary step of activating the primary T-cell by signal transduction.
20) The method according to item 18 or 19, wherein said first sequence-specific reagent permanently reduces or prevents expression of TCR by the primary T-cell.
21) The method according to any one of items 1 to 20, wherein said first or second sequence-specific reagent permanently reduces or prevents expression of at least one gene encoding an immune checkpoint.
22) The method according to item 21, wherein said at least one gene encoding an immune checkpoint is selected from PD1, CTLA4, PPP2CA, PPP2CB, PTPN6, PTPN22, PDCD1, LAG3, HAVCR2, BTLA, CD160, TIGIT, CD96, CRTAM, LAIR1, SIGLEC7, SIGLEC9, CD244, TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, MORA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3.
23) The method according to any one of items 1 to 20, wherein said first or second sequence-specific reagent permanently confers resistance of said primary immune cell against drugs or immune depleting agents.
24) The method according to item 23, wherein said resistance is conferred by inactivating a gene expressing CD52, dCK, GGH or HPRT.
25) The method according to any one of items 1 to 24, wherein a final step of purification is performed relying on a at least one product resulting from the expression or the deletion of one gene that is modified at said first and/or second and/or third locus.
26) A population of primary TCR negative T-cells resulting from a single donor obtainable according to the method according to any one of items 1 to 25, comprising at least two subpopulations of T-cells selected from:
TCR negative and PD1 negative,
TCR negative and CD52 negative,
TCR negative and CTLA4 negative,
TCR negative and dCK negative,
TCR negative and GGH negative,
TCR negative and HPRT negative, and
TCR negative and β2m negative.
27) A population of primary TCR negative T-cells originating from a single donor, wherein at least 20%, preferably 30%, more preferably 50% of the cells in said population have been modified using sequence-specific reagents in at least three different loci.
28) A pharmaceutical composition comprising a population of primary T cells according to any one of items 26 or 27.

BRIEF DESCRIPTION OF THE FIGURES AND TABLES

FIG. 1: Examples of genes and cell functions which can be sequentially modified by gene editing according to the method of the present invention to produce engineered allogeneic primary immune T-cells. Arrows within the cell represents the various genetic loci that can be inactivated by the sequence specific nuclease reagent introduced into the T-cells.

Figure 2:
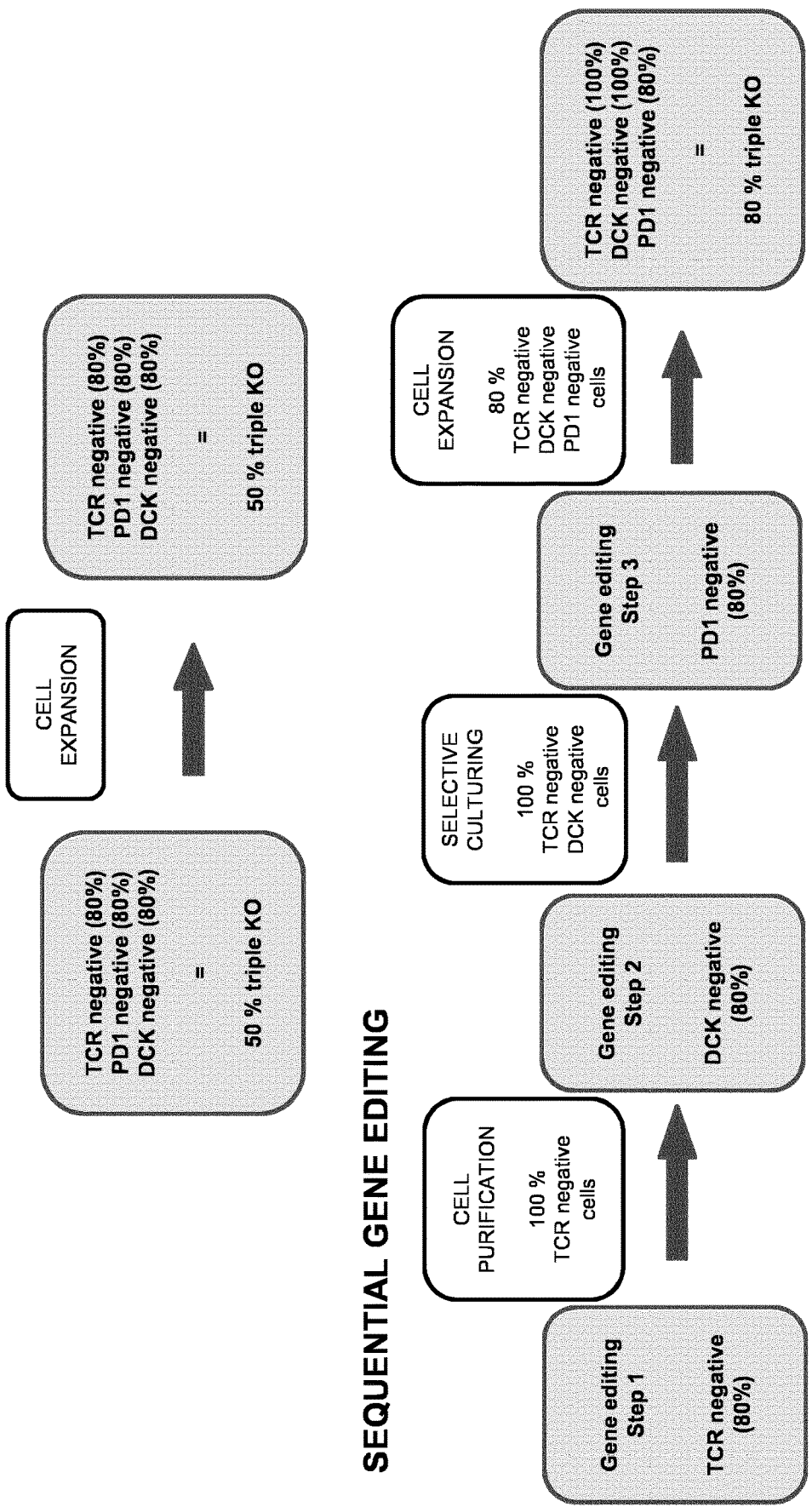

FIG. 2: Rationale for the sequential gene editing according to the present invention versus the multiplexing gene editing from the prior art in terms of yielding primary immune cells stacking mutations at three different loci, such as genes encoding TCR, PD1 and DCK. The method of the present invention ends up with a population of immune cells where at least 80% of the cells are triple mutants. By contrast, with the same reagent efficiency, simultaneous gene editing amounts about 50% of triple mutants. Upon cell expansion, this proportion should not much increase in the population, if not be decreasing.

Figure 3:
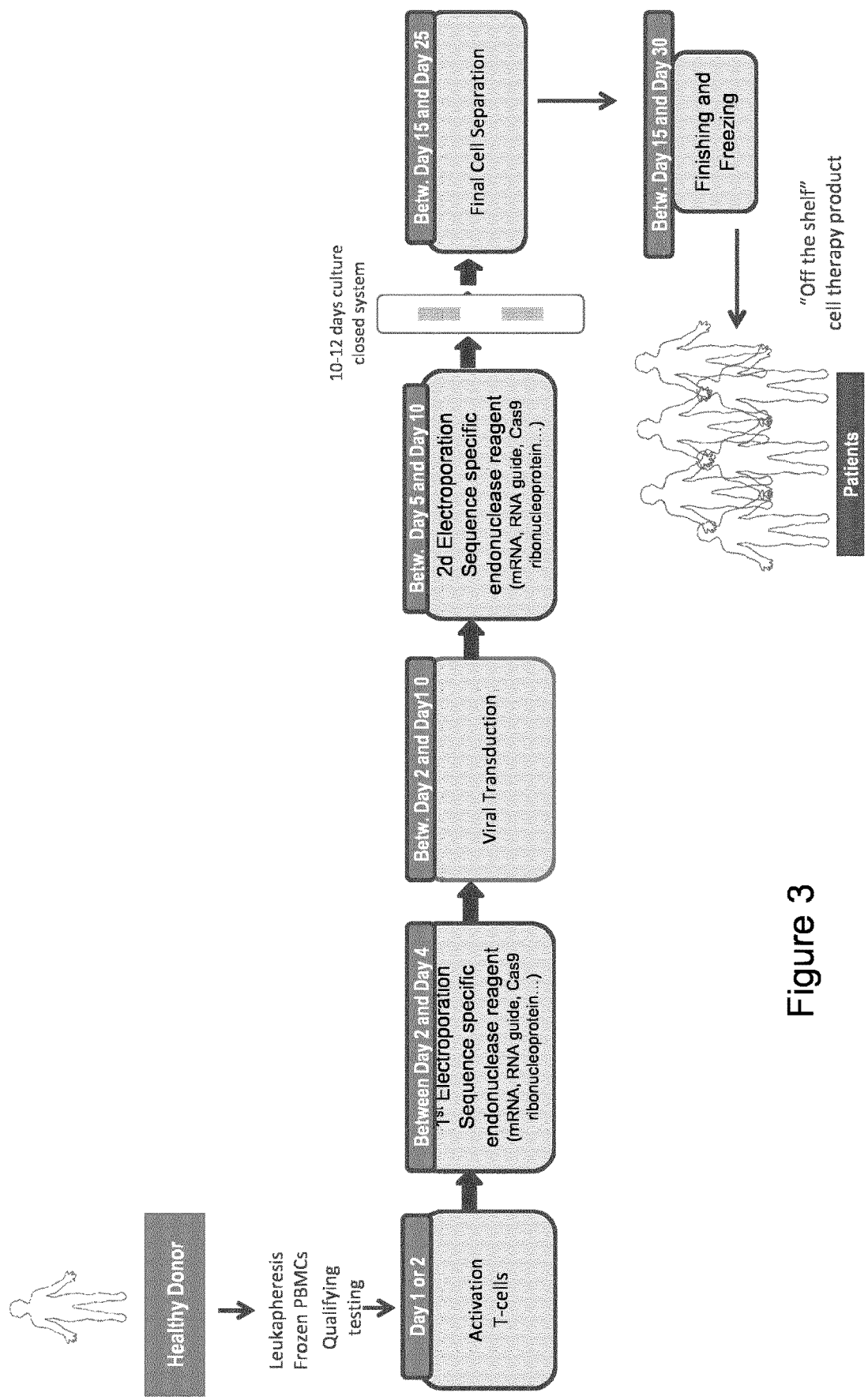

FIG. 3: Schematic representation of one embodiment of the method according to the invention, where a viral transduction step is performed between two electroporation gene editing steps. The viral transduction is preferably performed after a cell sorting step where the cells modified by the first gene editing modifications are purified. This cell sorting step reduces the overall number of cells, thereby reducing the number of viral particles to be used for the viral transduction. This can be advantageous, for instance, when TCR is first inactivated, to follow-up with stable viral transduction and expression of the CAR. Subsequent gene editing step can then be carried out to make the cells resistant to a drug. In such a situation, culturing or expanding the cells in a medium containing the drug allows the selection of the cells that are both TCR negative and drug resistant in view of their therapeutic use.

Figure 4:
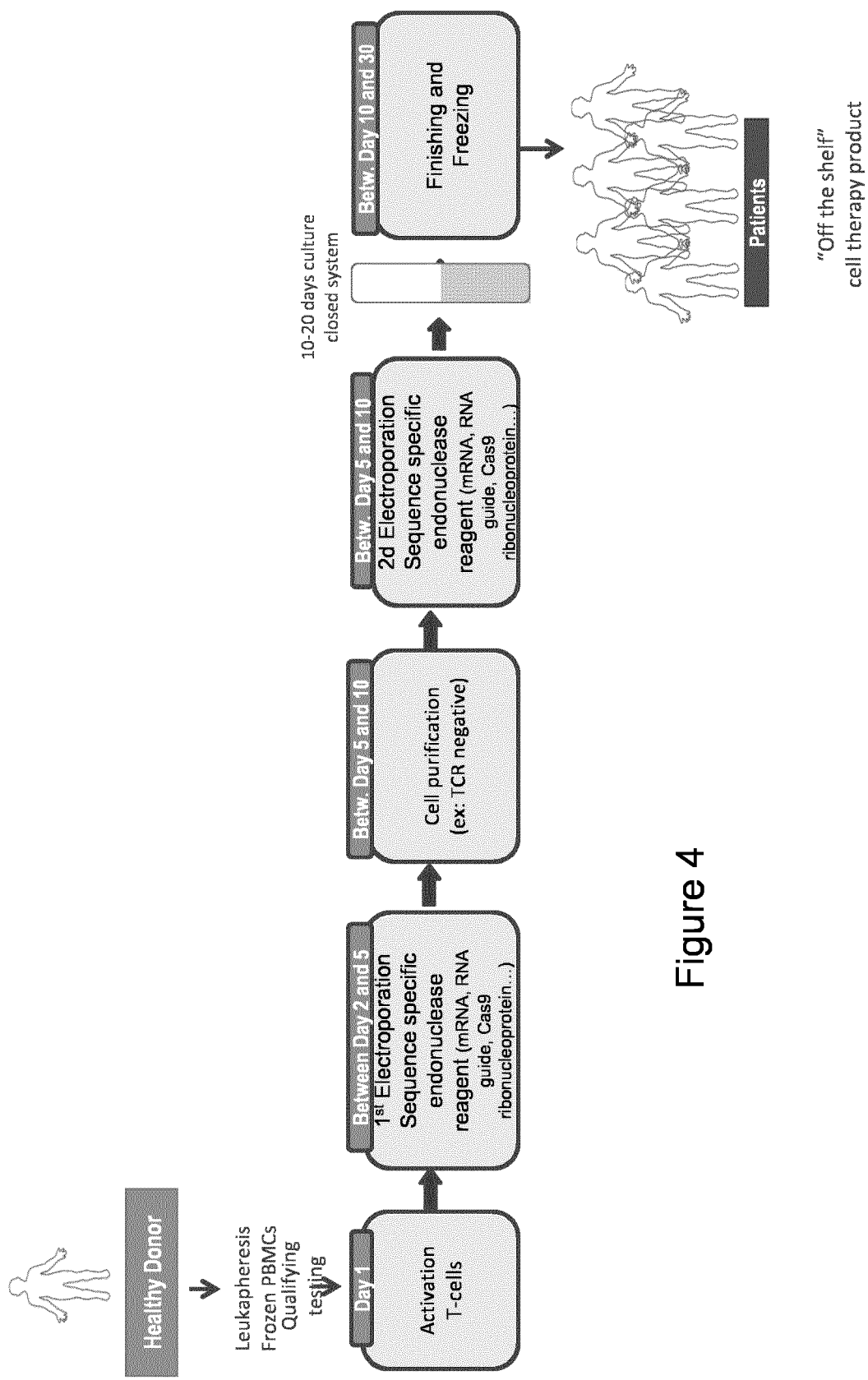

FIG. 4: Schematic representation of one embodiment of the method of the invention, wherein a cell sorting step is performed between the two electroporation gene editing steps.

Figure 5:
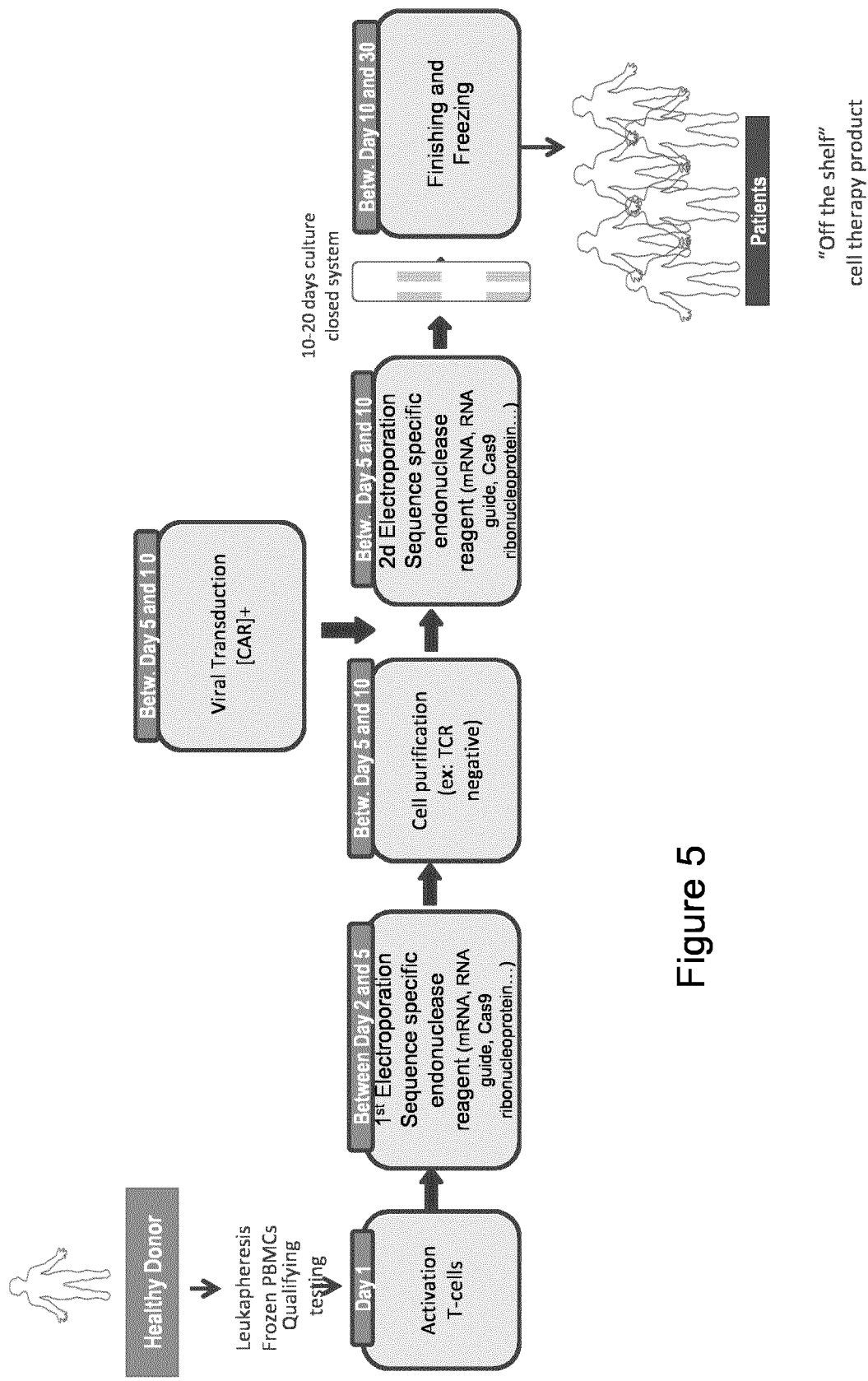

FIG. 5: Schematic representation of one embodiment of the method of the invention, wherein a cell sorting step plus a viral transduction is performed between the two electroporation gene editing steps.

Figure 6:
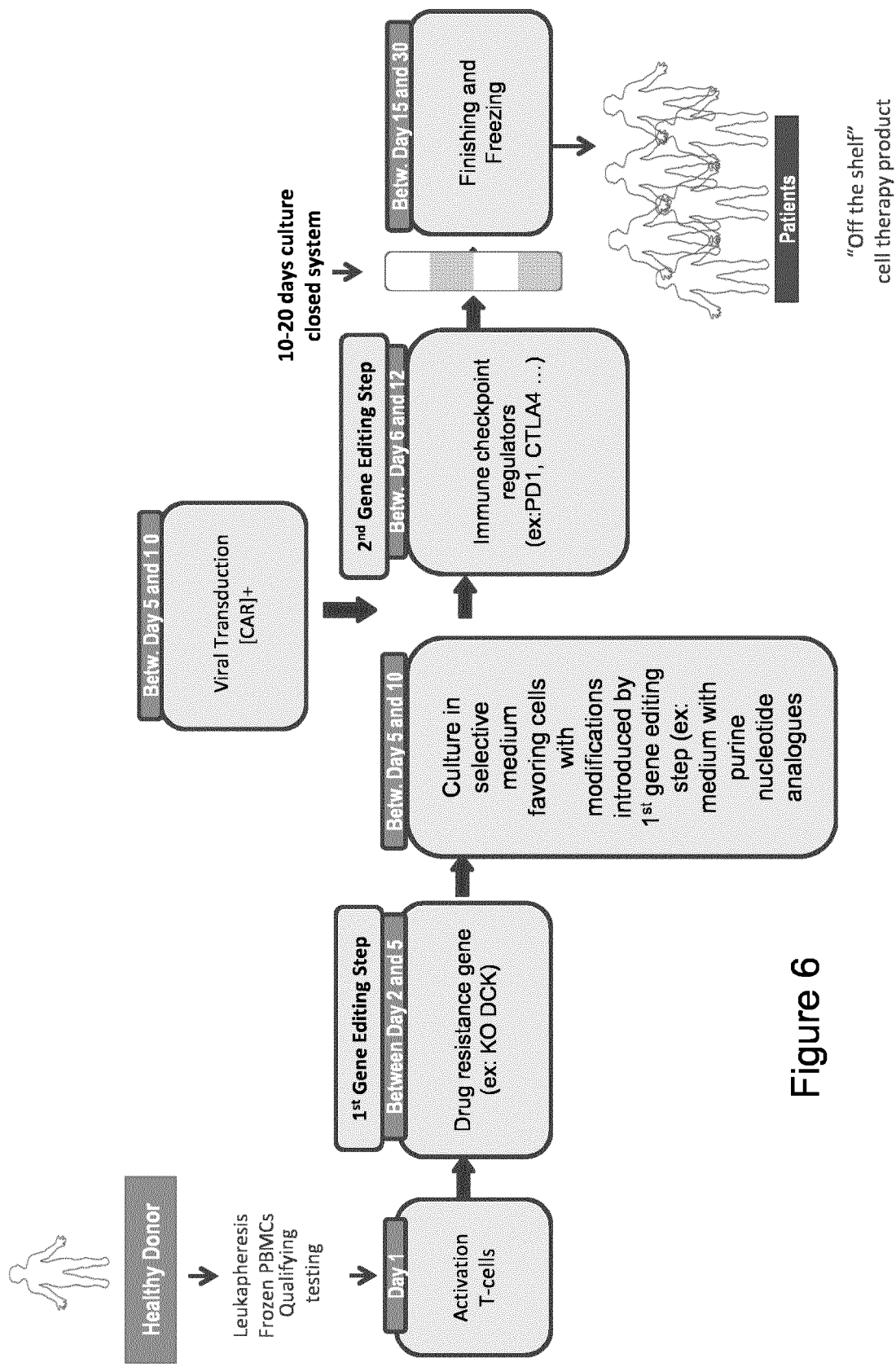

FIG. 6: Schematic representation of one embodiment of the method according to the invention, where a culture step in a selective medium is performed between two electroporation gene editing steps, to select the cells that have been made resistant to a compound as per the first gene modification. This culture step increases the number of cells that are eventually modified at multiple loci after the second gene editing step. This approach can be applied to produce drug resistant CAR positive T-cells, that are further gene edited to be more active (inactivation of a locus inhibiting T-cell activation/cytotoxicity, such as PD1 and/or CTLA4), especially in a context of an autologous treatment where the T-cells (eg: Tumor Infiltrating Lymphocytes (TIL)) are collected from a patient, engineered and re-infused to said patient.

Figure 7:
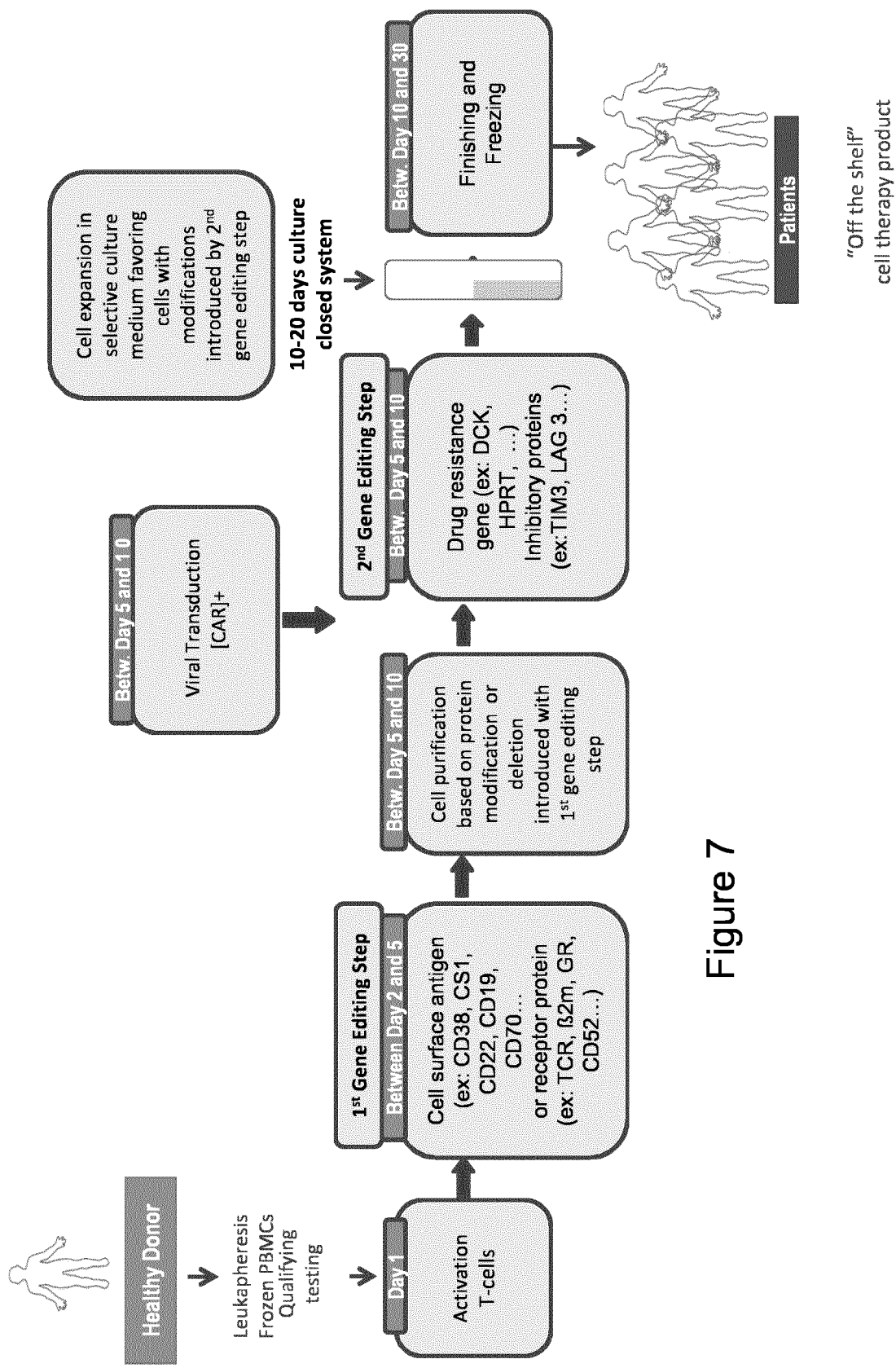

FIG. 7: Schematic representation of one embodiment of the method according to the invention, where the first gene editing step is performed in a gene coding or regulating the expression of a surface antigen and the second gene editing step is performed in a gene coding or regulating the expression of a product that is not a surface antigen. A cell separation step is performed between the two gene editing steps to enrich the cells allowed to pass to the second gene editing step. Optionally, the second gene editing step is followed by a culture step in a selective medium to favor/select expansion of the cells bearing the second gene editing.

Figure 8:
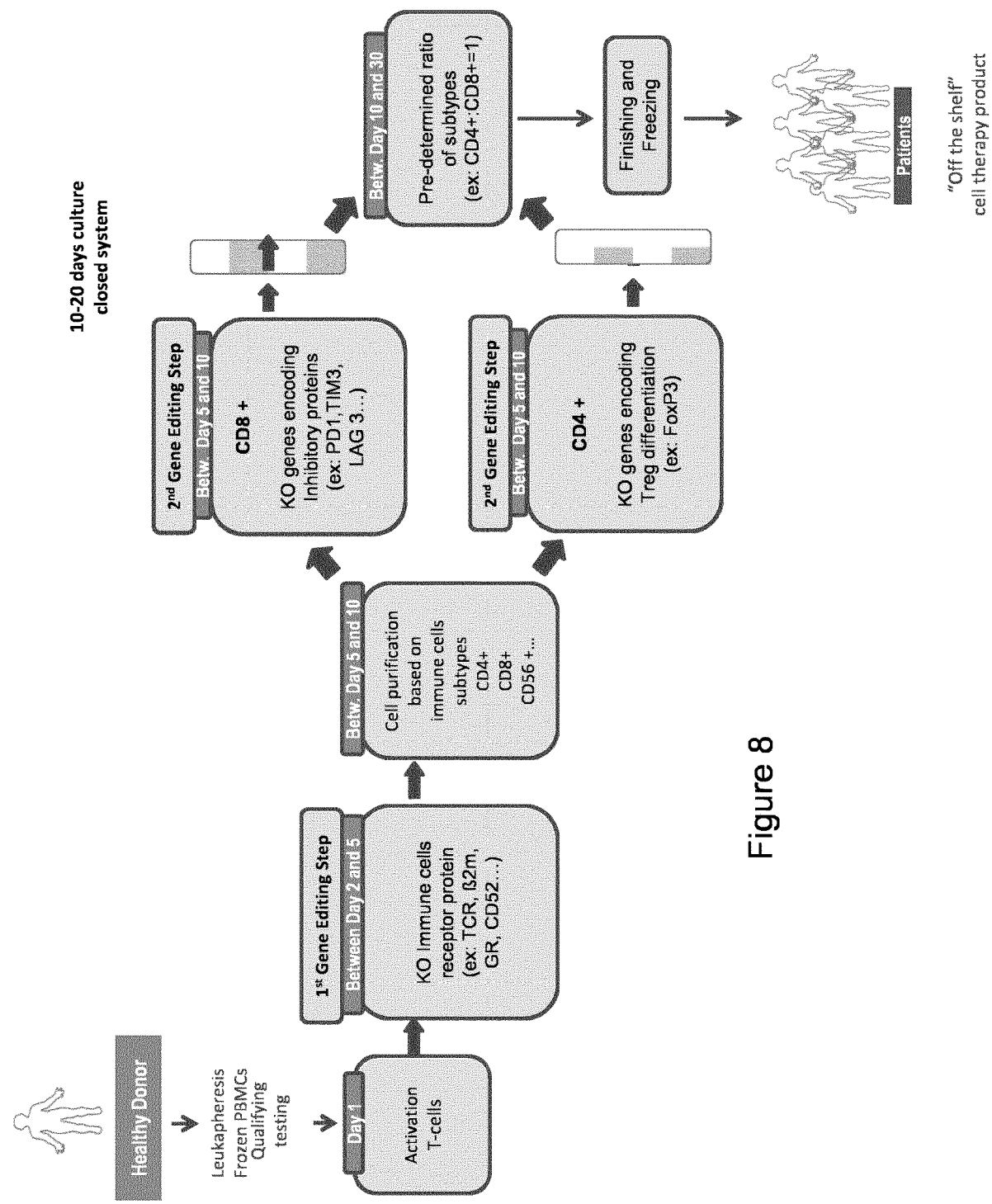

FIG. 8: Schematic representation of one embodiment wherein a cell sorting based on immune cells subtypes, for instance CD4+ and CD8+ cells is performed after the first gene editing step (ex: TCR inactivation) and before the second gene editing step. As per this embodiment, a different gene editing can be applied to the different subtypes respectively, such as for instance the inactivation of FOXP3 in CD4+ cells and the inactivation of PD1 in CD8+ cells. The gene edited cells from the separate batches (ex: CD8+ and CD4+) can be respectively mixed at a predetermined ratio (ex: 1 to 1) to produce more active therapeutic compositions.

Figure 9:
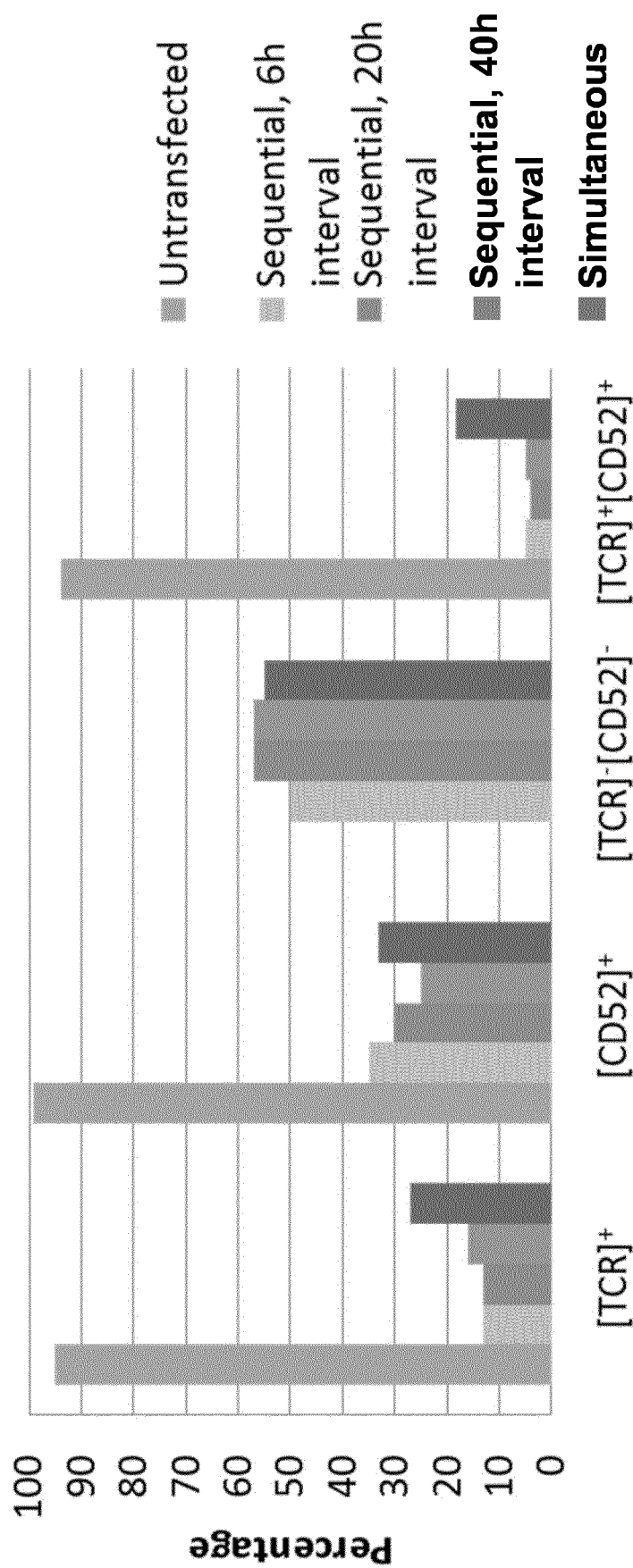

FIG. 9: Diagrams displaying the % number of cells TCR negative, CD52 negative and both TCR and CD52 negative after simultaneous gene editing (TALEN CD52 and TCR together) (see Example 1). Controls are untransfected cells, which results are represented the left columns of the diagrams FIG. 10: T-cell growth curve observed after the different electroporation strategies: simultaneous and sequential according to the invention (6, 20 and 40 h interval between the two CD52 and TCR gene editing steps—see example 1).

Figure 11:
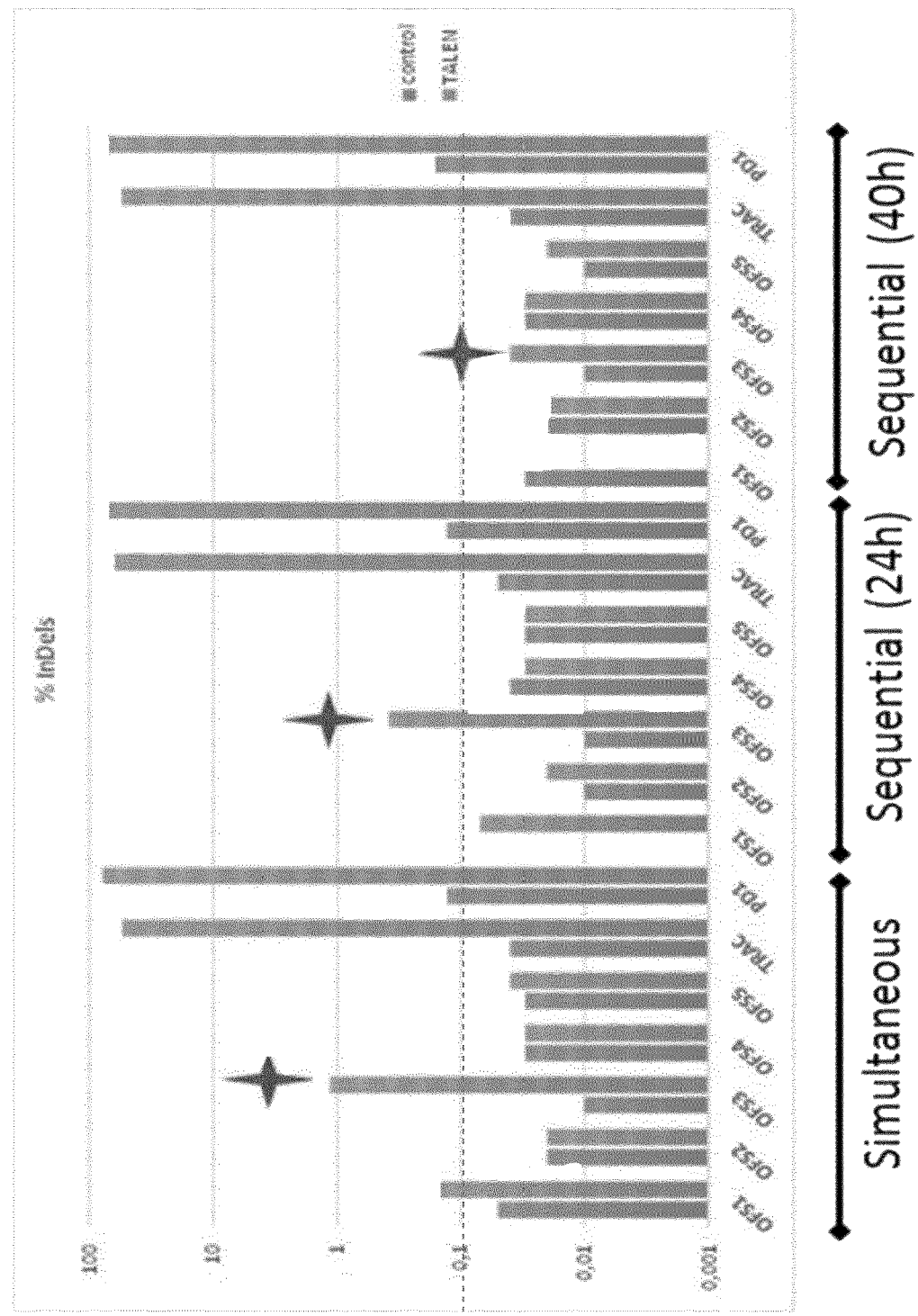

FIG. 11: Frequency of In-deletions (Indels) for 5 off-site targets (OFS1, OFS2, OFS3, OFS4 and OFS5) and TRAC and PD-1 on-site targets after simultaneous or sequential electroporation of TRAC and PD-1 TALEN®. stars highlight the abrogation of off-site 3 (OFS3) target cleavage by the method according to the invention (see example 2).

Figure 12:
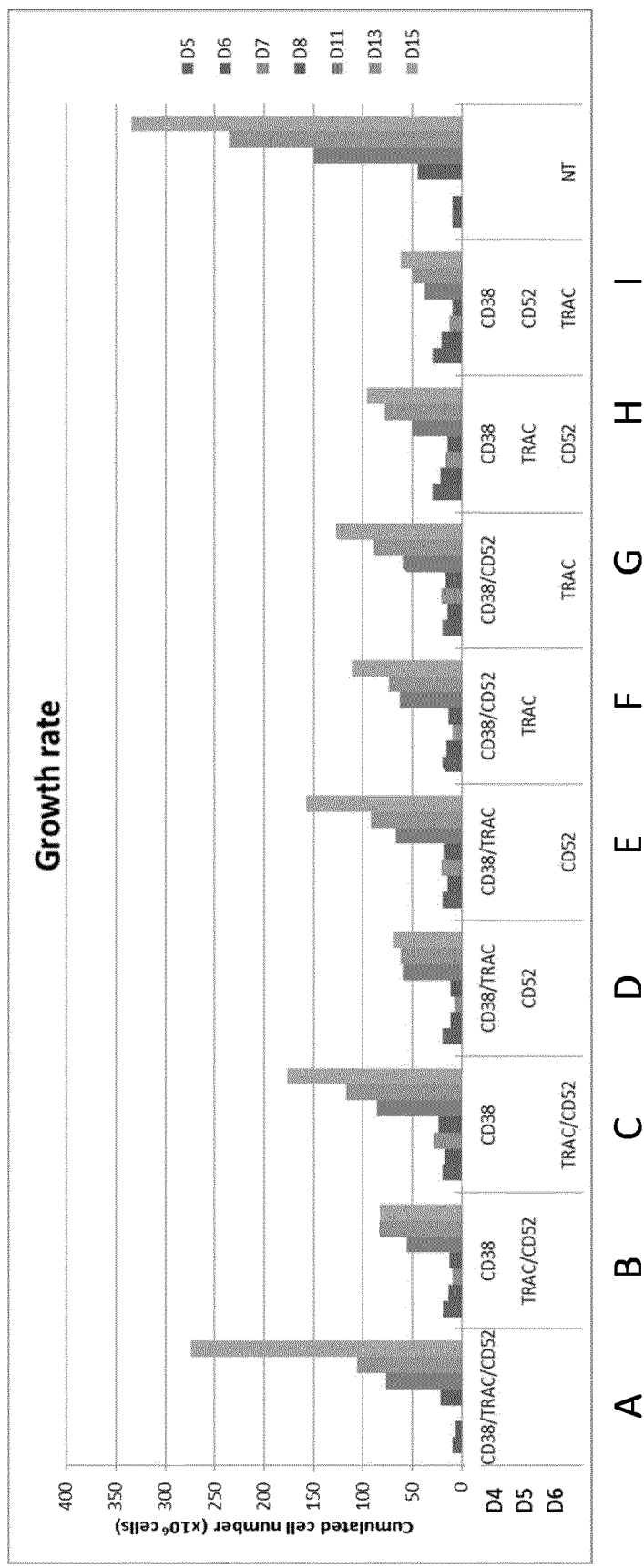

FIG. 12: Diagrams showing the growth of the engineered cells populations over time from Day 5 (D5) post thawing to Day 15 (D15) with respect to the different gene editing strategies detailed in Example 3 and Table 2.

Figure 13:
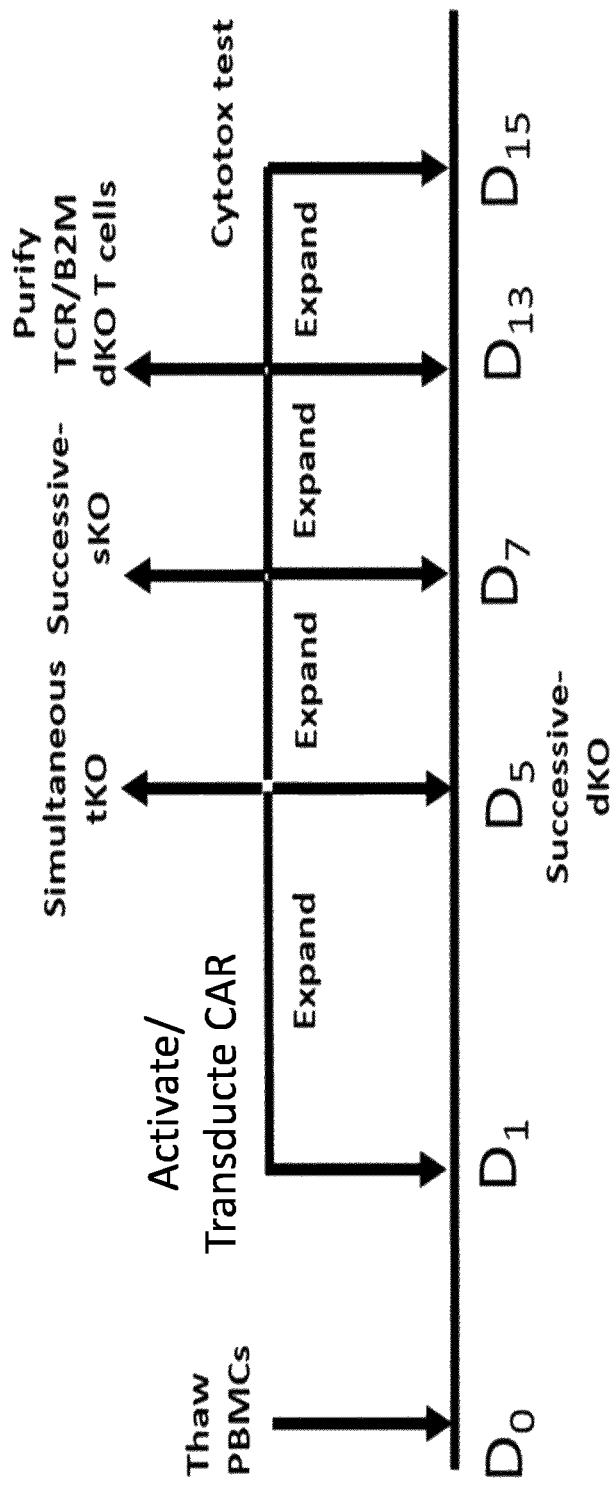

FIG. 13: Schematic representation of workflow for the generation of triple KO CAR T cells, as carried out in example 4.

Figure 14:
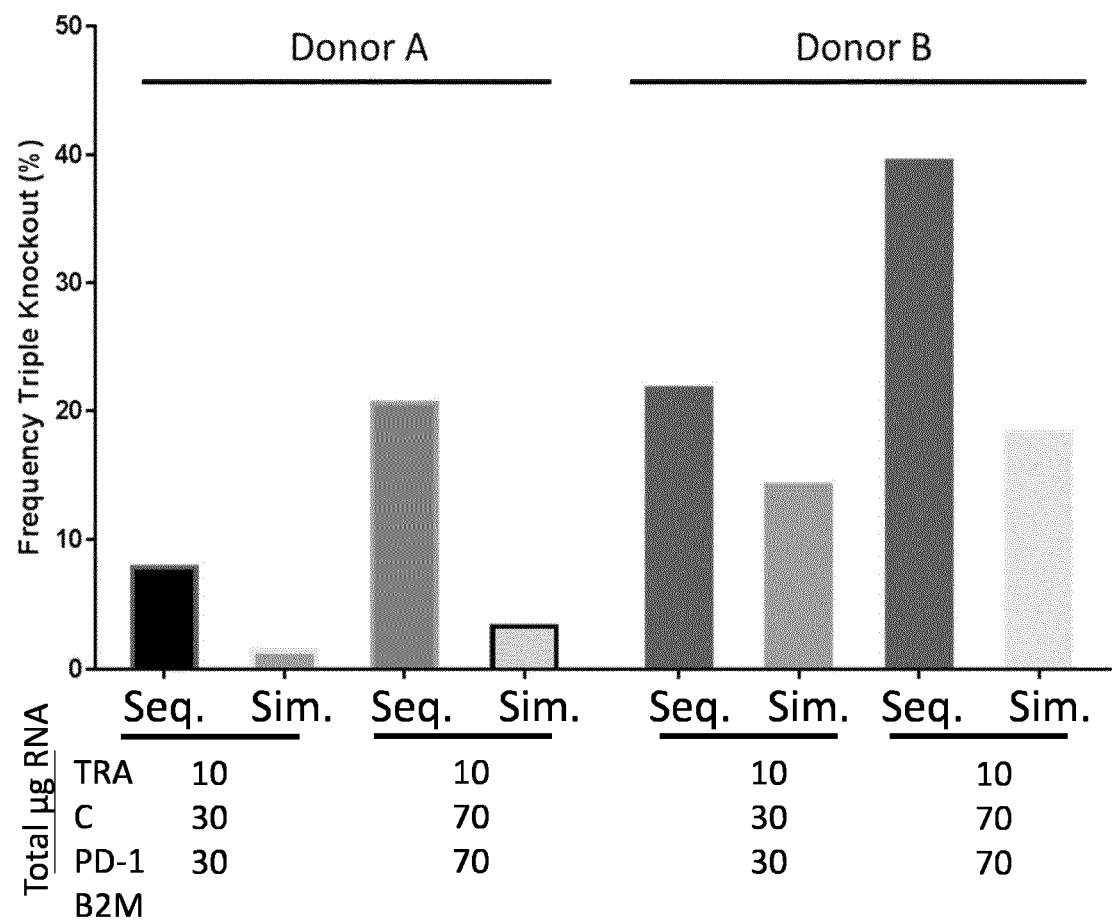

FIG. 14: Diagram displaying the triple KO efficacy (% number TCR/B2M and PD1 negative cells), in two different donors using indicated doses of mRNA enconding TRAC, β2m and PD-1 TALEN®s that were electroporated either simultaneously (Sim.) or sequentially (Seq.), resulting into $[TCR]^{neg}[\beta 2m]^{neg}[PD1]^{neg}$ therapeutically effective number of cells originating from donors, as explained in Example 4.

Figure 15:
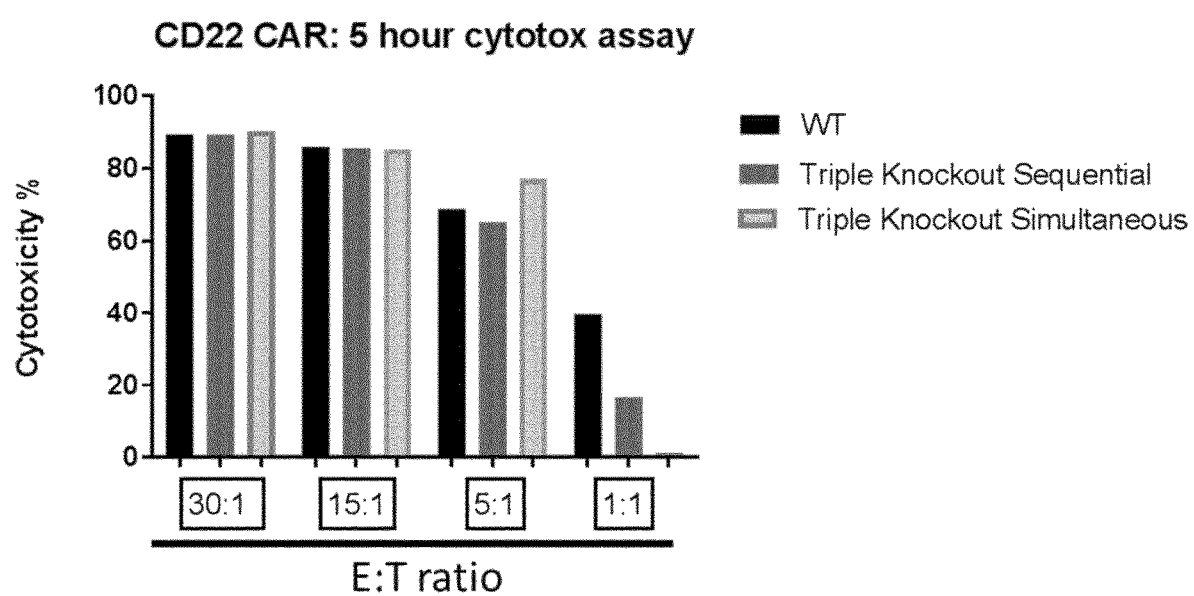

FIG. 15: Diagrams showing cytotoxic activity on Raji cells at different effector to target ratios (E:T) of CD22 CAR-T cells that were either untransfected with TALEN® reagents (WT: black) or TALEN® transfected sequentially (dark grey) or TALEN® transfected simultaneously (light grey).

Table 1: List of genes involved into immune cells inhibitory pathways

Table 2: gene editing efficiency of various sequential gene editing strategies according to the invention as presented in Example 3 (percentage of gene edited cells based on numbers of CD38, TCR and/or CD52 negative cells; D4, D5 and D6 are the number of days after thawing frozen primary cells).

Table 3: Sequence of TALEN ° used in the examples.

Table 4: Selection of antigen markers of various cancers found to be expressed on the surface of T-cells. The inactivation of the genes encoding these antigen markers is proposed as part of one of one of the gene editing steps according to the invention, especially when the engineered immune cells are endowed with chimeric antigen receptors targeting these very antigens.

DETAILED DESCRIPTION OF THE INVENTION

Unless specifically defined herein, all technical and scientific terms used herein have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a general aspect, the present invention relates to methods to perform genome modification in multiple loci in primary cells through sequential electroporation steps, spaced by cell culture, sorting and/or expansion phase(s).

In particular, these methods comprise the steps of:

a) subjecting the primary immune cell to a first electroporation to introduce at least a first sequence-specific reagent into said immune cell;

b) cultivating said primary immune cell thereby enabling said first sequence-specific reagent to modify its genome at a first locus, c) subjecting said primary immune to at least a second electroporation to introduce at least a second sequence-specific reagent into said cell, d) cultivating and expanding said primary immune thereby enabling said second sequence-specific reagent to modify its genome at said second locus.

By "primary cell" or "primary cells" are intended cells taken directly from living tissue (e.g. biopsy material) and established for growth in vitro for a limited amount of time, meaning that they can undergo a limited number of population doublings. Primary cells are opposed to continuous tumorigenic or artificially immortalized cell lines. Non-limiting examples of such cell lines are CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells. Primary cells are generally used in cell therapy as they are deemed more functional and less tumorigenic.

In general, primary immune cells are provided from donors or patients through a variety of methods known in the art, as for instance by leukapheresis techniques as reviewed by Schwartz J. et al. (Guidelines on the use of therapeutic apheresis in clinical practice-evidence-based approach from the Writing Committee of the American Society for Apheresis: the sixth special issue (2013) *J Clin Apher.* 28(3):145-284). The primary immune cells according to the present invention can also be differentiated from stem cells, such as cord blood stem cells, progenitor cells, bone marrow stem cells, hematopoietic stem cells (HSC) and induced pluripotent stem cells (iPS).

By "immune cell" is meant a cell of hematopoietic origin functionally involved in the initiation and/or execution of innate and/or adaptative immune response, such as typically CD3 or CD4 positive cells. The immune cell according to the present invention can be a dendritic cell, killer dendritic cell, a mast cell, a NK-cell, a B-cell or a T-cell selected from the group consisting of inflammatory T-lymphocytes, cytotoxic T-lymphocytes, regulatory T-lymphocytes or helper T-lymphocytes. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and from tumors, such as tumor infiltrating lymphocytes. In some embodiments, said immune cell can be derived from a healthy donor, from a patient diagnosed with cancer or from a patient diagnosed with an infection. In another embodiment, said cell is part of a mixed population of immune cells which present different phenotypic characteristics, such as comprising CD4, CD8 and CD56 positive cells.

By "endonuclease reagent" is meant a nucleic acid molecule that contributes to an endonuclease catalytic reaction in the target cell, itself or as a subunit of a complex, preferably leading to the cleavage of a nucleic acid sequence target. The endonuclease reagents of the invention are generally sequence-specific reagents, meaning that they can induce DNA cleavage in the cells at predetermined loci, referred to by extension as "gene targets". The nucleic acid sequence which is recognized by the sequence specific reagents is referred to as "target sequence". Said target sequence is usually selected to be rare or unique in the cell's genome, and more extensively in the human genome, as can be determined using software and data available from human genome databases, such as that at ensembl. org.

"Rare-cutting endonucleases" are sequence-specific endonuclease reagents of choice, insofar as their recognition sequences generally range from 10 to 50 successive base pairs, preferably from 12 to 30 bp, and more preferably from 14 to 20 bp.

According to a preferred aspect of the invention, the endonuclease reagent is transiently expressed into the cells, meaning that said reagent is not supposed to integrate into the genome or persist over a long period of time, such as be the case of RNA, more particularly mRNA, proteins or complexes mixing proteins and nucleic acids (eg: Ribonucleoproteins). In general, 80% the endonuclease reagent is degraded by 30 hours, preferably by 24, more preferably by 20 hours after transfection.

According to a preferred aspect of the invention, said endonuclease reagent is a nucleic acid encoding an "engineered" or "programmable" rare-cutting endonuclease, such as a homing endonuclease as described for instance by Arnould S., et al. (WO2004067736), a zinc finger nuclease (ZFN) as described, for instance, by Urnov F., et al. (Highly efficient endogenous human gene correction using designed zinc-finger nucleases (2005) *Nature* 435:646-651), a TALE-Nuclease as described, for instance, by Mussolino et al. (A novel TALE nuclease scaffold enables high genome editing activity in combination with low toxicity (2011) *Nucl. Acids Res.* 39(21):9283-9293), or a MegaTAL nuclease as described, for instance by Boissel et al. (MegaTALs: a rare-cleaving nuclease architecture for therapeutic genome engineering (2013) Nucleic Acids Research 42 (4):2591-2601).

According to the invention, the endonuclease reagent is preferentially under RNA form to allow transient endonuclease activity of said reagent into the target cell and make the entire capsule biodegradable in-vivo. Even more preferably, the endonuclease reagent is under the form of a mRNA for the expression of the rare cutting endonuclease into the cells. The endonuclease under mRNA form is preferably synthetized with a cap to enhance its stability according to techniques well known in the art, as described, for instance, by Kore A. L., et al. (Locked nucleic acid (LNA)-modified dinucleotide mRNA cap analogue: synthesis, enzymatic incorporation, and utilization (2009) *J Am Chem Soc.* 131(18):6364-5).

Due to their higher specificity, TALE-nuclease have proven to be particularly appropriate for therapeutic applications, especially under heterodimeric forms—i.e. working by pairs with a "right" monomer (also referred to as "5'" or "forward") and 'left' monomer (also referred to as "3'"" or "reverse") as reported for instance by Mussolino et al. (TALEN® facilitate targeted genome editing in human cells with high specificity and low cytotoxicity (2014) *Nucl. Acids Res.* 42(10): 6762-6773).

According to another embodiment, the endonuclease reagent is a RNA-guide to be used in conjunction with a RNA guided endonuclease, such as Cas9 or Cpf1, as per, inter alia, the teaching by Doudna, J., and Chapentier, E., (The new frontier of genome engineering with CRISPR-Cas9 (2014) *Science* 346 (6213):1077), which is incorporated herein by reference.

However, because engineered rare-cutting endonuclease are sequence specific unique reagents, it cannot be excluded that, in some instances, they can promote or induce some chromosomal rearrangements, especially when several gene loci need to be cleaved in the same cell.

Rearrangements are more prompt to happen, for instance, when multiple cleavage sites get simultaneously cut on the same chromosome or when pseudo cleavage sites appear from the unexpected combinations of heterodimers not initially designed to work together.

The inventors have more particularly sought for lowering this risk without reducing the yield of the engineered cells when treated with any of the above endonuclease reagents (i.e. maintaining high gene KO efficacy and high cellular viability).

Sequential Steps to Produce Batches of Engineered Primary Immune Cells of Therapeutic Grade The present invention thus provides a method allowing stacking gene editing in mammalian cells, while preventing undesirable genome deletions or translocations.

By "gene editing" is meant, throughout the present specification, any methods by which a genomic sequence is modified by insertion, deletion or replacement at a selected locus by using at least an enzyme that cleaves phosphodiester bond within a polynucleotide chain.

The method of the present invention can be associated with other methods involving physical of genetic transformations, such as a viral transduction or transfection using nanoparticles, in particular for transient expression of exogenous genetic sequences.

The invention can be applied to human immune cells, in particular activated T-cells by alternating transfection (preferably by electroporation) and culture steps. Examples of such cycles as delineated below as examples:

(TNx→h→TNx)×n
(TNx/TNx→h→TNx)×n
(TNx→h→TNx/TNx)×n
(TNx/TNx→h→TNx/TNx)×n where TNx is a Transfection (T) of a specific endonuclease reagent N, (x≥1)

h an interval of time in hours, and (h≥1)

n is the number of subsequent transfection (n≥1)

The above cycle may be combined with each other depending on the number of the different endonuclease reagents to be used sequentially.

Preferably, each gene editing step targets one locus at a time.

On another hand, the use of sequence-specific endonuclease reagents can be combined with other types of cell transformation not involving sequence specific endonuclease reagents, such as a retroviral transduction. This is of particular interest, for instance, for the production of primary immune cells expressing a recombinant receptors, such as a chimeric antigen receptor (CAR) or a recombinant TCR. Such chimeric antigen receptors are generally encoded by exogenous sequences which are introduced into cells by means of viral vectors, in particular lentiviral vectors. It is therefore advantageous to combine the sequential gene editing steps of the present invention with viral transduction steps, such as illustrated in FIGS. 3, 5, 6 and 7.

Example of combinations of sequential gene editing steps and transduction steps are delineated below:

Transduction→h→(TNx→h→TNx)×n;
Transduction→h→(TNx/TNx→h→TNx)×n;
Transduction→h→(TNx→h→TNx/TNx)×n;
Transduction→h→(TNx/TNx→h→TNx/TNx)×n;
(TNx→h→TNx)×n→h→Transduction)×n;
(TNx/TNx→h→TNx)×n→h→Transduction)×n;
(TNx→h→TNx/TNx)×n→h→Transduction;
(TNx/TNx→h→TNx/TNx)×n→h→Transduction;
(TNx→h→Transduction→h→TNx)×n;
(TNx/TNx→h→Transduction→h→TNx)×n;
(TNx→h→Transduction→h→TNx/TNx)×n;
(TNx/TNx→h→Transduction→h→TNx/TNx)×n;

The transduction step may also take place prior to a gene editing step, when, for instance, vector introduces a template DNA into the primary cell to be integrated at a locus during the subsequent gene editing step. The sequence-specific endonuclease reagent is then introduced into the cell to promote the integration of said exogenous DNA at said locus. One preferred aspect is a method of the present invention comprising a first gene editing step, followed by a transduction step involving an AAV vector comprising an exogenous sequence to be integrated at a predetermined locus, prior to a second gene editing step wherein the exogenous DNA comprised in the AAV vector is integrated at said predetermined locus.

According to one aspect of the invention, the sequential gene editing method may combine single gene editing steps (TNx) with multiplexing gene editing steps (TNx/TNx). During the multiplexing gene editing step, different endonuclease reagents may be used at different/multiple loci together. Endonucleases have different types of cleavage signatures: some of them can create "blunt ends", such as CRISPR, 5' "cohesive ends" such as zing Finger nucleases or TALE-nucleases or 3' "cohesive ends" by using homing endonucleases. Combinations of endonuclease reagents can be made based on the type of cleavage sought. For instance, cohesive ends are better suited for integration of exogenous DNA than blunt ends for instance. One preferred aspect of the invention is the combined use of endonuclease reagents creating different types of cleavage signatures to reduce the deletions or translocations occurring at/or between the different gene-edited loci.

According to a preferred embodiment of the invention, the primary immune cells are cultivated for an interval of time (h) as referred to above that is more than 10 hours, preferably from 12 to 72 hours and more preferably from 12 to 48 hours.

According to a particular embodiment of the invention, a purification step can be performed between general step b) and c), as also illustrated in FIGS. 4, 7 and 13.

This purification step can be performed for the sake of purity by any standard method known in the art. In the present case, the purification step can help to select the cells which have undergone the gene editing achieved in step a). The purification can thus rely on the product resulting from the first gene editing reaction, such as a product resulting from the modification or insertion of a genetic sequence at said first locus, or the absence of a gene product in case of a deletion of such genetic sequence. In a preferred embodiment, the first gene editing step may help the expression of receptors or membrane proteins, which make the immune cells more receptive to the second gene editing step. The cells can also become more receptive to viral vectors transduction if genes involved into viral transformation are modified prior to the second gene editing.

The genes that can be targeted as part of the first gene editing step, can be genes the modification of which will facilitate viral transduction or the realization of the second gene editing step or of any subsequent transduction or transfection step. Such genes can be, for instance, genes encoding cell restriction factors, such as TRIM5a (Uniprot Q9C035), APOBEC protein family (apolipoprotein B mRNA editing enzyme), and SAMHD1 (Uniprot Q9Y3Z3). By "cell restriction factors" is meant molecules that directly and dominantly cause a significant decrease in viral infectivity.TRIM5a, for instance, is a protein known to mediate/inhibit lentiviral, such as HIV, entry into immune cells (Stremlau M, et al. "Specific recognition and accelerated uncoating of retroviral capsids by the TRIM5alpha restriction factor" (2006) *PNAS* 103(14): 5514-9). The inactivation of TRIM5a, SAMHD1 or proteins of APOBEC family as part of one of the gene editing steps of the present invention can increase the infectivity of primary cells to viral vectors during subsequent transduction steps.

According to preferred embodiments, the invention provides that steps a) to d) of the general method are performed within 240 hours, preferably within 120 hours, more preferably within 96 hours, even more preferably within 72 hours. This limited period of time allows better recovery of the primary immune cells and limits their exhaustion. Limited exhaustion can be controlled at different steps during the process by one skilled in the art by using specific exhaustion markers such as reviewed by Wherry, J. A. (T cell exhaustion (2011) *Nature Immunology* 12:492-499).

According to a preferred embodiment of the invention, the transfection step T, such as steps a) and c) in the general method previously described, as well as any further steps TN (where N is the number of gene editing steps) are performed by electroporation.

Surprisingly, successive electroporation steps were found to be less destructive and/or less genotoxic for the primary cells than any other methods performing multiplex gene editing where various endonuclease reagents are transfected in one shot.

The method according to the present invention can comprise at least one further step of submitting the primary immune cell to a third electroporation to introduce at least a third sequence-specific reagent into said cell.

Such electroporation steps are typically performed in closed chambers comprising parallel plate electrodes producing a pulse electric field between said parallel plate electrodes greater than 100 volts/cm and less than 5,000 volts/cm, substantially uniform throughout the treatment volume such as described in WO/2004/083379, which is incorporated by reference, especially from page 23, line 25 to page 29, line 11. One such electroporation chamber preferably has a geometric factor ($cm^{-1}$) defined by the quotient of the electrode gap squared (cm2) divided by the chamber volume ($cm^3$), wherein the geometric factor is less than or equal to 0.1 $cm^{-1}$, wherein the suspension of the cells and the sequence-specific reagent is in a medium which is adjusted such that the medium has conductivity in a range spanning 0.01 to 1.0 milliSiemens. In general, the suspension of cells undergoes one or more pulsed electric fields. With the method, the treatment volume of the suspension is scalable, and the time of treatment of the cells in the chamber is substantially uniform.

According to a preferred embodiment of the invention, the sequence specific reagent is under the form of nucleic acids, more preferably under DNA or RNA form. Under such forms, the nucleic acids can either code for a polypeptide, typically a rare cutting endonuclease a subunit thereof, or a conjugate of both a polynucleotide and a polypeptide. The reagents can also be under the form RNA or DNA guides directing guided endonucleases such as Cas9 or Cpf1 (RNA-guided endonucleases) or Argonaute (DNA-guided endonucleases) as recently respectively described by Zetsche, B. et al. (Cpf1 Is a Single RNA-Guided Endonuclease of a Class 2 CRISPR-Cas System (2015) *Cell* 163(3): 759-771) and by Gao F. et al. (DNA-guided genome editing using the *Natronobacterium gregoryi* Argonaute (2016) *Nature Biotech*). According to a most preferred embodiment, the sequence-specific reagent is under mRNA form and encodes a rare-cutting endonuclease, selected from programmable RNA or DNA guided endonuclease, TALE-nuclease, Zing-finger nuclease (ZFN), a megaTAL or a homing endonuclease.

According to another aspect of the invention said first and/or second sequence-specific reagent is an interference RNA (RNAi) or a polynucleotide encoding same.

As previously mentioned, a transduction step can be introduced between steps b) and c) of the general method, especially an integrative lentiviral or retroviral vector for stable expression of a transgene. This is particularly adapted to express chimeric antigen receptors (CAR) at the surface of the primary immune cells modified as the present invention. Such methods for CAR expression in allogeneic primary cells are described for instance in WO2013176915. Non-integrative viral vectors can also be used, as also described by the applicant in WO2015028683. Non integrative viral vector can be used, inter alia, as a template or donor DNA for homologous recombination or NHEJ integration of transgene into the immune cell's genome as part of the second gene editing step as per the present invention.

The steps of the present method are generally performed at mammalian cells physiological temperature (37° C. for human cells), but certain steps of the method may be performed at non-physiological temperatures, between 30 and 37° C., or even lower between 25 and 35° C., during a limited period of time, from 30 minutes to 12 hours, preferably from 1 to 10 hours, more preferably from 1 to 5, and even more preferably from 30 minutes to 2 hours. For instance, it has been observed that performing the electroporation steps at lower temperature, e.g. below about 35° C., such as at about 30° C., favors transfection efficiency.

As further illustrated in the present specification, the present method aims particularly at producing immune cells, preferably primary immune cells, genetically modified at multiple loci, especially by gene editing, for their subsequent use in cell therapy.

Such immune cells are generally endowed with recombinant receptors, such as CAR or recombinant TCR, which confer them higher specificity toward malignant or infected cells. These recombinant receptors are generally encoded by exogenous polynucleotides which are introduced into the cell using viral vectors as per one of the transduction steps referred to previously.

The CARs expressed by these cells specifically target antigen markers at the surface of malignant or infected cells, which further help said immune cells to destroy these cells in-vivo as reviewed by Sadelain M. et al. ["The basic principles of chimeric antigen receptor design" (2013) *Cancer Discov.* 3(4):388-98].

In general, CAR polypeptides comprise an antigen binding domain, a transmembrane domain, and an intracellular domain comprising a costimulatory domain and/or a primary signaling domain, wherein said antigen binding domain binds to the tumor antigen associated with the disease.

Many CARs have been described in the art, which can be used to carry out the present method, which can bind tumor antigen as diverse as one selected from: CD19 molecule (CD19); membrane spanning 4-domains A1 (MS4A1 also known as CD20); CD22 molecule (CD22); CD24 molecule (CD24); CD248 molecule (CD248); CD276 molecule (CD276 or B7H3); CD33 molecule (CD33); CD38 molecule (CD38); CD44v6; CD70 molecule (CD70); CD72; CD79a; CD79b; interleukin 3 receptor subunit alpha (IL3RA also known as CD123); TNF receptor superfamily member 8 (TNFRSF8 also known as CD30); KIT proto-oncogene receptor tyrosine kinase (CD117); V-set pre-B cell surrogate light chain 1 (VPREB1 or CD179a); adhesion G protein-coupled receptor E5 (ADGRE5 or CD97); TNF receptor superfamily member 17 (TNFRSF17 also known as BCMA); SLAM family member 7 (SLAMF7 also known as CS1); L1 cell adhesion molecule (L1CAM); C-type lectin domain family 12 member A (CLEC12A also known as CLL-1); tumor-specific variant of the epidermal growth factor receptor (EGFRvIII); thyroid stimulating hormone receptor (TSHR); Fms related tyrosine kinase 3 (FLT3); ganglioside GD3 (GD3); Tn antigen (Tn Ag); lymphocyte antigen 6 family member G6D (LY6G6D); Delta like canonical Notch ligand 3 (DLL3); Interleukin-13 receptor subunit alpha-2 (IL-13RA2); Interleukin 11 receptor subunit alpha (IL11RA); mesothelin (MSLN); Receptor tyrosine kinase like orphan receptor 1 (ROR1); Prostate stem cell antigen (PSCA); erb-b2 receptor tyrosine kinase 2 (ERBB2 or Her2/neu); Protease Serine 21 (PRSS21); Kinase insert domain receptor (KDR also known as VEGFR2); Lewis y antigen (LewisY); Solute carrier family 39 member 6 (SLC39A6); Fibroblast activation protein alpha (FAP); Hsp70 family chaperone (HSP70); Platelet-derived growth factor receptor beta (PDGFR-beta); Cholinergic receptor nicotinic alpha 2 subunit (CHRNA2); Stage-Specific Embryonic Antigen-4 (SSEA-4); Mucin 1, cell surface associated (MUC1); mucin 16, cell surface associated (MUC16); claudin 18 (CLDN18); claudin 6 (CLDN6); Epidermal Growth Factor Receptor (EGFR); Preferentially expressed antigen in melanoma (PRAME); Neural Cell Adhesion Molecule (NCAM); ADAM metallopeptidase domain 10 (ADAM10); Folate receptor 1 (FOLR1); Folate receptor beta (FOLR2); Carbonic Anhydrase IX (CA9); Proteasome subunit beta 9 (PSMB9 or LMP2); Ephrin receptor A2 (EphA2); Tetraspanin 10 (TSPAN10); Fucosyl GM1 (Fuc-GM1); sialyl Lewis adhesion molecule (sLe); TGS5; high molecular weight-melanoma-associated antigen (HMW-MAA); o-acetyl-GD2 ganglioside (OAcGD2); tumor endothelial marker 7-related (TEM7R); G protein-coupled receptor class C group 5, member D (GPRC5D); chromosome X open reading frame 61 (CXORF61); ALK receptor tyrosine kinase (ALK); Polysialic acid; Placenta-specific 1 (PLAC1); hexasaccharide portion of globoH glycoceramide (GloboH); NY-BR-1 antigen; uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 family member K (LY6K); olfactory receptor family 51 subfamily E member 2 (OR51E2); TCR Gamma Alternate Reading Frame Protein (TARP); Wilms tumor protein (WT1); ETV6-AML1 fusion protein due to 12;21 chromosomal translocation (ETV6-AML1); sperm autoantigenic protein 17 (SPA17); X Antigen Family, Member 1E (XAGE1E); TEK receptor tyrosine kinase (Tie2); melanoma cancer testis antigen-1 (MAD-CT-1); melanoma cancer testis antigen-2 (MAD-CT-2); Fos-related antigen 1; p53 mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B 1; v-myc avian myelocytomatosis viral oncogene neuroblastoma derived homolog (MYCN); Ras Homolog Family Member C (RhoC); Cytochrome P450 1B 1 (CYP1B 1); CCCTC-Binding Factor (Zinc Finger Protein)-Like (BORIS); Squamous Cell Carcinoma Antigen Recognized By T Cells 3 (SART3); Paired box protein Pax-5 (PAX5); proacrosin binding protein sp32 (OY-TES 1); lymphocyte-specific protein tyrosine kinase (LCK); A kinase anchor protein 4 (AKAP-4); synovial sarcoma, X breakpoint 2 (SSX2); Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); and immunoglobulin lambda-like polypeptide 1 (IGLL1).

More preferred CARs according to the present invention are those described in the examples, which more preferably comprise an extracellular binding domain directed against one antigen selected from CD19, CD22, CD33, 5T4, ROR1, CD38, CD52, CD123, CS1, BCMA, Flt3, CD70, EGFRvIII, WT1, HSP-70 and CCL1. Even more preferred are CARs directed against CD22, CD38, 5T4, CD123, CS1, HSP-70 and CCL1. Such CARs have preferably one structure as described in WO2016120216.

Immune cells can also express recombinant T-Cell receptors. T cells recognise MHC-peptide conjugates on target cells through the paired α and β chains of the TCR. This pairing confers the antigen specificity of the immune cell. One gene therapy approach has involved the molecular cloning of the TCR genes known to be specific for an antigen of choice. These chains are then introduced into T cells usually by means of a retroviral vector in a similar way as with CAR. Consequently, expression of the cloned TCRα and TCRβ genes endows the transduced immune cells with a functional specificity determined by the pairing of these new genes. Because TCRs recognize processed peptides presented on MHC, targeted antigens can be derived from the entire protein composition of the tumor cells, including intracellular proteins, whereas CARs are generally designed to recognize molecules expressed on the surface of target cells. This quality also allows TCRs to target a large number of non-surface antigens of virally infected cells and tumors associated with viral infection, such as hepatitis-associated hepatocellular carcinoma, papilloma virus-associated cervical cancer, and Epstein-Barr virus-related malignancies (Spear, T. et al. (2016). Strategies to genetically engineer T cells for cancer immunotherapy. *Cancer Immunology Immunotherapy:* 65(6):631-649).

Preferred recombinant TCR to be used in the present invention are those directed against antigen specific of cancer cells, such as MART-1, MAGE-1, MAGE-2, MAGE-3 MAGE-12, BAGE, GAGE, NY-ESO-1, or overexpressed in cancer cells, such as a-Fetoprotein, Telomerase catalytic protein, G-250, MUC-1, CarcinoEmbryonic antigen (CEA), p53, Her-2/Neu and WT1 [Rosenberg S. A., (2001) Progress in human tumour immunology and immunotherapy *Nature*. 411(6835):380-4].

The exogenous polynucleotide sequence encoding the recombinant receptors are generally introduced by a transduction step, which can be performed in the course of the present invention as shown for instance in FIGS. 4, 7 and 13 by using a viral vector, such as a lentiviral vector.

Alternatively, or as part of a gene editing step, AAV vectors can be used as a DNA template for gene targeted insertion of said polynucleotide sequence encoding a recombinant receptor at a desired locus by NHEJ or homologous recombination.

The insertion locus may be selected to disrupt an endogenous gene present at this locus, such a gene encoding a component of TCR or β2m as previously described.

Also said exogenous polynucleotide sequence can be integrated at a locus preferably encoding TCR, HLA, β2m, HLA, PD1 or CTLA4, as part of the editing steps of the present invention.

In particular, the inventors have significantly improved the rate of gene targeted insertion into human cells by using AAV vectors from the AAV6 family.

According to a preferred embodiment, the method of the invention can therefore comprise a step consisting in:
  transducing into said cell an AAV vector comprising said exogenous nucleic acid sequence and sequences homologous to the targeted endogenous DNA sequence, and optionally,
  Inducing the expression of a sequence specific endonuclease reagent to cleave said endogenous sequence at the locus of insertion.

The obtained insertion of the exogenous nucleic acid sequence may then result into the introduction of genetic material, correction or replacement of the endogenous sequence, more preferably "in frame" with respect to the endogenous gene sequences at that locus.

Alloreactivity and/or Engraftment of the Immune Cells:

The method according to the invention is particularly adapted to prepare primary immune cells for allogeneic therapeutic use. By "allogeneic therapeutic use" is meant that the cells originate from a donor in view of being infused into patients having a different haplotype. Indeed, the present invention provides with an efficient method for obtaining primary cells, which can be gene edited in various gene loci involved into host-graft interaction and recognition. Other loci may also be edited in view of improving the activity, the survival or the life-time of the engineered primary cells. Such engineered immune cells are preferably primary T cells.

FIG. 1 maps the main cell functions that can be modified by gene editing according to the present invention to improve the efficiency of the engineered immune cells. Any gene inactivation listed under each function can be combined with another to obtain a synergistic effect on the overall therapeutic potency of the immune cells.

The present method is particularly useful for developing engineered non-alloreactive T-cells for immunotherapy and more specifically to methods for increasing the persistence and/or the engraftment of allogeneic immune cells by proceeding with at least one step of inactivation, preferably permanently, of a gene implicated in the self/non-self recognition, using preferably specific rare-cutting endonuclease.

According to a preferred aspect of the invention, one of the gene editing steps aims to reduce host versus graft disease (GVHD) reaction or immune rejection upon introduction of the allogeneic cells into the recipient patient. For instance, one of the sequence-specific reagents used in the method can reduce or prevent the expression of TCR in primary T-cells, such as the genes encoding TCR-alpha or TCR-beta.

As another preferred aspect, one gene editing step is to reduce or prevent the expression of the β2m protein and/or another protein involved in its regulation such as C2TA (Uniprot P33076) or in MHC recognition, such as HLA proteins. This permits the engineered immune cells to be less alloreactive when infused into patients.

Most preferred, is the gene editing of both TCR and β2m as part of the sequential gene editing method of the present invention into T-cells or precursor cells thereof, which method can comprise the steps of introducing an exogenous polynucleotide encoding recombinant receptors, such as CARs or recombinant TCR previously mentioned, and more preferably at the TCRalpha or TCRbeta locus.

Inhibiting Checkpoint Receptors and Immune Cells Inhibitory Pathways:

According to a preferred aspect of the invention, one of the gene editing steps, aims to disrupt the expression of a protein involved in immune cells inhibitory pathways, in particular those referred to in the literature as "immune checkpoint" (Pardoll, D. M. (2012) The blockade of immune checkpoints in cancer immunotherapy, *Nature Reviews Cancer*, 12:252-264). In the sense of the present invention, "immune cells inhibitory pathways" means any gene expression in immune cells that leads to a reduction of the cytotoxic activity of the lymphocytes towards malignant or infected cells. This can be for instance a gene involved into the expression of FOXP3, which is known to drive the activity of Tregs upon T cells (moderating T-cell activity).

"Immune checkpoints" are molecules in the immune system that either turn up a signal (co-stimulatory molecules) or turn down a signal of activation of an immune cell. As per the present invention, immune checkpoints more particularly designate surface proteins involved in the ligand-receptor interactions between T cells and antigen-presenting cells (APCs) that regulate the T cell response to antigen (which is mediated by peptide-major histocompatibility complex (MHC) molecule complexes that are recognized by the T cell receptor (TCR)). These interactions can occur at the initiation of T cell responses in lymph nodes (where the major APCs are dendritic cells) or in peripheral tissues or tumours (where effector responses are regulated). One important family of membrane-bound ligands that bind both co-stimulatory and inhibitory receptors is the B7 family. All of the B7 family members and their known ligands belong to the immunoglobulin superfamily. Many of the receptors for more recently identified B7 family members have not yet been identified. Tumour necrosis factor (TNF) family members that bind to cognate TNF receptor family molecules represent a second family of regulatory ligand-receptor pairs. These receptors predominantly deliver co-stimulatory signals when engaged by their cognate ligands. Another major category of signals that regulate the activation of T cells comes from soluble cytokines in the microenvironment. In other cases, activated T cells upregulate ligands, such as CD40L, that engage cognate receptors on APCs. A2aR, adenosine A2a receptor; B7RP1, B7-related protein 1; BTLA, B and T lymphocyte attenuator; GAL9, galectin 9; HVEM, herpesvirus entry mediator; ICOS, inducible T cell co-stimulator; IL, interleukin; KIR, killer cell immunoglobulin-like receptor; LAG3, lymphocyte activation gene 3; PD1, programmed cell death protein 1; PDL, PD1 ligand; TGFβ, transforming growth factor-β; TIM3, T cell membrane protein 3.

Examples of further genes, which expression could be reduced or suppressed to turn-up activation in the engineered immune cells according the present invention are listed in Table 1.

For instance, one of the sequence-specific reagents used in the method can reduce or prevent the expression by the immune cell of at least one protein selected from PD1 (Uniprot Q15116), CTLA4 (Uniprot P16410), PPP2CA (Uniprot P67775), PPP2CB (Uniprot P62714), PTPN6 (Uniprot P29350), PTPN22 (Uniprot Q9Y2R2), LAG3 (Uniprot P18627), HAVCR2 (Uniprot Q8TDQ0), BTLA (Uniprot Q7Z6A9), CD160 (Uniprot O95971), TIGIT (Uniprot Q495A1), CD96 (Uniprot P40200), CRTAM (Uniprot O95727), LAIR1 (Uniprot Q6GTX8), SIGLEC7 (Uniprot Q9Y286), SIGLEC9 (Uniprot Q9Y336), CD244 (Uniprot Q9BZW8), TNFRSF10B (Uniprot O14763), TNFRSF10A (Uniprot O00220), CASP8 (Uniprot Q14790), CASP10 (Uniprot Q92851), CASP3 (Uniprot P42574), CASP6 (Uniprot P55212), CASP7 (Uniprot P55210), FADD (Uniprot Q13158), FAS (Uniprot P25445), TGFBRII (Uniprot P37173), TGFRBRI (Uniprot Q15582), SMAD2 (Uniprot Q15796), SMAD3 (Uniprot P84022), SMAD4 (Uniprot Q13485), SMAD10 (Uniprot B7ZSB5), SKI (Uniprot P12755), SKIL (Uniprot P12757), TGIF1 (Uniprot Q15583), MORA (Uniprot Q13651), IL10RB (Uniprot Q08334), HMOX2 (Uniprot P30519), IL6R (Uniprot P08887), IL6ST (Uniprot P40189), EIF2AK4 (Uniprot Q9P2K8), CSK (Uniprot P41240), PAG1 (Uniprot Q9NWQ8), SIT1 (Uniprot Q9Y3P8), FOXP3 (Uniprot Q9BZS1), PRDM1 (Uniprot Q60636), BATF (Uniprot Q16520), GUCY1A2 (Uniprot P33402), GUCY1A3 (Uniprot Q02108), GUCY1B2 (Uniprot Q8BXH3) and GUCY1B3 (Uniprot Q02153). The gene editing introduced in the genes encoding the above proteins is preferably combined with an inactivation of TCR in CAR T cells.

Preference is given to inactivation of PD1 and CTLA4, in combination with TCR.

To improve the efficiency of the engineered cells according to the present invention, the steps of the present method using sequence-specific endonuclease reagents, can be followed by a step of contacting said engineered immune cells with at least one non-endogenous immunosuppressive polypeptide, such as a PD-L1 ligand and/or CTLA-4 Ig.

TABLE 1

List of genes involved into immune cells inhibitory pathways

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signalling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Prevention of TCR signalling | | CSK, PAG1 SIT1 |
| Induced Treg Transcription factors controlling exhaustion | induced Treg transcription factors controlling exhaustion | FOXP3 PRDM1 BATF |
| Hypoxia mediated tolerance | iNOS induced guanylated cyclase | GUCY1A2, GUCY1A3, GUCY1B2, GUCY1B3 |

Preference is given to the production of immune cells combining gene editing, into at least the genes encoding:
  TCR, PD1 and LAG3;
  TCR, PD1 and FOXP3;
  TCR, CTLA4 and LAG3;
  TCR, CTLA4 and FOXP3;

And even more preferably to the production of immune cells combining gene editing steps into at least the genes encoding:
  TCR, β2m and PD1
  TCR, β2m and CTLA4
  TCR, β2m and LAG3
  TCR, β2m and FOXP3
preferably by inhibiting or inactivating the expression of these proteins.

Inhibiting Suppressive Cytokines/Metabolites

According to another aspect of the invention, the gene editing step concerns genes encoding or positively regulating suppressive cytokines or metabolites or receptors thereof, in particular TGFbeta (Uniprot P01137), IL10R (Uniprot Q13651 and/or Q08334), A2aR (Uniprot P29274), GCN2 (Uniprot P15442) and PRDM1 (Uniprot O75626).

Preference is given to the production of immune cells combining gene editing, into at least the genes encoding:
  TCR, PD1 and TGFbeta;
  TCR, CTLA4 and TGFbeta;
  TCR, PD1 and IL10R;
  TCR, CTLA4 and IL10R;
  TCR, PD1 and TGFbeta;
  TCR, CTLA4 and TGFbeta;

TCR, PD1 and GCN2;
TCR, CTLA4 and GCN2;
TCR, PD1 and A2aR;
TCR, CTLA4 and A2aR;
TCR, PD1 and PRDM1;
TCR, CTLA4 and PRDM1;
preferably by inhibiting or inactivating the expression of these proteins.

Resistance to Chemotherapy Drugs

As a preferred embodiment of the present method, one gene editing step is performed into a locus responsible for the sensitivity of the immune cells to compounds used in standard of care treatments for cancer or infection, such as drugs purine nucleotide analogs (PNA) or 6-Mercaptopurine (6MP) and 6 thio-guanine (6TG) commonly used in chemotherapy. Reducing or inactivating the genes involved into the mode of action of such compounds (referred to as "drug sensitizing genes") improves the resistance of the immune cells to same.

Examples of drug sensitizing gene are those encoding DCK (Uniprot P27707) with respect to the activity of PNA, such a clorofarabine et fludarabine, HPRT (Uniprot P00492) with respect to the activity of purine antimetabolites such as 6MP and 6TG, and GGH (Uniprot Q92820) with respect to the activity of antifolate drugs, in particular methotrexate.

According to another aspect, resistance to drugs can be conferred immune cells by overexpressing a drug resistance gene as an additional optional step of the present method of sequential gene editing. Expression of variant alleles of several genes such as dihydrofolate reductase (DHFR)(Uniprot P00374), inosine monophosphate dehydrogenase 2 (IMPDH2)(Uniprot P12268), calcineurin (Uniprot Q96LZ3, P63098 P48454, P16298 and Q08209) or methylguanine transferase (MGMT) (Uniprot P16455) have been identified to confer drug resistance to a cell according to the invention.

According to another aspect of the present invention, the engineering immune cells are made resistant to drugs purine nucleotide analogs (PNA) chemotherapy drugs, such a clorofarabine et fludarabine, as part of the gene editing step. This enables the cells to be used after or in combination with conventional anti-cancer chemotherapies.

While, according to the present invention, the first gene editing step is preferably performed on a locus encoding or regulating a surface antigen, so that sorting of the engineered cells can be carried out based on the presence/absence of said surface antigen, the second or ultimate gene editing step can be one conferring resistance of the cells to a compound, preferably a chemotherapy drug or an immune suppressive agent. By doing so, the double or triple gene edited cells can be selected and enriched by a culture step that takes place after the second or ultimate gene editing step. Also, the present method provides a first gene editing step into at least one gene encoding a T-Cell Receptor (TCR) component, in particular TCRalpha (Uniprot P01848) and TCRbeta (Uniprot P01850) and sequentially a second gene editing step into a gene expressing DCK, HPRT or GGH, to confer respectively resistance to PNA compounds, purine antimetabolites and antifolate compounds.

As a result, significant populations of triple gene edited cells can be obtained for therapeutic treatments, said cells having loci modified to reduce or inactivate the expression of:

TCR; β2m; DCK;
TCR; PD1; DCK;
TCR, CTLA4, DCK;
TCR, LAG3, DCK;

Resistance to Immune-Suppressive Treatments

According to another aspect of the present invention, the engineering immune cells are made resistant to immune-depletion treatments, such as those involving glucocorticoids or antibodies directed against immune cells surface proteins. As an example, the antibody Alemtuzumab is used to deplete CD52 positive immune cells as in many pre-cancer treatments.

Also the method of the invention can comprise a gene editing step with respect to the genes encoding or regulating the expression of CD52 (Uniprot P31358) and/or GR (Glucocorticoids receptor also referred to as NR3C1—Uniprot P04150), optionally in combination with a gene editing step leading to a reduction of the inactivation of the TCR. This approach was previously described by Poirot, L. et al. (Multiplex Genome-Edited T-cell Manufacturing Platform for "Off-the-Shelf" Adoptive T-cell Immunotherapies (2013) *Cancer. Res.* 75:3853), but as part of a method where the different loci were simultaneously gene edited.

Preferred engineered immune cells are those triple or quadruple gene edited cells detailed herein, in which CD52 and or GR are additionally inactivated.

Improving CAR Positive Immune Cell Activity and Survival

As previously stated, the present method allows introducing successive gene editing modifications into immune primary cells in a time frame that limits the impact of the gene editing steps on the subsequent expansion of these cells i.e. without reducing significantly production yields.

As shown in the examples, the present invention solves the problem of producing immune cells that express recombinant receptors, such as chimeric antigen receptors (CAR), which are triply gene edited. Representative examples of such cells obtainable according to the invention display the following phenotypes:

[CAR CS1]$^{pos}$[β2m]$^{neg}$[TCR]$^{pos}$[PD1]$^{neg}$;
[CAR CD38]$^{pos}$[β2m]$^{neg}$[TCR]$^{neg}$[PD1]$^{neg}$;
[CAR CD70]$^{pos}$[β2m]$^{neg}$[TCR]$^{neg}$[PD1]$^{neg}$;
[CAR CD22]$^{pos}$[β2m]$^{neg}$[TCR]$^{neg}$[PD1]$^{neg}$;
[CAR ROR1]$^{pos}$[β2m]$^{neg}$[TCR]$^{pos}$[PD1]$^{neg}$;
[CAR CD123]$^{pos}$[β2m]$^{neg}$[TCR]$^{neg}$[PD1]$^{neg}$;
[CAR CD19]$^{pos}$[β2m]$^{neg}$[TCR]$^{neg}$[PD1]$^{neg}$;
[CAR CD33]$^{pos}$[β2m]$^{neg}$[TCR]$^{neg}$[PD1]$^{neg}$;
[CAR 5T4]$^{pos}$[β2m]$^{neg}$[TCR]$^{pos}$[PD1]$^{neg}$;
[CAR BCMA]$^{pos}$[β2m]$^{neg}$[TCR]$^{neg}$[PD1]$^{neg}$;
[CAR Flt3]$^{pos}$[β2m]$^{neg}$[TCR]$^{neg}$[PD1]$^{neg}$;
[CAR EGFRvIII]$^{pos}$[β2m]$^{neg}$[TCR]$^{neg}$[PD1]$^{neg}$;
[CAR WT1]$^{pos}$[β2m]$^{neg}$[TCR]$^{pos}$[PD1]$^{neg}$;
[CAR HSP70]$^{pos}$[β2m]$^{neg}$[TCR]$^{neg}$[PD1]$^{neg}$;
[CAR CLL1]$^{pos}$[β2m]$^{neg}$[TCR]$^{neg}$[PD1]$^{neg}$;
[CAR CS1]$^{pos}$[β2m]$^{neg}$[TCR]$^{pos}$[CTLA4]$^{neg}$;
[CAR CD38]$^{pos}$[β2m]$^{neg}$[TCR]$^{neg}$[CTLA4]$^{neg}$;
[CAR CD70]$^{pos}$[β2m]$^{neg}$[TCR]$^{neg}$[CTLA4]$^{neg}$;
[CAR CD22]$^{pos}$[β2m]$^{neg}$[TCR]$^{neg}$[CTLA4]$^{neg}$;
[CAR ROR1]$^{pos}$[β2m]$^{neg}$[TCR]$^{pos}$[CTLA4]$^{neg}$;
[CAR CD123]$^{pos}$[β2m]$^{neg}$[TCR]$^{neg}$[CTLA4]$^{neg}$;
[CAR CD19]$^{pos}$[β2m]$^{neg}$[TCR]$^{neg}$[CTLA4]$^{neg}$;
[CAR CD33]$^{pos}$[β2m]$^{neg}$[TCR]$^{neg}$[CTLA4]$^{neg}$;
[CAR 5T4]$^{pos}$[β2m]$^{neg}$[TCR]$^{pos}$[CTLA4]$^{neg}$;
[CAR BCMA]$^{pos}$[β2m]$^{neg}$[TCR]$^{neg}$[CTLA4]$^{neg}$;
[CAR Flt3]$^{pos}$[β2m]$^{neg}$[TCR]$^{neg}$[CTLA4]$^{neg}$;
[CAR EGFRvIII]$^{pos}$[β2m]$^{neg}$[TCR]$^{neg}$[CTLA4]$^{neg}$;
[CAR WT1]$^{pos}$[β2m]$^{neg}$[TCR]$^{pos}$[CTLA4]$^{neg}$;
[CAR HSP70]$^{pos}$[β2m]$^{neg}$[TCR]$^{neg}$[CTLA4]$^{neg}$; and
[CAR CLL1]$^{pos}$[β2m]$^{neg}$[TCR]$^{neg}$[CTLA4]$^{neg}$;

[TCR]$^{neg}$ designate cells in which the expression of a component of the T-Cell receptor, such as TCRbeta or TCRalpha, has been reduced or impaired.

One preferred aspect of the present invention further concerns the problem of immune cells that express chimeric antigen receptors (CAR), which target surface molecules that are also present at the surface of said very immune cells. Such cells are typically noted:

[anti X CAR]positive (+ or pos)[X]positive (+ or pos), where X can be, for instance any of the antigen listed in table 4.

Negative impact has been observed, for instance with respect to T-cells expressing antigens CS1, CD38 or CD22 endowed with CARs targeting same: [anti-CS1 CAR]$^{pos}$, [CS1]$^{pos}$, [anti-CD38 CAR]$^{pos}$[CD38]$^{pos}$ or [anti-CD70 CAR]$^{pos}$[CD70]$^{pos}$. The CAR positive primary immune cells can attack each other resulting into immune cell depletion. This is observed even when such cells were TCR negative [TCR]$^{neg}$ The present invention provides with a technical solution to this problem by providing a method, wherein gene editing steps are sequentially performed as outlined below:
- a first gene editing step is performed to inactivate the expression of the surface molecule X;
- a CAR is expressed targeting said surface molecule X, preferably by viral transduction; and
- a second gene editing step is performed to inactivate the expression of TCR;
- optionally, a third gene editing step to inactivate the expression of an immune checkpoint gene, such as PD1 or CTLA4.

The method results into a population of engineered [antigen X CAR]$^{pos}$[antigen X]$^{neg}$[TCR]$^{neg}$ immune cells. Preferred engineered immune primary cells are triple gene edited cells, such as the following ones:

[CAR CS1]$^{pos}$[CS1]$^{neg}$[TCR]$^{neg}$[PD1]$^{neg}$;
[CAR CD38]$^{pos}$[CD38]$^{neg}$[TCR]$^{neg}$[PD1]$^{neg}$;
[CAR CD70]$^{pos}$[CD70]$^{neg}$[TCR]$^{neg}$[PD1]$^{neg}$;
[CAR CD22]$^{pos}$[CD22]$^{neg}$[TCR]$^{neg}$[PD1]$^{neg}$;
[CAR CS1]$^{pos}$[CS1]$^{neg}$[TCR]$^{neg}$[CTLA4]$^{neg}$;
[CAR CD38]$^{pos}$[CD38]$^{neg}$[TCR]$^{neg}$[CTLA4]$^{neg}$;
[CAR CD70]$^{pos}$[CD70]$^{neg}$[TCR]$^{neg}$[CTLA4]$^{neg}$;
[CAR CD22]$^{pos}$[CD22]$^{neg}$[TCR]$^{neg}$[CTLA4]$^{neg}$;
[CAR CS1]$^{pos}$[CS1]$^{neg}$[TCR]$^{neg}$[β2m]$^{neg}$;
[CAR CD38]$^{pos}$[CD38]$^{neg}$[TCR]$^{neg}$[β2m]$^{neg}$;
[CAR CD70]$^{pos}$[CD70]$^{neg}$[TCR]$^{neg}$[β2m]$^{neg}$;
[CAR CD22]$^{pos}$[CD22]$^{neg}$[TCR]$^{neg}$[β2m]$^{neg}$;

Activation and Expansion of T Cells

Whether prior to or after genetic modification, the immune cells according to the present invention can be activated or expanded, even if they can activate or proliferate independently of antigen binding mechanisms. T-cells, in particular, can be activated and expanded using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. T cells are generally expanded by contact with an agent that stimulates a CD3 TCR complex and a co-stimulatory molecule on the surface of the T cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell.

As non-limiting examples, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, IL-4, IL-7, GM-CSF, IL-10, IL-12, IL-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% 002). T-cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Therapeutic Compositions and Applications

The method of the present invention described above allows producing engineered primary immune cells within a limited time frame of about 15 to 30 days, preferably between 15 and 20 days, and most preferably between 18 and 20 days so that they keep their full immune therapeutic potential, especially with respect to their cytotoxic activity.

These cells can form or be members of populations of cells, which preferably originate from a single donor or patient. These populations of cells can be expanded under closed culture recipients to comply with highest manufacturing practices requirements and can be frozen prior to infusion into a patient, thereby providing "off the shelf" or "ready to use" therapeutic compositions.

As per the present invention, a significant number of cells originating from the same Leukapheresis can be obtained, which is critical to obtain sufficient doses for treating a patient. Although variations between populations of cells originating from various donors may be observed, the number of immune cells procured by a leukapheresis is generally about from $10^8$ to $10^{10}$ cells of PBMC. PBMC comprises several types of cells: granulocytes, monocytes and lymphocytes, among which from 30 to 60% of T-cells, which generally represents between $10^8$ to $10^9$ of primary T-cells from one donor. The method of the present invention generally ends up with a population of engineered cells that reaches generally more than about $10^8$ T-cells, more generally more than about $10^9$ T-cells, even more generally more than about $10^{10}$ T-cells, and usually more than $10^{11}$ T-cells. In general, the T-cells are gene edited at least at two different loci.

Such compositions or populations of cells can therefore be used as a medicament; especially for treating cancer, particularly for the treatment of lymphoma, but also for solid tumors such as melanomas, neuroblastomas, gliomas or carcinomas such as lung, breast, colon, prostate or ovary tumors in a patient in need thereof.

The invention is more particularly drawn to populations of primary TCR negative T-cells originating from a single donor, wherein at least 20%, preferably 30%, more preferably 50% of the cells in said population have been modified using sequence-specific reagents in at least two, preferably three different loci.

In another aspect, the present invention relies on methods for treating patients in need thereof, said method comprising at least one of the following steps:
(a) Determining specific antigen markers present at the surface of patients tumors biopsies;
(b) providing a population of engineered primary immune cells engineered by one of the methods of the present invention previously described expressing a CAR directed against said specific antigen markers;
(c) Administrating said engineered population of engineered primary immune cells to said patient, Generally, said populations of cells mainly comprises CD4 and CD8 positive immune cells, such as T-cells, which can undergo robust in vivo T cell expansion and can persist for an extended amount of time in-vitro and in-vivo.

The treatments involving the engineered primary immune cells according to the present invention can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

In another embodiment, said isolated cell according to the invention or cell line derived from said isolated cell can be used for the treatment of liquid tumors, and preferably of T-cell acute lymphoblastic leukemia.

Adult tumors/cancers and pediatric tumors/cancers are also included.

The treatment with the engineered immune cells according to the invention may be in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The present invention thus can provide more than 10, generally more than 50, more generally more than 100 and usually more than 1000 doses comprising between $10^6$ to $10^8$ gene edited cells originating from a single donor's or patient's sampling.

The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

Combination Therapy Involving at Least Two Sub-Populations of T Cells.

The present invention encompasses a whole range of double, triple or quadruple gene edited cells now available for therapeutic use, including any of those illustrated herein, which could not be obtained by the prior art methods. Especially, those cells are engineered with a reduced risk of unwanted recombination or translocation at the different gene edited loci, making them safer for therapeutic use.

As a further advantage of the present method of sequential gene editing is also the possibility to create subpopulations of primary immune cells from an initial population originating from a single donor or patient, which subpopulations are gene edited at different loci.

As an example, the primary immune cells from the donor or patient can be made less-alloreactive by performing a first gene editing step into a TCR gene or any gene implicated in the self/non-selfrecognition, and then after an expansion step, the population can be split into two subpopulations, which respectively undergo a second gene editing step that will target distinct loci in said subpopulations. Typically, CD4+ positive and CD8+ positive immune cells can be (see FIG. 8) treated separately before being pooled together at a desired ratio to increase potency of the therapeutic compositions. This method will result into subpopulations of engineered primary immune cells that will not display exactly the same properties. Accordingly, the present invention is also drawn to compositions of populations of primary TCR negative T-cells resulting from a single donor comprising at least two subpopulations of T-cells, said subpopulations comprising, for instance different gene edited immune checkpoint genes. Such sub-populations of cells can be selected, for instance, from:

TCR negative and PD1 negative,
TCR negative and CD52 negative,
TCR negative and CTLA4 negative,
TCR negative and dCK negative,
TCR negative and GR negative,
TCR negative and GGH negative,
TCR negative and HPRT negative,
TCR negative and β2m negative.

The resulting cells can be optionally transformed to express chimeric antigen receptor to provide allogeneic CAR T Cells with various specificities, in particular as part of sub-populations expressing chimeric receptors respectively directed to different surface molecules.

Such sub-populations can be used separately or in combination with each other into compositions for therapeutic treatments, in the same way as previously described with a single population of cells.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

Chimeric antigen receptor (CAR) is a term that encompasses molecules which combine an extracellular binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFv), comprising the light ($V_L$) and the heavy ($V_H$) variable fragment of a target antigen specific monoclonal antibody joined by a flexible linker, fused to the intracellular signaling domain of the T cell antigen receptor complex zeta chain and have the ability, when expressed in immune effector cells, to redirect antigen recognition based on the monoclonal antibody's specificity. CAR can be single-chain or multi-chain as described in WO2014039523. Binding domain other than scFv can also be used for predefined targeting of lymphocytes, such as camelid or shark (VNAR) single-domain antibody fragments or receptor ligands like a vascular endothelial growth factor polypeptide, an integrin-binding peptide, heregulin or an IL-13 mutein, antibody binding domains, antibody hypervariable loops or CDRs as non-limiting examples.

"Recombinant TCR" are artificial polypeptide constructs consisting preferably of a single amino acid strand, which like native heterodimeric TCRs bind to MHC-peptide complexes. Recombinant TCRs are preferably single-chain polypeptides, such as described by Stone J. D., et al. [A novel T cell receptor single-chain signaling complex mediates antigen-specific T cell activity and tumor control (2014) *Cancer Immunol. Immunother.* 63(11):1163-76], Such single chain TCRs generally comprise:

an α segment constituted by a human TCR α chain variable region sequence fused to the N terminus of a human TCR α chain constant region extracellular sequence, a β segment constituted by a human TCR β chain variable region sequence fused to the N terminus of a human TCR β chain constant region extracellular sequence, and a linker sequence linking the C terminus of the α segment to the N terminus of the β segment, or vice versa, the constant region extracellular sequences of the α and β segments being linked by a disulfide bond, the length of the linker sequence and the position of the disulfide bond being such that the variable region sequences of the α and β segments are mutually orientated substantially as in native αβ T cell receptors.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 10 base pairs (bp) in length, more preferably of 14-55 bp. Rare-cutting endonucleases significantly increase homologous recombination by inducing DNA double-strand breaks (DSBs) at a defined locus thereby allowing gene repair or gene insertion therapies (Pingoud, A. and G. H. Silva (2007). Precision genome surgery. *Nat. Biotechnol.* 25(7): 743-4.).

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of RNA guided target sequences, are those genome sequences that can hybridize the guide RNA which directs the RNA guided endonuclease to a desired locus.

by "mutation" is intended the substitution, deletion, insertion of up to one, two, three, four, five, six, seven, eight, nine, ten, eleven, twelve, thirteen, fourteen, fifteen, twenty, twenty five, thirty, forty, fifty, or more nucleotides/amino acids in a polynucleotide (cDNA, gene) or a polypeptide sequence. The mutation can affect the coding sequence of a gene or its regulatory sequence. It may also affect the structure of the genomic sequence or the structure/stability of the encoded mRNA.

by "variant" is intended a catalytically active mutant of an endonuclease reagent according to the present invention.

the term "locus" is the specific physical location of a DNA sequence (e.g. of a gene) into a genome. The term "locus" can refer to the specific physical location of a rare-cutting endonuclease target sequence on a chromosome or on an infection agent's genome sequence. Such a locus can comprise a target sequence that is recognized and/or cleaved by a sequence-specific endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to limit the scope of the claimed invention.

EXAMPLES

Example 1: Simultaneous Vs. Sequential Electroporation of TRAC and CD52 TALE-Nucleases into T Cells In order to analyze the impact of sequential electroporation of TALE-nuclease reagents on the overall survival of T-cells and gene knock-out efficiency, we have submitted activated primary human T cells from a single donor sample to electroporation by using TALEN® reagents (Cellectis, Paris, France) specific for TRAC gene (TCR alpha chain) according to the following experimental procedure. The amino acid sequences of the various TALEN® heterodimers used in this experiment are given in Table 3):

Briefly, frozen human PBMCs (AllCells) were thawed and activated using anti CD3 and anti CD28 antibodies-coated beads (Dynabeads, Life Technologies, Carlsbad, Calif., United States) for 3 days. After magnetic beads removal (Day 4), 5×106 activated T cells were transfected with 10 µg of both mRNA encoding TALEN either simultaneously or sequentially with a 6 hour, 20 hour or 40 hour intervals by using AgilePulse electroporator (BTX Instrument Division, Harvard Apparatus, Inc., Holliston, Mass. 01746-1388) protocols. Electroporated T cells were platted back in tissue culture vessels in Xvivo hematopoietic medium (Lonza, CH-4002 Basel, Switzerland) supplemented with 5% human AB serum and rIL2 (100 UI/ml) for a total of 12 days. Cells were passaged every 2 or 3 days for numeration and media renewal.

Surface expression of TCR and CD52 protein was measured by cytometry using specific monoclonal antibodies and a Macsquant cytometer (Miltenyi) at D10 post activation. Furthermore, T cells growth was monitored from D4 to D12, by Trypan blue exclusion cell numeration.

On FIG. 9 are presented the percentage of TCR+, CD52+, double positive TCR/CD52+ and double negative TCR/CD52− cells measured 6 days after electroporation according to the electroporation schedule. The data show that 70 to 80% of TCR KO and 65 to 75% of CD52 KO is achievable whatever the electroporation conditions, sequential or simultaneous. Furthermore, the percentage of double negative cells is comparable for all the tested conditions. This validates the finding that sequential electroporation does not reduce the rate of gene editing success.

Having shown that sequential electroporation does not affect the efficiency of TALE-nuclease mediated gene knock out, we sought to see if cellular growth was impaired when cells are electroporated twice within 24 or 48 h intervals, by monitoring electroporation conditions, cell and growth.

Figure 10:
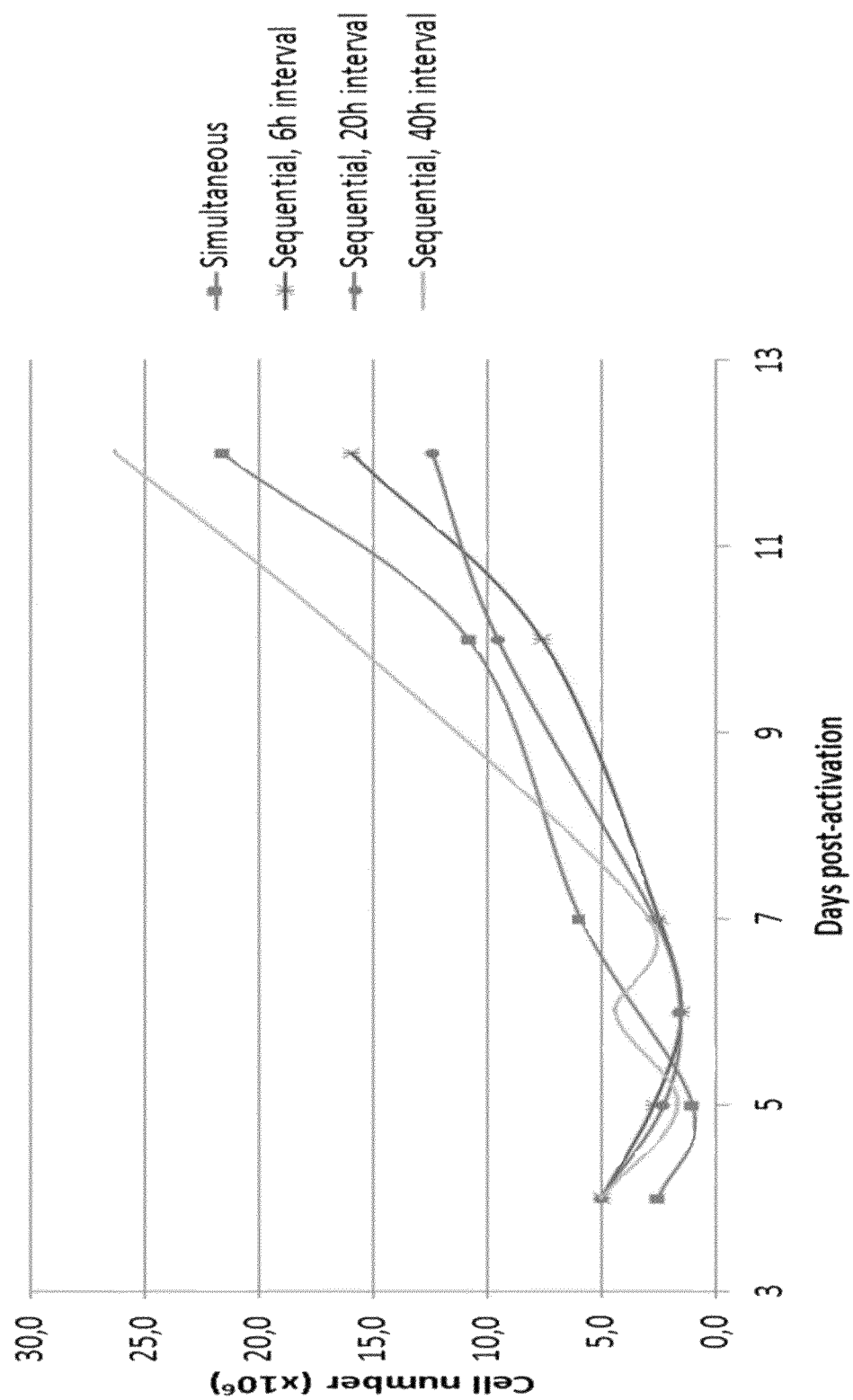

Data shown in FIG. 10 indicated that cellular growth was similar for all tested conditions with an advantage for the T cells sequentially transfected with a 40 h interval.

Altogether, these data demonstrated that sequential electroporation does not affect KO efficiency and cellular growth.

Example 2: Simultaneous or Sequential Electroporation of mRNA Encoding TRAC and PD1 TALE-Nucleases into T Cells Simultaneous electroporation of two TALE-Nuclease heterodimers was found to be highly efficient for performing simultaneous gene knock-out in Poirot et al. (Multiplex Genome-Edited T-cell Manufacturing Platform for "Off-the-Shelf" Adoptive T-cell Immunotherapies (2015) *Cancer Res.* 75: 3853-64). However, unwanted events such as off-site cleavage or translocation were found to occur in certain instances. For instance, co-transfection of mRNA encoding TRAC TALEN® and PD1 TALEN® leads to the occurring of off-site cleavage activity due to the pairing of the TRAC TALEN left arm and PD1 TALEN left arm. Frequency of off-site cleavage (as well as on-site cleavage) is defined by the frequency of mutated sequences (either nucleotide deletion or addition) that are generated after endonucleases cleavage and unfaithful religation of broken ends. The amino acid sequences used in this experiment encoding the various TALEN® heterodimers for TRAC (SEQ ID NO.1 and 2) and PD1 (SEQ ID NO. 5 and 6) are given in Table 3)

Potential off-site hits can be identified in silico with an algorithm according to several parameters including mainly TALE-nuclease DNA binding sequences, number of mismatches and position of those, length of the spacer between the 2 binding domains. According to this computer search, numerous potential off-site targets have been identified in the human genome for TRAC and PD1 TALEN® combination. The 15 first target sequences with the highest score have been verified experimentally by PCR and Deep Sequencing. One out of the 15, "Off-Site 3", has been found to be a true off-site target since about 1% of mutagenesis events (or Insertion/deletion, InDels events) was observed when T cell were transfected simultaneously with TRAC and PD1 TALEN®.

Since the data showed in example 1, demonstrated that sequential electroporation of TALEN did not affect KO efficiency and cell expansion, we sought to determine whether this sequential transfection strategy could abolish cleavage into the "Off-Site 3".

Briefly, frozen human PBMCs (AllCells) were thawed and activated using anti CD3 and anti CD28 antibodies-coated beads (Dynabeads, LifeTech) for 3 days. 5×10$^6$ activated T cells were transfected with 10 µg of both TALEN mRNA either simultaneously or sequentially with a 6 hour, 20 hour or 40 hour intervals by using AgilePulse electroporator (BTX Instrument Division, Harvard Apparatus, Inc., Holliston, Mass. 01746-1388) protocols. Electroporated T cells were platted back in tissue culture vessels in Xvivo (Lonza) media supplemented with 5% human AB serum and rIL2 (100 UI/ml) for a total of 6 days. Cells were passaged every 2 or 3 days for numeration and media renewal. At the end of the 6 day period, genomic DNA was extracted from transfected T cells and subjected to PCR amplification using specific primers allowing the amplification of TRAC and PD1 "On-Site" genomic targets and 5 "Off-Site" targets including "Off-Site 3". PCR products are then purified and modified for subsequent deep sequencing analysis using the Illumina technology. About 80,000 reads for each samples were computed.

Data are presented on FIG. 11. As previously observed, the simultaneous transfection of TRAC and PD-1 TALEN® into T-cells induces a high level of indels at TRAC and PD-1 on-site targets respectively. About 1% of indels is also observed at the "Off-Site 3" target whereas no significant mutagenesis event is observed for the other predicted off-site targets OF1, OF2, OF4 and OF5. Sequential transfection of TRAC TALEN first and PD-1 TALEN 24 h or 40 h later has no or minor impact on the level of mutagenesis at on site TRAC and On site PD-1. However, we observed a significant decrease of the % of indels for the OF3 at 24 h (0.4%) and 40 h (0.04%), These data indicate that sequential electroporation of TALEN allows the abrogation of unwanted events such as off-site cleavage without affecting KO efficiency.

Example 3: Simultaneous or Sequential Electroporation of CD38, TRAC and CD52 TALEN into T Cells In order to analyze the impact of sequential TALEN electroporation on overall survival of T cells and gene knock-out efficiency, we have transfected activated human T cells with TALENs specific for TRAC gene (TCR alpha chain), CD52 and CD38 (Amino acid sequences are given in Table 3) according to the following experimental procedure:

Briefly, frozen human PBMCs (AllCells) are thawed and activated using anti CD3 and anti CD28 antibodies-coated beads (TransAct, Miltenyi) for 3 days. At day 4 post thawing, 10×106 activated T cells are transfected with 10 µg of both TALEN mRNA either simultaneously or sequentially with a 24 hour (Day 5) or 48 hour (Day 6) intervals using Cellectis proprietary AgilPulse electroporator and protocols. The following conditions have been tested and compared in terms of KO efficiency and cell growth.

TABLE 2 gene editing efficiency of the sequential gene editing strategies

| | Transfection Day post thawing | | | % cells in the population | | | |
|---|---|---|---|---|---|---|---|
| | D4 | D5 | D6 | [CD38]⁻ | [TCRαβ]⁻ | [CD52]⁻ | [CD38]⁻[TCRαβ]⁻[CD52]⁻ |
| A | CD38/TRAC/CD52 | | | 66.1 | 67.8 | 57 | 35.2 |
| B | CD38 | TRAC/CD52 | | 63.2 | 64.6 | 64.6 | 27.1 |
| C | CD38 | | TRAC/CD52 | 63.8 | 68 | 60.6 | 36.7 |
| D | CD38/TRAC | CD52 | | 61.6 | 73.8 | 50.5 | 27.6 |
| E | CD38/TRAC | | CD52 | 67.5 | 72.9 | 69.4 | 40.2 |
| F | CD38/CD52 | TRAC | | 65.7 | 69.4 | 63.2 | 34.7 |
| G | CD38/CD52 | | TRAC | 65.6 | 73.7 | 61.9 | 35.7 |
| H | CD38 | TRAC | CD52 | 61.2 | 69.8 | 58.3 | 28.3 |
| I | CD38 | CD52 | TRAC | 59.2 | 73.4 | 56.9 | 28.4 |
| Untransfected | | | | | | | 0.1 |

Electroporated T cells are platted back in tissue culture vessels in Xvivo (Lonza) media supplemented with 5% human AB serum and rIL2 (100 UI/ml) for a total of 15 days. Cells are passaged every 2 or 3 days for numeration and media renewal.

Surface expression of TCR, CD38 and CD52 protein is measured by cytometry using specific antibodies and a Canto10 cytometer (Becton-Dickinson) at D13 post thawing. Furthermore, T cells growth is monitored from Day 5 to Day 15 by Trypan blue exclusion cell numeration.

Table 2 presents the percentage of single negative T cells (CD38−, TCR− and CD52−) and the percentage of triple negative T cells (CD38−TCR−CD52−), according to the electroporation scheduling. These data show that 65 to 74% of TCR KO, 57 to 70% of CD52 KO, thus comparable among conditions. The best results is obtained when CD38 and TRAC TALEN are transfected 48 h prior to CD52 TALEN transfection (Table 2, row E and FIG. 12, row E). The best results are obtained when CD38 and TRAC TALEN are transfected 48 h prior to CD52 TALEN transfection, as for TCR and CD52 (Table 4, row E and FIG. 12, row E). However, all tested conditions show little variation in the % of triple negative T cells ranging from 27% to 40%. Furthermore, the best percentage of triple knock out efficiency is obtained with sequential electroporation of CD38 and TRAC TALEN 48 h prior to CD52 TALEN.

Having validated that sequential electroporation does not affect the efficacy of TALEN mediated gene knock out, we sought to see if cellular growth is impaired when cells are subjected to 2 electroporation shocks within 24 or 48 h intervals. According to electroporation conditions, cell growth is measured from day 5 to Day 13 post-thawing (FIG. 12).

At day 15, the best growth rate is observed when the 3 TALEN are electroporated simultaneously. T cell growth curves for all sequential electroporation conditions are comparable with best results for conditions where a 48 h interval is performed between the two electroporation shocks (conditions C, E and G of Table 4 and FIG. 12).

These data indicate that cellular growth is similar for all tested sequential conditions with an advantage for T cells sequentially transfected with a 48 h interval.

Altogether, these data demonstrate that sequential electroporation does not affect KO efficiency and cellular growth.

Example 4: Generation of Triple KO (TCR/PD-1/B2M) CAR CD22 T Cells

T-cells were cultured from PBMC and activated as described in Example 1, in order to produce [TCR]$^{neg}$[PD1]$^{neg}$[B2M]$^{neg}$ therapeutic immune cells endowed with a CAR directed against CD22 antigen.

Furthermore, in order to analyze the impact of sequential TALEN electroporation on gene knock-out efficiency and triple KO CAR T cells activity, the cells were edited either simultaneously or sequentially with TALEN specific for TRAC gene (SEQ ID NO. 1 and 2), PD-1 (SEQ ID NO. 9 and 6) and B2M (beta-2-microglobulin, SEQ ID NO. 10 and 11). The sequential protocol is illustrated in FIG. 13. In both cases, T-cells were transduced with lentiviral particles for the expression of CAR targeting the antigen CD22 (SEQ ID NO. 12).

TALEN mRNA were generated from linearized plasmid DNA encoding each TALEN arm of interest. An in vitro RNA synthesis kit for RNA generation was used (Invitrogen #AMB1345-5). RNA was purified using the Qiagen RNAeasy Kit (#74106) and eluted into T solution from BTX (47-0002).

Frozen human PBMCs from two different donors are thawed at 2×106 cells per ml on day prior activation and transduction step, in complete X-Vivo media (X-VIVO 15, Lonza #04-418Q; 5% Human serum AB, Gemini #100-318; 20 ng/mL IL-2, Miltenyi #130-097-743). One day post thawing, cells are transduced as described in (Poirot et al. (2015) Multiplex Genome-Edited T-cell Manufacturing Platform for "Off-the-Shelf" Adoptive T-cell Immunotherapies *Cancer Res*. 75: 3853-64) with lentiviral particles allowing the expression of a Chimeric Antigen Receptor targeting CD22 antigen containing a mimotope sequence (highlighted in bold in SEQ ID NO. 12). Cells are further activated the same day using anti CD3 and anti CD28 antibodies-coated beads (TransAct, Miltenyi) according to manufacturer's protocol for 4 days.

At day 5 post thawing, T cells were electroporated with a dose response of mRNAs encoding TRAC TALEN (10 µg), PD-1 TALEN (from 30 µg to 70 µg) and B2M TALEN (from 30 µg to 70 µg) either simultaneously or sequentially with a 48 hour intervals using Cellectis proprietary AgilPulse electroporator and protocols. After each electroporation step cells were incubated for 15 minutes at 30° C. and then incubated at 37° C. Thirteen days post thawing positive T-cells were analyzed for triple KO efficacy by first re-stimulating a portion of T cells with TransACT to induce PD-1 expression. Two days later, re-stimulated cells were labeled with antibodies at a 1:50 dilution of each antibody for 15 minutes at 4° C. (Miltenyi; TCR #130-091-236, HLA-ABC #130-101-467, PD-1 #130-099-878). For all the different donors tested sequential editing provide the best triple KO efficacy ranging from 20 up to 40% (FIG. 14).

Triple KO T-cells were then enriched using a biotin and column based negative purification system for TCR and B2M dKO cells (Miltenyi; biotin-TCR #130-098-219, bitoin-HLA-ABC #130-101-463, Biotin beads #130-090-485, MS columns #130-042-201). Under this purification scheme, only TCR and B2M positive cells bind the MS column, and the TCR/B2M dKO cells of interest are enriched in the flowthrough fraction with 97% or greater purity. Triple KO CAR-T cells enriched for TCR/B2M dKO were further incubated for an additional two days before assessing CAR-T cells activity. On day 15, T cells were analyzed for CD22 CAR cytotoxicity by co-culturing T cells with CD22 expressing Raji-Luciferase+ targets at effector to target ratios of 30:1, 15:1, 5:1, and 1:1 for 5 hours before luminescence was quantified using the ONE Glo luminescence kit (Promega). FIG. 15 demonstrates that triple KO CD22 CAR T were as active as their wild type counter part (non gene edited T-cells endowed with the same CAR CD22)

TABLE 3

Sequence of TALEN ® used in experiments.

| Sequence name | Ref. sequence | Amino acid sequence of TALEN ® used in experiments |
|---|---|---|
| TRAC TALEN Left | SEQ ID NO.1 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPQQVVAIASNGGGKQALETVQRLLPVLCQAHGLTPQQVVAIASN NGGGKQALETVQRLLPVLCQAHGLTPQQVVAIASNGGGKQALETVQRLL PVLCQAHGLTPEQVVAIASHDGGKQALETVQRLLPVLCQAHGLTPEQVV AIASHDGGKQALETVQRLLPVLCQAHGLTPEQVVAIASHDGGKQALETV QRLLPVLCQAHGLTPEQVVAIASNIGGKQALETVQALLPVLCQAHGLTPE QVVAIASHDGGKQALETVQRLLPVLCQAHGLTPEQVVAIASNIGGKQAL ETVQALLPVLCQAHGLTPQQVVAIASNNGGKQALETVQRLLPVLCQAH GLTPEQVVAIASNIGGKQALETVQALLPVLCQAHGLTPQQVVAIASNGG GKQALETVQRLLPVLCQAHGLTPEQVVAIASNIGGKQALETVQALLPVLC QAHGLTPQQVVAIASNGGGKQALETVQRLLPVLCQAHGLTPEQVVAIA SHDGGKQALETVQRLLPVLCQAHGLTPQQVVAIASNGGGRPALESIVAQ LSRPDPALAALTNDHLVALACLGGRPALDAVKKGLGDPISRSQLVKSELEE KKSELRHKLKYVPHEYIELIEIARNSTQDRILEMKVMEFFMKVYGYRGKHL GGSRKPDGAIYTVGSPIDYGVIVDTKAYSGGYNLPIGQADEMQRYVEEN QTRNKHINPNEWWKVYPSSVTEFKFLFVSGHFKGNYKAQLTRLNHITNC NGAVLSVEELLIGGEMIKAGTLTLEEVRRKFNNGEINFAAD |
| TRAC TALEN Right | SEQ ID NO. 2 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPEQVVAIASHDGGKQALETVQRLLPVLCQAHGLTPQQVVAIASN GGGKQALETVQRLLPVLCQAHGLTPEQVVAIASHDGGKQALETVQRLLP VLCQAHGLTPEQVVAIASNIGGKQALETVQALLPVLCQAHGLTPQQVVA IASNNGGKQALETVQRLLPVLCQAHGLTPEQVVAIASHDGGKQALETVQ RLLPVLCQAHGLTPQQVVAIASNGGGKQALETVQRLLPVLCQAHGLTPQ QVVAIASNNGGKQALETVQRLLPVLCQAHGLTPQQVVAIASNNGGKQA LETVQRLLPVLCQAHGLTPQQVVAIASNGGGKQALETVQRLLPVLCQAH GLTPEQVVAIASNIGGKQALETVQALLPVLCQAHGLTPEQVVAIASHDG GKQALETVQRLLPVLCQAHGLTPEQVVAIASNIGGKQALETVQALLPVLC QAHGLTPEQVVAIASHDGGKQALETVQRLLPVLCQAHGLTPQQVVAIAS NNGGKQALETVQRLLPVLCQAHGLTPQQVVAIASNGGGRPALESIVAQL SRPDPALAALTNDHLVALACLGGRPALDAVKKGLGDPISRSQLVKSELEE KKSELRHKLKYVPHEYIELIEIARNSTQDRILEMKVMEFFMKVYGYRGKHL GGSRKPDGAIYTVGSPIDYGVIVDTKAYSGGYNLPIGQADEMQRYVEEN QTRNKHINPNEWWKVYPSSVTEFKFLFVSGHFKGNYKAQLTRLNHITNC NGAVLSVEELLIGGEMIKAGTLTLEEVRRKFNNGEINFAAD |
| CD52 TALEN Left | SEQ ID NO. 3 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPQQVVAIASNGGGKQALETVQRLLPVLCQAHGLTPEQVVAIASH DGGKQALETVQRLLPVLCQAHGLTPEQVVAIASHDGGKQALETVQRLLP VLCQAHGLTPQQVVAIASNGGGKQALETVQRLLPVLCQAHGLTPEQVV AIASHDGGKQALETVQRLLPVLCQAHGLTPEQVVAIASHDGGKQALETV QRLLPVLCQAHGLTPQQVVAIASNGGGKQALETVQRLLPVLCQAHGLTP EQVVAIASNIGGKQALETVQALLPVLCQAHGLTPEQVVAIASHDGGKQA LETVQRLLPVLCQAHGLTPQQVVAIASNGGGKQALETVQRLLPVLCQAH GLTPEQVVAIASHDGGKQALETVQRLLPVLCQAHGLTPEQVVAIASNIG GKQALETVQALLPVLCQAHGLTPEQVVAIASHDGGKQALETVQRLLPVL CQAHGLTPEQVVAIASHDGGKQALETVQRLLPVLCQAHGLTPEQVVAIA SNIGGKQALETVQALLPVLCQAHGLTPQQVVAIASNGGGRPALESIVAQ LSRPDPALAALTNDHLVALACLGGRPALDAVKKGLGDPISRSQLVKSELEE KKSELRHKLKYVPHEYIELIEIARNSTQDRILEMKVMEFFMKVYGYRGKHL GGSRKPDGAIYTVGSPIDYGVIVDTKAYSGGYNLPIGQADEMQRYVEEN QTRNKHINPNEWWKVYPSSVTEFKFLFVSGHFKGNYKAQLTRLNHITNC NGAVLSVEELLIGGEMIKAGTLTLEEVRRKFNNGEINFAAD |

TABLE 3-continued

Sequence of TALEN ® used in experiments.

| Sequence name | Ref. sequence | Amino acid sequence of TALEN ® used in experiments |
|---|---|---|
| CD52 TALEN Right | SEQ ID NO. 4 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPQQVVAIASNGGGKQALETVQRLLPVLCQAHGLTPQQVVAIASN NGGGKQALETVQRLLPVLCQAHGLTPEQVVAIASHDGGKQALETVQRLLP VLCQAHGLTPQQVVAIASNGGGKQALETVQRLLPVLCQAHGLTPEQVV AIASHDGGKQALETVQRLLPVLCQAHGLTPQQVVAIASNGGGKQALET VQRLLPVLCQAHGLTPQQVVAIASNGGGKQALETVQRLLPVLCQAHGLT PEQVVAIASNIGGKQALETVQALLPVLCQAHGLTPEQVVAIASHDGGKQ ALETVQRLLPVLCQAHGLTPEQVVAIASHDGGKQALETVQRLLPVLCQA HGLTPQQVVAIASNGGGKQALETVQRLLPVLCQAHGLTPQQVVAIASN NGGKQALETVQRLLPVLCQAHGLTPQQVVAIASNGGGKQALETVQRLL PVLCQAHGLTPEQVVAIASNIGGKQALETVQALLPVLCQAHGLTPEQVV AIASHDGGKQALETVQRLLPVLCQAHGLTPQQVVAIASNGGGRPALESI VAQLSRPDPALAALTNDHLVALACLGGRPALDAVKKGLGDPISRSQLVKS ELEEKKSELRHKLKYVPHEYIELIEIARNSTQDRILEMKVMEFFMKVYGYR GKHLGGSRKPDGAIYTVGSPIDYGVIVDTKAYSGGYNLPIGQADEMQRY VEENQTRNKHINPNEWWKVYPSSVTEFKFLFVSGHFKGNYKAQLTRLN HITNCNGAVLSVEELLIGGEMIKAGTLTLEEVRRKFNNGEINFAAD |
| PD-1 TALEN Left | SEQ ID NO. 5 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPEQVVAIASGNGGKQALETVQALLPVLCQAHGLTPEQVVAIASH DGGKQALETVQRLLPVLCQAHGLTPEQVVAIASHDGGKQALETVQRLLP VLCQAHGLTPQQVVAIASNGGGKQALETVQRLLPVLCQAHGLTPEQVV AIASHDGGKQALETVQRLLPVLCQAHGLTPQQVVAIASNGGGKQALET VQRLLPVLCQAHGLTPQQVVAIASNNGGKQALETVQRLLPVLCQAHGL TPQQVVAIASNGGGKQALETVQRLLPVLCQAHGLTPQQVVAIASGRGG KQALETVQRLLPVLCQAHGLTPQQVVAIASNNGGKQALETVQRLLPVLC QAHGLTPQQVVAIASNNGGKQALETVQRLLPVLCQAHGLTPQQVVAIA SNNGGKQALETVQRLLPVLCQAHGLTPEQVVAIASHDGGKQALETVQR LLPVLCQAHGLTPEQVVAIASHDGGKQALETVQRLLPVLCQAHGLTPEQ VVAIASNIGGKQALETVQALLPVLCQAHGLTPQQVVAIASNGGGRPALE SIVAQLSRPDPALAALTNDHLVALACLGGRPALDAVKKGLGDPISRSQLV KSELEEKKSELRHKLKYVPHEYIELIEIARNSTQDRILEMKVMEFFMKVYGY RGKHLGGSRKPDGAIYTVGSPIDYGVIVDTKAYSGGYNLPIGQADEMQR YVEENQTRNKHINPNEWWKVYPSSVTEFKFLFVSGHFKGNYKAQLTRLN HITNCNGAVLSVEELLIGGEMIKAGTLTLEEVRRKFNNGEINFAAD |
| PD-1 TALEN Right | SEQ ID NO. 6 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPEQVVAIASHDGGKQALETVQRLLPVLCQAHGLTPQQVVAIASN GGGKQALETVQRLLPVLCQAHGLTPEQVVAIASHDGGKQALETVQRLLP VLCQAHGLTPQQVVAIASNGGGKQALETVQRLLPVLCQAHGLTPQQVV AIASNGGGKQALETVQRLLPVLCQAHGLTPQQVVAIASNGGGKQALET VQRLLPVLCQAHGLTPQQVVAIASNNGGKQALETVQRLLPVLCQAHGL TPEQVVAIASNIGGKQALETVQALLPVLCQAHGLTPQQVVAIASNGGGK QALETVQRLLPVLCQAHGLTPEQVVAIASHDGGKQALETVQRLLPVLCQ AHGLTPQQVVAIASNGGGKQALETVQRLLPVLCQAHGLTPQQVVAIAS NNGGKQALETVQRLLPVLCQAHGLTPEQVVAIASNGGKQALETVQRLLP VLCQAHGLTPQQVVAIASNNGGKQALETVQRLLPVLCQAHGLTPEQVV AIASHDGGKQALETVQRLLPVLCQAHGLTPQQVVAIASNGGGRPALESI VAQLSRPDPALAALTNDHLVALACLGGRPALDAVKKGLGDPISRSQLVKS ELEEKKSELRHKLKYVPHEYIELIEIARNSTQDRILEMKVMEFFMKVYGYR GKHLGGSRKPDGAIYTVGSPIDYGVIVDTKAYSGGYNLPIGQADEMQRY VEENQTRNKHINPNEWWKVYPSSVTEFKFLFVSGHFKGNYKAQLTRLN HITNCNGAVLSVEELLIGGEMIKAGTLTLEEVRRKFNNGEINFAAD |
| CD38 TALEN Left | SEQ ID NO. 7 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPQQVVAIASNGGKQALETVQRLLPVLCQAHGLTPEQVVAIASH DGGKQALETVQRLLPVLCQAHGLTPQQVVAIASNNGGKQALETVQRLL PVLCQAHGLTPEQVVAIASNIGGKQALETVQALLPVLCQAHGLTPQQVV AIASNNGGKQALETVQRLLPVLCQAHGLTPQQVVAIASNGGGKQALET VQRLLPVLCQAHGLTPQQVVAIASNGGGKQALETVQRLLPVLCQAHGLT PEQVVAIASHDGGKQALETVQRLLPVLCQAHGLTPEQVVAIASNIGGKQ ALETVQALLPVLCQAHGLTPQQVVAIASNNGGKQALETVQRLLPVLCQA HGLTPEQVVAIASHDGGKQALETVQRLLPVLCQAHGLTPEQVVAIASHD GGKQALETVQRLLPVLCQAHGLTPEQVVAIASHDGGKQALETVQRLLPV LCQAHGLTPQQVVAIASNNGGKQALETVQRLLPVLCQAHGLTPQQVVA IASNNGGKQALETVQRLLPVLCQAHGLTPQQVVAIASNGGGRPALESIV |

TABLE 3-continued

Sequence of TALEN® used in experiments.

| Sequence name | Ref. sequence | Amino acid sequence of TALEN® used in experiments |
|---|---|---|
| | | AQLSRPDPALAALTNDHLVALACLGGRPALDAVKKGLGDPISRSQLVKSE LEEKKSELRHKLKYVPHEYIELIEIARNSTQDRILEMKVMEFFMKVYGYRG KHLGGSRKPDGAIYTVGSPIDYGVIVDTKAYSGGYNLPIGQADEMQRYV EENQTRNKHINPNEWWKVYPSSVTEFKFLFVSGHFKGNYKAQLTRLNHI TNCNGAVLSVEELLIGGEMIKAGTLTLEEVRRKFNNGEINFAAD |
| CD38 TALEN Right | SEQ ID NO. 8 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPEQVVAIASNIGGKQALETVQALLPVLCQAHGLTPQQVVAIASN NGGKQALETVQRLLPVLCQAHGLTPEQVVAIASNIGGKQALETVQALLP VLCQAHGLTPQQVVAIASNNGGKQALETVQRLLPVLCQAHGLTPEQVV AIASNIGGKQALETVQALLPVLCQAHGLTPQQVVAIASNNGGKQALETV QRLLPVLCQAHGLTPEQVVAIASHDGGKQALETVQRLLPVLCQAHGLTP EQVVAIASHDGGKQALETVQRLLPVLCQAHGLTPQQVVAIASNNGGKQ ALETVQRLLPVLCQAHGLTPQQVVAIASNNGGKQALETVQRLLPVLCQA HGLTPEQVVAIASHDGGKQALETVQRLLPVLCQAHGLTPEQVVAIASNI GGKQALETVQALLPVLCQAHGLTPQQVVAIASNNGGKQALETVQRLLP VLCQAHGLTPEQVVAIASHDGGKQALETVQRLLPVLCQAHGLTPEQVV AIASNIGGKQALETVQALLPVLCQAHGLTPQQVVAIASNGGGRPALESIV AQLSRPDPALAALTNDHLVALACLGGRPALDAVKKGLGDPISRSQLVKSE LEEKKSELRHKLKYVPHEYIELIEIARNSTQDRILEMKVMEFFMKVYGYRG KHLGGSRKPDGAIYTVGSPIDYGVIVDTKAYSGGYNLPIGQADEMQRYV EENQTRNKHINPNEWWKVYPSSVTEFKFLFVSGHFKGNYKAQLTRLNHI TNCNGAVLSVEELLIGGEMIKAGTLTLEEVRRKFNNGEINFAAD |
| PD1 TALEN Left 2 | SEQ ID NO. 9 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPEQVVAIASKLGGKQALETVQALLPVLCQAHGLTPEQVVAIASHD GGKQALETVQRLLPVLCQAHGLTPEQVVAIASHDGGKQALETVQRLLPV LCQAHGLTPQQVVAIASNGGGKQALETVQRLLPVLCQAHGLTPEQVVAI ASHDGGKQALETVQRLLPVLCQAHGLTPQQVVAIASNGGGKQALETVQ RLLPVLCQAHGLTPQQVVAIASYKGGKQALETVQRLLPVLCQAHGLTPQ QVVAIASNGGGKQALETVQRLLPVLCQAHGLTPQQVVAIASNNGGKQA LETVQRLLPVLCQAHGLTPQQVVAIASNNGGKQALETVQRLLPVLCQAH GLTPQQVVAIASNNGGKQALETVQRLLPVLCQAHGLTPQQVVAIASNN GGKQALETVQRLLPVLCQAHGLTPEQVVAIASHDGGKQALETVQRLLPV LCQAHGLTPEQVVAIASHDGGKQALETVQRLLPVLCQAHGLTPEQVVAI ASNIGGKQALETVQALLPVLCQAHGLTPQQVVAIASNGGGRPALESIVA QLSRPDPALAALTNDHLVALACLGGRPALDAVKKGLGDPISRSQLVKSEL EEKKSELRHKLKYVPHEYIELIEIARNSTQDRILEMKVMEFFMKVYGYRGK HLGGSRKPDGAIYTVGSPIDYGVIVDTKAYSGGYNLPIGQADEMQRYVE ENQTRNKHINPNEWWKVYPSSVTEFKFLFVSGHFKGNYKAQLTRLNHIT NCNGAVLSVEELLIGGEMIKAGTLTLEEVRRKFNNGEINFAAD |
| B2M TALEN left | SEQ ID NO. 10 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPQQVVAIASNNGGKQALETVQRLLPVLCQAHGLTPQQVVAIASN NGGKQALETVQRLLPVLCQAHGLTPEQVVAIASHDGGKQALETVQRLLP VLCQAHGLTPEQVVAIASHDGGKQALETVQRLLPVLCQAHGLTPQQVV AIASNGGGKQALETVQRLLPVLCQAHGLTPEQVVAIASNGGGKQALET VQRLLPVLCQAHGLTPEQVVAIASNIGGKQALETVQALLPVLCQAHGLTP QQVVAIASNNGGKQALETVQRLLPVLCQAHGLTPEQVVAIASHDGGKQ ALETVQRLLPVLCQAHGLTPQQVVAIASNGGGKQALETVQRLLPVLCQA HGLTPQQVVAIASNNGGKQALETVQRLLPVLCQAHGLTPQQVVAIASN GGGKQALETVQRLLPVLCQAHGLTPQQVVAIASNNGGKQALETVQRLL PVLCQAHGLTPEQVVAIASHDGGKQALETVQRLLPVLCQAHGLTPQQV VAIASNGGGKQALETVQRLLPVLCQAHGLTPQQVVAIASNGGGRPALES IVAQLSRPDPALAALTNDHLVALACLGGRPALDAVKKGLGDPISRSQLVK SELEEKKSELRHKLKYVPHEYIELIEIARNSTQDRILEMKVMEFFMKVYGYR GKHLGGSRKPDGAIYTVGSPIDYGVIVDTKAYSGGYNLPIGQADEMQRY VEENQTRNKHINPNEWWKVYPSSVTEFKFLFVSGHFKGNYKAQLTRLN HITNCNGAVLSVEELLIGGEMIKAGTLTLEEVRRKFNNGEINFAAD |
| B2M TALEN right | SEQ ID NO. 11 | MGDPKKKRKVIDIADLRTLGYSQQQQEKIKPKVRSTVAQHHEALVGHGF THAHIVALSQHPAALGTVAVKYQDMIAALPEATHEAIVGVGKQWSGAR ALEALLTVAGELRGPPLQLDTGQLLKIAKRGGVTAVEAVHAWRNALTGA PLNLTPEQVVAIASNIGGKQALETVQALLPVLCQAHGLTPQQVVAIASN NGGKQALETVQRLLPVLCQAHGLTPEQVVAIASHDGGKQALETVQRLLP VLCQAHGLTPEQVVAIASHDGGKQALETVQRLLPVLCQAHGLTPQQVV AIASNGGGKQALETVQRLLPVLCQAHGLTPEQVVAIASHDGGKQALETV QRLLPVLCQAHGLTPEQVVAIASHDGGKQALETVQRLLPVLCQAHGLTP EQVVAIASNIGGKQALETVQALLPVLCQAHGLTPQQVVAIASNNGGKQ |

TABLE 3-continued

Sequence of TALEN ® used in experiments.

| Sequence name | Ref. sequence | Amino acid sequence of TALEN ® used in experiments |
|---|---|---|
| | | ALETVQRLLPVLCQAHGLTPQQVVAIASNNGGKQALETVQRLLPVLCQA HGLTPEQVVAIASHDGGKQALETVQRLLPVLCQAHGLTPEQVVAIASHD GGKQALETVQRLLPVLCQAHGLTPEQVVAIASNIGGKQALETVQALLPVL CQAHGLTPQQVVAIASNNGGKQALETVQRLLPVLCQAHGLTPEQVVAI ASNIGGKQALETVQALLPVLCQAHGLTPQQVVAIASNGGGRPALESIVA QLSRPDPALAALTNDHLVALACLGGRPALDAVKKGLGDPISRSQLVKSEL EEKKSELRHKLKYVPHEYIELIEIARNSTQDRILEMKVMEFFMKVYGYRGK HLGGSRKPDGAIYTVGSPIDYGVIVDTKAYSGGYNLPIGQADEMQRYVE ENQTRNKHINPNEWWKVYPSSVTEFKFLFVSGHFKGNYKAQLTRLNHIT NCNGAVLSVEELLIGGEMIKAGTLTLEEVRRKFNNGEINFAAD |
| CD22 CAR | SEQ ID NO. 12 | MALPVTALLLPLALLLHAARPGGGGSCPYSNPSLCSGGGGSGGGGSQV QLQQSGPGLVKPSQTLSLTCAISGDSVSSNSAAWNWIRQSPSRGLEWL GRTYYRSKWYNDYAVSVKSRITINPDTSKNQFSLQLNSVTPEDTAVYYCA REVTGDLEDAFDIWGQGTMVTVSSGGGGSGGGGSGGGGSDIQMTQS PSSLSASVGDRVTITCRASQTIWSYLNWYQQRPGKAPNLLIYAASSLQSG VPSRFSGRGSGTDFTLTISSLQAEDFATYYCQQSYSIPQTFGQGTKLEIKSD PGSGGGGSCPYSNPSLCSGGGGSELPTQGTFSNVSTNVSPAKPTTTACP YSNPSLCAPTTTPAPRPPTPAPTIASQPLSLRPEACRPAAGGAVHTRGLDF ACDIYIWAPLAGTCGVLLLSLVITLYCRRGRKKLLYIFKQPFMRPVQTTQE EDGCSCRFPEEEEGGCELRVKFSRSADAPAYQQGQNQLYNELNLGRREE YDVLDKRRGRDPEMGGKPRRKNPQEGLYNELQKDKMAEAYSEIGMKG ERRRGKGHDGLYQGLSTATKDTYDALHMQALPPRE |

TABLE 4

Cluster of differentiation (CD) antigen markers of various cancers found to be expressed on the surface of T-cells

| Antigen | Other Names | Structure | main Distribution | Function |
|---|---|---|---|---|
| CD1a | T6 | IgSF, MHC-like | cortical thymocytes, Langerhans cells, DC | antigen presentation, with beta2m |
| CD1b | T6 | IgSF, MHC-like | cortical thymocytes, Langerhans cells, DC | antigen presentation, with beta2m |
| CD1c | T6 | IgSF, MHC-like | cortical thymocytes, Langerhans cells, DC, B subset | antigen presentation, with beta2m |
| CD1d | | IgSF, MHC-like | intestinal epith, B subset, monolow, DC | antigen presentation, with beta2m |
| CD3 gamma, CD3 delta | T3 | IgSF | T, thymocyte subset | with TCR, TCR surface expression/ signal transduction |
| CD3 epsilon | T3 | IgSF | T, thymocyte subset | with TCR, TCR surface expression/ signal transduction |
| CD4 | T4 | IgSF | thymocyte subset, T subset, mono, mac | MHC class II coreceptor, HIV receptor, T cell differentiation / activation |
| CD5 | T1, Tp67 | Scavenger R SF | thymocytes, T, B subset, B-CLL | CD72 receptor, TCR or BCR signaling, T-B interaction |
| CD7 | | IgSF | hematopoietic progenitors, thymocytes, T, NK | T costimulation |
| CD8a | T8, Leu-2 | IgSF | thymocyte subset, T subset, NK | MHC class I coreceptor, receptor for some mutated HIV-1, T cell differentiation/activation |
| CD8b | | IgSF | thymocyte subset, T subset | |
| CD9 | p24, MRP-1 | TM4SF | pre-B, eosinophils, basophils, platelets, Tact | cellular adhesion and migration |
| CD10 | CALLA, NEP, gp100 | type II TM | B precursors, T precursors, neutrophils | zinc-binding metalloproteinase, B cell development |
| CD11a | LFA-1, integrin alphaL | lntegrin family | lymph, gran, mono, mac | CD11a/CD18 receptor for ICAM-1, -2, -3, intercellular adhesion, T costimulation |
| CD11b | Mac-1, integrin alphaM | lntegrin family | myeloid cells, NK | binds CD54, ECM, iC3b |
| CD11c | p150, 95, CR4, integrin alphaX | lntegrin family | DC, myeloid cells, NK, B, T subset | binds CD54, fibrinogen and iC3b |
| CD13 | Aminopeptidase N, APN | type II TM | myeloid cells | zinc-binding metalloproteinase, antigen processing, receptor for corona virus strains |
| CD14 | LPS-R | GPI-linked | mono, mac, Langerhans cells, granlow | receptor for LPS/LBP, LPS recognition |

TABLE 4-continued

Cluster of differentiation (CD) antigen markers of various cancers found to be expressed on the surface of T-cells

| Antigen | Other Names | Structure | main Distribution | Function |
|---|---|---|---|---|
| CD15 | Lewis-x, Lex | CHO | neutrophils, eosinophils, mono | adhesion |
| CD16a | FcgammaRIIIA | IgSF | neutrophils, mac, NK | component of low affinity Fc receptor, phagocytosis and ADCC |
| CD16b | FcgammaRIIIB | IgSF | neutrophils | component of low affinity Fc receptor, phagocytosis and ADCC |
| CD20 | B1, Bp35 | TM4SF | B, T subset | B cell activation |
| CD21 | C3DR, CR2, EBV-R | CCRSF | B, FDC, T subset | complement C3d and EBV receptor, complex with CD19 and CD81, BCR coreceptor |
| CD22 | BL-CAM, Siglec-2 | IgSF, sialoadhesins | B | adhesion, B-mono, B-T interactions |
| CD23 | FcepsilonRII | C-type lectin | B, activated mac, eosinophils, FDC, platelets | CD19-CD21-CD81 receptor, IgE low affinity receptor, signal transduction |
| CD24 | BA-1 | GPI-linked | thymocytes, erythrocytes, peripheral lymph, myeloid | binds P-selectin |
| CD25 | Tac, p55 | type I TM | Tact, Bact, lymph progenitors | IL-2Ralpha, with IL-2Rbeta and gamma to form high affinity complex |
| CD31 | PECAM-1 | IgSF | mono, platelets, gran, endoth, lymph subset | CD38 receptor, adhesion |
| CD33 | p67, Siglec-3 | IgSF, sialoadhesins | myeloid progenitors, mono, gran, DC, mast cells, Tact | adhesion |
| CD37 | | TM4SF | B, Tlow, granlow | signal transduction |
| CD38 | T10 | | variable levels on majority of hematopoietic cells, high expression on plasma cells, B and Tact | ecto-ADP-ribosyl cyclase, cell activation |
| CD40 | | TNFRSF | B, mono, mac, FDC, endoth, T subset | CD154 receptor, B differentiation/ costimulation, isotype-switching, rescues B cells from apoptosis |
| CD43 | Leukosialin, sialophorin | Sialomucin, type I TM | leukocytes, except resting B, plateletslow | inhibition of T cell interaction, CD54R, adhesion |
| CD44 | H-CAM, Pgp-1 | hyaladherin family | hematopoietic and non-hematopoietic cells, except platelets, hepatocytes, testis | binds hyaluronic acid, adhesion |
| CD45 | LCA, T200, B220 | | hematopoietic cells, multiple isoforms from alternative splicing | tyrosine phosphatase, enhanced TCR & BCR signals |
| CD45RA | | | B, T subset(naive), mono | exon A isoforms of CD45 |
| CD45RB | | | T subset, B, mono, mac, gran | exon B isoforms of CD45 |
| CD45RO | | | Tact, memory T, B subset, mono, mac, gran | isoform of CD45 lacking A, B, C exons |
| CD46 | MCP | CCRSF | nucleated cells | membrane cofactor protein, binds C3b & C4b allowing degradation by Factor I, measles virus receptor |
| CD47 | IAP | IgSF | hematopoietic cells, epith, endoth, fibroblasts, other tissues | leukocyte adhesion, migration, activation |
| CD48 | Blast-1 | IgSF | broad, all leukocytes | cell adhesion |
| CD52 | CAMPATH-1 | | thymocytes, T, B (not plasma cells), mono, mac | |
| CD53 | | TM4SF | leukocytes, DC, osteoblasts, osteoclasts | signal transduction |
| CD55 | DAF | GPI-linked | hematopoietic, endoth | binds C3b, complement regulation |
| CD56 | NCAM | IgSF | NK, T subset, neurons, some large granular lymphocyte leukemias, myeloid leukemias | adhesion |
| CD57 | HNK-1, Leu-7 | | NK subset, T subset | |
| CD58 | LFA-3 | IgSF | hematopoietic, non-hematopoietic cells | CD2 receptor, adhesion |
| CD59 | Protectin, MAC-inhibitor | GPI-linked | hematopoietic, non-hematopoietic cells | binds complement C8 and C9, blocks assembly of membrane attack complex |
| CD60a | GD3 | CHO | T subset, platelets, thymic epith, astrocytes | costimulation |
| CD63 | LIMP, LAMP-3 | TM4SF | activated platelets, mono, mac | lysosomal membrane protein, moves to cell surface after activation |
| CD68 | Macrosialin, gp110 | Sialomucin | intracellularly in mono, mac, neutrophils, basophils, large lymph, mast cells, DC, myeloid progenitors, liver | |
| CD69 | AIM | C-type lactin | Tact, B, NK and gran, thymocytes, platelets, Langerhans cells | signal transduction |
| CD70 | Ki-24 | TNFSF | Bact and Tact | CD27 ligand, T and B cell costimulation |
| CD74 | Ii, invariant chain | | B, mac, mono, Langerhans cells, DC, Tact | MHC class II traffic and function |
| CD79a | Iga | IgSF | B | component of BCR, BCR surface expression and signal transduction |
| CD79b | Igb | IgSF | B | component of BCR, BCR surface expression and signal transduction |
| CD81 | TAPA-1 | TM4SF | T, B, NK, thymocytes, DC, endoth, fibroblast, neuroblastomas, melanomas | complex with CD19 & CD21, signaling, T costimulation |
| CD82 | R2 | TM4SF | leukocytes | signal transduction |
| CD83 | HB15 | IgSF | Bact and Tact, DC, Langerhans cells | |
| CDw84 | | | mono, platelets, B, T subset, mac subset | |
| CD86 | B70, B7-2 | IgSF | mono, DC, Bact and Tact | binds to CD28, CD152, T costimulation |

TABLE 4-continued

Cluster of differentiation (CD) antigen markers of various cancers found to be expressed on the surface of T-cells

| Antigen | Other Names | Structure | main Distribution | Function |
|---|---|---|---|---|
| CD87 | UPA-R | GPI-linked | gran, mono, NK, Tact, endoth, fibroblasts | urokinase plasminogen activator receptor, inflammatory cell invasion, metastasis |
| CD90 | Thy-1 | IgSF, GPI-linked | CD34 +hematopoietic subset, neurons | hematopoietic stem cell and neuron differentiation |
| CD94 | KP43 | C-type lactin | NK, T subset | complex with NKG2, inhibits NK function |
| CD95 | Apo-1, Fas | TNFRSF | lymph (high upon activation), mono, neutrophils | FasL (CD178) receptor, apoptosis |
| CD96 | TACTILE | IgSF | NK, Tact | adhesion of activated T and NK |
| CD97 | | TM7SF | Bact and Tact, mono, gran | |
| CD98 | 4F2 | | T, B, NK, gran, all human cell lines | cellular activation |
| CD99 | MIC2, | E2 | leukocytes | T cell activation, adhesion |
| CD100 | | | hematopoietic cells except immature bone marrow cells, RBC and platelets | cell adhesion, cellular activation |
| CD103 | HML-1, alpha6, integrin alphaE | Integrin family | intraepithelial lymph, lymph subset, activated lymph | with integrin beta7, binds E-cadherin, lymph homing/retention |
| CD107a | LAMP-1 | | activated platelets, T, endoth, metastatic tumors | a lysosomal membrane protein |
| CD107b | LAMP-2 | | activated platelets, T, endoth, metastatic tumors | a lysosomal membrane protein |
| CD109 | | | Tact and platelets, CD34+ subset, endoth | |
| CD123 | IL-3R | CRSF | lymph subset, basophils, hematopoietic progenitors, mac, DC, megakaryocytes | IL-3Ralpha, with CDw131 |
| CD146 | MUC18, S-endo | IgSF | endoth, melanomas, FDC, Tact | adhesion |
| CD154 | CD40L, gp39, TRAP | TNFSF | Tact | CD40 ligand, B and DC costimulation |
| CD158a | p58.1 | IgSF, KIR family | NK subset, T subset | inhibition of NK cell cytolytic activity, MHC class-I specific NK receptor |
| CD158b | p58.2 | IgSF, KIR family | NK subset, T subset | inhibition of NK cell cytolytic activity, MHC class-I specific NK receptor |
| CD163 | 130kD | Scavenger receptor SF | mono, mac | |
| CD164 | MGC-24 | epith, mono, lymphlow, bone marrow stromal cells, CD34+ erythroid progenitors | hematopoietic progenitor cell-stromal cell interaction | |
| CD168 | RHAMM | | mono, T subset, thymocyte subset, intracellularly in breast cancer cells | adhesion, tumor migration, metastasis |
| CD171 | L1 | IgSF | CNS, PNS, glial cells, mono, T subset, B, DC, several human tumor cells | kidney morphogenesis, lymph node architecture, T costimulation, neurohistogenesis, homotypic interaction, binds CD9, CD24, CD56, CD142, CD166, integrins |
| CD177 | NB1 | | neutrophil subset | |
| CD178 | FasL, CD95L | TNFSF | Tact, testis | CD95 ligand, apoptosis, immune privilege, soluble form in serum |
| CD180 | RP-105 | LRRF, TLR family | B subset, mono, DC | B cell activation, LPS signaling, with MD-1 |
| CD182 | CXCR2, IL-8RB | GPCR1 family | neutrophils, basophils, NK, T subset, mono | binding of IL-8 induces chemotaxis of neutrophils |
| CD185 | CXCR5, BLR1 | GPCR1 family | mature B and Burkitt Lymphoma cells | with chemokine BLC, possible regulatory function in Burkitt Lymphomagenesis and/or B differentiation, activation of mature B |
| CD191 | CCR1, MIP-1alphaR, RANTES-R | GPCR1 family | T, mono, stem cell subset | binds C-C type chemokines and transduces signal by increasing intracellular calcium ion levels |
| CD193 | CCR3, CKR3 | GPCR1 family | eosinophils, lower expression in neutrophils and mono, T subset | binds eotaxin, eotaxin-3, MCP-3, MCP-4, RANTES & MIP-1 delta, alternative coreceptor with CD4 for HIV-1 infection. |
| CD196 | CCR6, LARC receptor, DRY6 | GPCR1 family | T subset, B, DC subset | binds MIP-3alpha/LARC |
| CD197 | CCR7 | | T subset, DC Subset | 6Ckine and MIP-2beta receptor |
| CD200 | OX-2 | | thymocytes, endoth, B, Tact | inhibition of immune response |
| CD209 | DC-SIGN | | DC subset | ICAM-3 receptor, HIV-1 binding protein |
| CD227 | MUC1, EMA | Mucin family, type I TM | epith, stem cell subset, FDC, mono, B subset, some myelomas | adhesion, signaling, binds CD169, CD54, & selectins |
| CD231 | TALLA-1, A15 | TM4SF | T leukemias, neuroblastomas, brain neurons | marker for T cell acute lymphoblastic leukemia |
| CD246 | ALK, Ki-1 | | anaplastic T cell leukemias, small intestine, testis, brain, not on normal lymph | brain development, implicated in ALK lymphomas |

TABLE 4-continued

Cluster of differentiation (CD) antigen markers of various cancers found to be expressed on the surface of T-cells

| Antigen | Other Names | Structure | main Distribution | Function |
| --- | --- | --- | --- | --- |
| CD254 | TRANCE, RANKL, OPGL | TNFSF | lymph node & BM stroma Tact | binds OPG and RANK, osteoclast differentiation, enhances DC to stimulate naive-T proliferation |
| CD263 | TRAIL-R3, DcR1, LIT | | peripheral blood lymphocytes | receptor for TRAIL but lacks death domain |
| CD272 | BTLA | IgSF | Tact, B, remains on Th1 | HVEM receptor, inhibitory response |
| CD273 | B7DC, PD-L2, PDCD1L2 | IgSF | DC subset, mono, mac | PD-1 receptor, costimulation or suppression of T proliferation |
| CD276 | B7-H3 | B7 Family, ASV | in vitro cultured DC and mono, Tact, mammary tissue | costimulation, T activation |
| CD277 | BT3.1, butyrophilin SF3 A1, BTF5 | B7/BT family, ASV | T, B, NK, mono, DC, endoth, CD34 +cells, tumor cell lines | T activation |
| CD279 | PD1, SLEB2 | | Tact and Bact | B7-H1 & B7-DC receptor, autoimmune disease and peripheral tolerance |
| CD298 | Na +/K +-ATPase beta3 subunit | | broad | transport sodium & potassium ions across membrane |
| CD300a | CMRF35H, IRC1, IRp60 | IgSF, ASV | NK, mono, neutrophils, T and B subset and lymphocytic cell lines, AML | unknown |
| CD300c | CMRF35A, LIR | IgSF | mono, neutrophils, monocytic cell lines, B & T subsets | unknown |
| CD304 | BDCA4, neuropilin 1 | semaphorin family | neurons, CD4+/CD25+ Treg, DC, endothelial and tumor cells | interacts with VEGF165 & semaphorins, co-receptor with plexin, axonal guidance, angiogenesis, cell survival, migration |
| CD305 | LAIR1 | IgSF, ASV | NK, B, T, mono | inhibitory receptor on NK and T cells |
| CD314 | NKG2D, KLR | Type II lectin-like receptor | NK, CD8+ activated, NK1.1 +T, some myeloid cells | binds MHC class I, MICA, MICB, Rae1 & ULBP4, activates cytolysis and cytokine production, costimulation |
| CD317 | BST2, HM1.24 | Type II | B, T, NK, mono, DC, fibroblast cell line, myeloma | pre-B cell growth, overexpressed in multiple myeloma |
| CD319 | CS1, CRACC, SLAMF7 | SLAM receptor family | BCells, Dendritic Cells, NK, NKT | multiple myeloma |

The invention claimed is:

1. A method for introducing genetic modifications at different loci of a primary immune cell, comprising the sequential steps of:
   a) subjecting said primary immune cell to a first electroporation step to introduce at least a first rare-cutting endonuclease into said immune cell;
   b) cultivating said primary immune cell for 48 to 72 hours, thereby enabling said first rare-cutting endonuclease to modify its genome at a first locus,
   c) subjecting said modified primary immune cell to at least a second electroporation step from 48 to 72 hours after the first electroporation step to introduce at least a second rare-cutting endonuclease into said cell, and
   d) cultivating and expanding said primary immune cell thereby enabling said second sequence-specific reagent to modify its genome at a second locus to generate an immune cell that is modified at said first locus and said second locus.

2. The method according to claim 1, wherein a purification of a modified primary immune cell is performed between step b) and c) relying on the presence or absence of a product resulting from the expression or the deletion of a gene that is modified at least at said first locus.

3. The method according to claim 1, wherein said method comprises at least one further step of submitting said primary immune cell to a third electroporation step to introduce at least a third rare-cutting endonuclease into said cell.

4. The method according to claim 1, wherein a transduction step is introduced between b) and c) with a viral vector.

5. The method according to claim 4, wherein said transduction step involves an integrative lentiviral or retroviral vector for stable expression of a transgene.

6. The method according to claim 5, wherein said transgene encodes a Chimeric Antigen Receptor (CAR).

7. The method according to claim 4, wherein said transduction step involves a non-integrative viral vector.

8. The method according to claim 7, wherein said non-integrative viral vector is used as a template for homologous recombination or NHEJ integration of said transgene into the immune cell's genome.

9. The method according to claim 4, wherein said first rare-cutting endonuclease is acting on a genomic sequence that facilitates the transduction step.

10. The method according to claim 1, wherein said first rare-cutting endonuclease is acting on a genomic sequence that facilitates the genetic modification of step d).

11. The method according to claim 1, wherein step b) is performed below 35° C.

12. The method according to claim 1, wherein said immune cell is a T-cell.

13. The method according to claim 12, comprising a preliminary step of activating a primary T-cell by signal transduction prior to step a).

14. The method according to claim 12, wherein said first rare-cutting endonuclease permanently reduces or prevents expression of a T-cell receptor (TCR) by the primary T-cell.

15. The method according to claim 1, wherein said first or second rare-cutting endonuclease permanently reduces or prevents expression of at least one gene encoding an immune checkpoint.

16. The method according to claim 15, wherein said at least one gene encoding an immune checkpoint is selected from Programmed cell death protein 1 (PD1), Cytotoxic T-lymphocyte protein 4 (CTLA4), Serine/threonine-protein phosphatase 2A catalytic subunit alpha isoform (PPP2CA), Serine/threonine-protein phosphatase 2A catalytic subunit beta isoform (PPP2CB), Tyrosine-protein phosphatase non-receptor type 6 (PTPN6), Tyrosine-protein phosphatase non-receptor type 22 (PTPN22), Programmed cell death 1 ligand 1 (PDCD1), Lymphocyte activation gene 3 protein (LAG3), Hepatitis A virus cellular receptor 2 (HAVCR2), B- and T-lymphocyte attenuator (BTLA), CD160, T-cell immuno-receptor with Ig and ITIM domains (TIGIT), T-cell surface protein tactile (CD96), Cytotoxic and regulatory T-cell molecule (CRTAM), Leukocyte-associated immunoglobulin-like receptor 1 (LAIR1), Sialic acid-binding Ig-like lectin 7 (SIGLEC7), Sialic acid-binding Ig-like lectin 9 (SIGLEC9), Natural killer cell receptor 2B4 (CD244), Tumor necrosis factor receptor superfamily member 10A (TNFRSF10B), Tumor necrosis factor receptor superfamily member 10A (TNFRSF10A), Caspase-8 (CASP8), Caspase-10 (CASP10), Caspase-3 (CASP3), Caspase-6 (CASP6), Caspase-7(CASP7), FAS-associated death domain protein (FADD), Tumor necrosis factor receptor superfamily member 6 (FAS), TGF-beta receptor type-2 (TGFBRII), TGF-beta receptor type-1 (TGFRBRI), Mothers against decapentaplegic homolog 2 (SMAD2), Mothers against decapentaplegic homolog 3 (SMAD3), Mothers against decapentaplegic homolog 4 (SMAD4), Mothers against decapentaplegic homolog (SMAD10), Ski oncogene (SKI), Ski-like protein (SKIL), Homeobox protein TGIF1 (TGIF1), Interleukin-10 receptor subunit alpha (IL10RA), Interleukin-10 receptor subunit beta (IL10RB), Heme oxygenase 2 (HMOX2), Interleukin-6 receptor subunit alpha (IL6R), Interleukin-6 receptor subunit beta (IL6ST), eIF-2-alpha kinase GCN2(EIF2AK4), Tyrosine-protein kinase CSK (CSK), Phosphoprotein associated with glycosphingolipid-enriched microdomains 1 (PAG1), L-type lectin-domain containing receptor kinase (SIT1), Forkhead box protein P3 (FOXP3), PR domain zinc finger protein 1 (PRDM1), Basic leucine zipper transcriptional factor ATF-like (BATF), Guanylate cyclase soluble subunit alpha-2 (GUCY1A2), Guanylate cyclase soluble subunit alpha-3 (GUCY1A3), Guanylate cyclase soluble subunit beta-2 (GUCY1B2), and Guanylate cyclase soluble subunit beta-3 (GUCY1B3).

17. The method according to claim 1, wherein said first or second rare-cutting endonuclease permanently confers resistance of said primary immune cell against drugs or immune depleting agents by inactivating a gene expressing CD52, Deoxycytidine kinase (dCK), Gamma-glutamyl hydrolase (GGH) or Hypoxanthine-guanine phosphoribosyltransferase (HPRT).

18. The method according to claim 1, wherein a final step of purification of a modified primary immune cell is performed relying on the presence or absence of at least one product resulting from the expression or the deletion of one gene that is modified by said first and/or second rare-cutting endonuclease.

19. The method according to claim 1, wherein the different loci are selected from:
TCR and PD1,
TCR and CD52,
TCR and CTLA4,
TCR and dCK,
TCR and GGH,
TCR and HPRT, and
TCR and Beta-2-microglobulin (β2m).

20. The method according to claim 1, wherein the different loci are TCR and PD1.

21. The method according to claim 1, wherein the different loci are TCR and CD52.

22. The method according to claim 1, wherein the different loci are TCR and CTLA4.

23. The method according to claim 1, wherein the different loci are TCR and dCK.

24. The method according to claim 1, wherein the different loci are TCR and GGH.

25. The method according to claim 1, wherein the different loci are TCR and HPRT.

26. The method according to claim 1, wherein the different loci are TCR and Beta-2-microglobulin (β2m).

27. The method according to claim 1, wherein at least one of said first or second endonuclease is a Transcription activator-like effector (TALE) nuclease.

* * * * *